US011261242B2

United States Patent
Adams et al.

(10) Patent No.: US 11,261,242 B2
(45) Date of Patent: Mar. 1, 2022

(54) ANTI-ALPHA-SYNUCLEIN ANTIBODIES

(71) Applicant: UCB Biopharma SRL, Brussels (BE)

(72) Inventors: Ralph Adams, Slough (GB); Patrick Downey, Brussels (BE); Terence Seward Baker, Slough (GB); Kerry Louise Tyson, Slough (GB); Lorenzo De Lichtervelde, Brussels (BE); Daniel John Lightwood, Slough (GB); David James McMillan, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

(21) Appl. No.: 16/771,993

(22) PCT Filed: Dec. 13, 2018

(86) PCT No.: PCT/EP2018/084697
§ 371 (c)(1),
(2) Date: Jun. 11, 2020

(87) PCT Pub. No.: WO2019/115674
PCT Pub. Date: Jun. 20, 2019

(65) Prior Publication Data
US 2021/0107971 A1 Apr. 15, 2021

(30) Foreign Application Priority Data
Dec. 15, 2017 (GB) .................................. 1720975

(51) Int. Cl.
C07K 16/18 (2006.01)
A61K 39/00 (2006.01)

(52) U.S. Cl.
CPC ........ *C07K 16/18* (2013.01); *A61K 2039/505* (2013.01); *C07K 2317/24* (2013.01); *C07K 2317/34* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,890,535 B1 | 5/2005 | Schenk | |
| 7,306,945 B2 | 12/2007 | Chilcote et al. | |
| 7,358,331 B2 | 4/2008 | Chilcote et al. | |
| 7,727,957 B2 | 6/2010 | Schenk et al. | |
| 7,910,333 B2 | 3/2011 | Chilcote et al. | |
| 7,919,088 B2 | 4/2011 | Schenk et al. | |
| 7,977,316 B2 | 7/2011 | Schenk | |
| 8,092,801 B2 | 1/2012 | Schenk et al. | |
| 8,147,833 B2 | 4/2012 | Schenk et al. | |
| 8,506,959 B2 | 8/2013 | Schenk et al. | |
| 8,609,820 B2 | 12/2013 | Saldanha et al. | |
| 8,632,776 B2 | 1/2014 | Nordström et al. | |
| 8,673,593 B2 | 3/2014 | Chilcote et al. | |
| 8,741,293 B2 | 6/2014 | Dodel et al. | |
| 8,790,644 B2 | 7/2014 | Saldanha et al. | |
| 8,809,506 B2 | 8/2014 | Lannfelt et al. | |
| 8,940,276 B2 | 1/2015 | Weihofen et al. | |
| 8,968,734 B2 | 3/2015 | Nordström et al. | |
| 9,315,569 B2 | 4/2016 | Lannfelt et al. | |
| 9,493,553 B2 | 11/2016 | Kaluza et al. | |
| 9,605,056 B2 | 3/2017 | Barbour et al. | |
| 9,670,274 B2 | 6/2017 | Kaluza et al. | |
| 9,732,148 B2 | 8/2017 | Ayalon et al. | |
| 9,890,209 B2 | 2/2018 | Kaluza et al. | |
| 9,896,504 B2 | 2/2018 | Weihofen et al. | |
| 10,081,674 B2 | 9/2018 | Barbour et al. | |
| 2003/0166558 A1 | 9/2003 | Frangione et al. | |
| 2004/0136993 A1 | 7/2004 | Schenk et al. | |
| 2005/0037013 A1 | 2/2005 | Schenk et al. | |
| 2005/0196818 A1 | 9/2005 | Chilcote et al. | |
| 2008/0014194 A1 | 1/2008 | Schenk et al. | |
| 2011/0059093 A1* | 3/2011 | Bohrmann | A61P 25/00 424/139.1 |
| 2013/0072663 A1 | 3/2013 | Chilcote et al. | |
| 2013/0108546 A1 | 5/2013 | Saldanha et al. | |
| 2014/0241984 A1 | 8/2014 | El-Agnaf | |
| 2014/0369940 A1 | 12/2014 | Weihofen et al. | |
| 2015/0140003 A1 | 5/2015 | Kaluza et al. | |

(Continued)

FOREIGN PATENT DOCUMENTS

DE 102011008153 A1 7/2012
EP 1185296 B1 1/2011

(Continued)

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*
Mayo "Parkinson's disease" accessed from mayoclinic.org on Nov. 7, 2018 (Year: 2018).*

(Continued)

*Primary Examiner* — Adam Weidner
(74) *Attorney, Agent, or Firm* — Medler Ferro Woodhouse & Mills PLLC

(57) ABSTRACT

The present invention relates to antibodies binding alpha synuclein and fragments thereof capable of binding alpha synuclein as a monomer and in fibrils and preventing alpha synuclein aggregation induced by alpha synuclein fibrils. The antibodies of the present invention are for use in the treatment of alpha synucleinopathies, including Parkinson's disease.

21 Claims, 16 Drawing Sheets
Specification includes a Sequence Listing.

(56) References Cited

U.S. PATENT DOCUMENTS

| | | |
|---|---|---|
| 2016/0060331 A1 | 3/2016 | Schenk et al. |
| 2017/0320940 A1 | 11/2017 | Ayalon et al. |
| 2017/0349651 A1 | 12/2017 | Schenk et al. |
| 2018/0134775 A1 | 5/2018 | El-Agnaf et al. |
| 2018/0134776 A1 | 5/2018 | El-Agnaf et al. |
| 2018/0134777 A1 | 5/2018 | El-Agnaf et al. |
| 2018/0237510 A1 | 8/2018 | Kaluza et al. |

FOREIGN PATENT DOCUMENTS

| | | |
|---|---|---|
| EP | 2371396 B1 | 1/2014 |
| EP | 2272539 B1 | 3/2014 |
| EP | 2807188 B1 | 12/2014 |
| EP | 2370466 B1 | 5/2015 |
| EP | 1578253 B1 | 8/2015 |
| EP | 2903648 B1 | 8/2015 |
| EP | 2949666 B1 | 12/2015 |
| EP | 2583978 B1 | 4/2016 |
| EP | 3067066 B1 | 9/2016 |
| EP | 2450056 B1 | 3/2017 |
| EP | 2361928 B1 | 4/2017 |
| EP | 1633189 B1 | 7/2017 |
| EP | 2539366 B1 | 11/2017 |
| EP | 2723379 B1 | 9/2018 |
| EP | 3369433 A1 | 9/2018 |
| EP | 2282758 B1 | 11/2018 |
| WO | 2002050121 A1 | 6/2002 |
| WO | 2004041067 A3 | 5/2004 |
| WO | 2005013889 A3 | 2/2005 |
| WO | 2005047860 A3 | 5/2005 |
| WO | 2006020581 A3 | 2/2006 |
| WO | 2006045037 A3 | 4/2006 |
| WO | 2007012061 A3 | 1/2007 |
| WO | 2007021255 A1 | 2/2007 |
| WO | 2008103472 A3 | 8/2008 |
| WO | 2009133521 A3 | 11/2009 |
| WO | 2010069603 A1 | 6/2010 |
| WO | 2011/104696 A1 | 9/2011 |
| WO | 2011104696 A1 | 9/2011 |
| WO | 2011107544 A1 | 9/2011 |
| WO | 2012061785 A3 | 5/2012 |
| WO | 2012061786 A1 | 5/2012 |
| WO | 2012/177972 A1 | 12/2012 |
| WO | 2012177972 A1 | 12/2012 |
| WO | 2013/063516 A1 | 5/2013 |
| WO | 2013063516 A1 | 5/2013 |
| WO | 2013/112945 A1 | 8/2013 |
| WO | 2013180201 A1 | 12/2013 |
| WO | 2014/058924 A2 | 4/2014 |
| WO | 2014058924 A3 | 4/2014 |
| WO | 2014132210 A1 | 9/2014 |
| WO | 2015051159 A1 | 4/2015 |
| WO | 2015075011 A1 | 5/2015 |
| WO | 2015075635 A2 | 5/2015 |
| WO | 2015155694 A1 | 10/2015 |
| WO | 2015179867 A1 | 11/2015 |
| WO | 2015197772 A1 | 12/2015 |
| WO | 2016040903 A1 | 3/2016 |
| WO | 2016040905 A1 | 3/2016 |
| WO | 2016040907 A1 | 3/2016 |
| WO | 2016061389 A3 | 4/2016 |
| WO | 2017009312 A1 | 1/2017 |
| WO | 2017033152 A1 | 3/2017 |
| WO | 2017091512 A1 | 6/2017 |
| WO | 2017176835 A2 | 10/2017 |
| WO | 2017207739 A1 | 12/2017 |
| WO | 2018007817 A1 | 1/2018 |
| WO | 2018039147 A1 | 3/2018 |
| WO | 2018091444 A1 | 5/2018 |
| WO | 2018109058 A1 | 6/2018 |
| WO | 2018111670 A3 | 6/2018 |
| WO | 2018115225 A1 | 6/2018 |
| WO | 2018128454 A1 | 7/2018 |
| WO | 2018128722 A1 | 7/2018 |
| WO | 2018/151821 A1 | 8/2018 |
| WO | 2018151821 A1 | 8/2018 |
| WO | 2018178950 A1 | 10/2018 |
| WO | 2018213440 A1 | 11/2018 |
| WO | 2018237338 A1 | 12/2018 |

OTHER PUBLICATIONS

Almandoz-Gil et al., "Low molar excess of 4-oxo-2-nonenal and 4-hydroxy-2-nonenal promote oligomerization of alpha-synuclein through different pathways," Free Radical Biology and Medicine 110:421-431 (2017).

Anderson et al., "Phosphorylation of Ser-129 is the dominant pathological modification of alpha-synuclein in familial and sporadic Lewy body disease," J Biol Chem 281:29739-29752 (2006).

Assayag et al., "Polyunsaturated fatty acids induce α-synuclein-related pathogenic changes in neuronal cells," Am J Pathology 171(6):2000-2011 (2007).

Baba et al., "Aggregation of alpha-synuclein in Lewy bodies of sporadic Parkinson's disease and dementia with Lewy bodies," Am J Pathology 152(4):879-884 (1998).

Bae et al., "Lipid peroxidation product 4-hydroxy-2-nonenal promotes seeding-capable oligomer formation and cell-to-cell transferor α-synuclein," Antioxid. Redox Signal 18(7):770-783 (2013).

Bengoa-Vergniory et al., "Alpha-synuclein oligomers: a new hope," J. Acta Neuropathol 134:819-838 (2017).

Bergström et al., "Development of Passive Immunotherapies for Synucleinopathies," Movement Disorders 31(2):203-213 (2016).

Bloch et al., "α-Synuclein pathology of the spinal and peripheral autonomic nervous system in neurologically unimpaired elderly subjects," Neuropathology and Applied Neurobiology 32:284-295 (2006).

Bosco et al., "Elevated levels of oxidized cholesterol metabolites in Lewy body disease brains accelerate α-synuclein fibrilization," Nature Chemical Biology 2(5):249-253 (2006).

Cole et al., "Lipid droplet binding and oligomerization properties of the Parkinson's disease protein α-synuclein," JBC 277(8):6344-6352 (2002).

Cole et al., "Metal-catalyzed Oxidation of α-Synuclein Helping to Define the Relationship Between Oligomers, Protofibrils, and Filaments," J Biol Chem 280(10):9678-9690 (2005).

Conway et al., "Accelerated in vitro fibril formation by a mutant α-synuclein linked to early-onset Parkinson disease," Nature Medicine 4(11):1318-1320 (1998).

Cremades et al., "Chapter Three—Structural Characteristics of α-Synuclein Oligomers," International Review of Cell and Molecular Biology 329:79-143 (2017).

Cremades et al., "Direct observation of the interconversion of normal and toxic forms of α-synuclein," Cell 149:1048-1059 (2012).

Croisier et al., "Comparative study of commercially available anti α-synuclein antibodies," Neuropathology and Applied Neurobiology 32:351-356 (2006).

Curtiss et al., "Selection of monoclonal antibodies for linear epitopes of an apolipoprotein yields antibodies with comparable affinity for lipid-free and lipid-associated apolipoprotein," Journal of Lipid Research 37:884-892 (1996).

Danzer et al., "Different species of α-synuclein oligomers induce calcium influx and seeding," J Neuroscience 27(34):9220-9232 (2007).

Deng et al., "Projecting human pharmacokinetics of therapeutic antibodies from nonclinical data. What have we learned?" mAbs 3:1, 61-66; (2011).

Dimitrov et al., "Therapeutic Antibodies: Current State and Future Trends—Is a Paradigm Change Coming Soon?" Meth Mol Biol 525: Chapter 1, pp. 1-27 (2009).

Duda et al., "Immunohistochemical and Biochemical Studies Demonstrate a Distinct Profile of a-Synuclein Permutations in Multiple System Atrophy," Journal of Neuropathology and Experimental Neurology 59:9 830-841 (2000).

El-Agnaf et al., "α-Synuclein implicated in Parkinson's disease is present in extracellular biological fluids, including human plasma," FASEB J 17:1945-1947 (2003).

(56) References Cited

OTHER PUBLICATIONS

Emadi et al., "Inhibiting aggregation of α-synuclein with human single chain antibody fragments," Biochem 43(10):2871-2878 (2004).
Emadi et al., "Isolation of a human single chain antibody fragment against oligomeric α-synuclein that inhibits aggregation and prevents α-synuclein-induced toxicity," J. Mol. Biol. 368(4):1132-1144 (2007).
Fagerqvist et al., "Monoclonal antibodies selective for α-synuclein oligomers/protofibrils recognize brain pathology in Lewy body disorders and α-synuclein transgenic mice with the disease-causing A30P mutation," Journal of Neurochemistry 126:131-144 (2013).
Fairfoul et al., "Alpha-synuclein RT-QuIC in the CSF of patients with alpha-synucleinopathies," Annals of Clinical and Translational Neurology 3(10): 812-818 (2016).
Fernagut et al., "Behavioral and histopathological consequences of paraquat intoxication in mice: Effects of α-synuclein overexpression," Synapse 61(12):991-1001 (2007).
Fjorback et al., "Determination of α-synuclein concentration in human plasma using ELISA," Scandanavian Journal of Clinical & Laboratory Investigation 67:431-435 (2007).
Fujiwara et al., "α-Synuclein is phosphorylated in synucleinopathy lesions," Nat Cell Biol 4: 160-164 (2002).
Games et al., "Reducing C-Terminal-Truncated Alpha-Synuclein by Immunotherapy Attenuates Neurodegeneration and Propagation in Parkinson's Disease-Like Models," J. Neurosci 34(28):9441-9454 (2014).
Garambois et al., "Fully human IgG and IgM antibodies directed against the carcinoembryonic antigen (CEA) Gold 4 epitope and designed for radioimmunotherapy (RIT) of colorectal cancers," BMC Cancer 4:75 (2004).
George et al., "Characterization of a novel protein regulated during the critical period for song learning in the zebra finch," Neuron 15:361-372 (1995).
Giasson et al., "A panel of epitope-specific antibodies detects protein domains distributed throughout human α-synuclein in lewy bodies of Parkinson's disease," J Neurosci Res 59:528-533 (2000).
Goedert, "α-synuclein and neurodegenerative diseases," Nature Reviews Neuroscience 2:491-501 (2001).
Gomez-Tortosa et al., "α-Synuclein immunoreactivity in dementia with Lewy bodies: morphological staging and comparison with ubiquitin immunostaining," Acta Neuropathologica 99(4):352-357 (2000).
Guilliams et al., "Nanobodies raised against monomeric alpha-synuclein distinguish between fibrils at different maturation stages," JMB 425:2397-2411 (2013).
Jakes et al., "Epitope mapping of LB509, a monoclonal antibody directed against human a-synuclein," Neuroscience Letters 269:13-16 (1999).
Jakobovits, "A Production of fully human antibodies by transgenic mice," Current Opinion in Biotechnology 6:561-566 (1995).
Jankovic et al., "Safety and Tolerability of Multiple Ascending Doses of PRX002/RG7935, an Anti-α-Synuclein Monoclonal Antibody, in Patients with Parkinson Disease. A Randomized Clinical Trial," JAMA Neurol. 75(10):1206-1214 (2018).
Jensen et al., "α-Synuclein binds to tau and stimulates the protein kinase A-catalyzed tau phosphorylation of serine residues 262 and 356," J. Biol. Chem 274(36):25481-25489 (1999).
Jensen et al., "Microtubule-associated protein 1B is a component of cortical Lewy bodies and binds α-synuclein filaments," JBC 275(28):21500-21507 (2000).
Kahle et al., "Physiology and pathophysiology of alpha-synuclein. Cell culture and transgenic animal models based on a Parkinson's disease-associated protein," Ann N Y Acad Sci 920:33-41 (2000).
Kahle et al., "Subcellular Localization of Wild-Type and Parkinson's Disease-Associated Mutant a-Synuclein in Human and Transgenic Mouse Brain," J. Neuroscience 20(17):6365-6373 (2000).
Kawamata et al., "Interaction of α-synuclein and synphilin-1: effect of Parkinson's disease-associated mutations," J. Neurochem. 77:929-934 (2001).
Kayed et al., "Common structure of soluble amyloid oligomers implies common mechanism of pathogenesis," Science 300:486-489 (2003).
Klos et al., "α-Synuclein pathology in the spinal cords of neurologically asymptomatic aged individuals," Neurology 66:1100-1102 (2006).
Kramer et al., "Presynaptic alpha-Synuclein Aggregates, Not Lewy Bodies, Cause Neurodegeneration in Dementia with Lewy Bodies," J. Neuroscience 27(6):1405-1410 (2007).
Kunik et al., "Structural Consensus among Antibodies defines the antigen binding site," PLoS Comput Biol 8(2) (2012).
Lee et al., "Characterization of Cytoplasmic alpha-Synuclein Aggregates," J Biol Chem 277(50):48976-48983 (2002).
Lee et al., "Intravesicular localization and exocytosis of α-synuclein and its aggregates," J. Neuroscience 25(25):6016-6024 (2005).
Lee et al., "Real-time analysis of amyloid fibril formation of α-synuclein using a fibrillation-state-specific fluorescent probe of JC-1," Biochem J 418:311-323 (2009).
Lipman et al., "Monoclonal versus polyclonal antibodies: distinguishing characteristics, applications, and information resources," ILAR Journal 46:258-268 (2005).
Maguire-Zeiss et al., "Identification of human α-synuclein specific single chain antibodies," Biochem Biophys Res Comm 349:1198-1205 (2006).
Margutti et al., "Autoantibodies to the C-terminal subunit of RLIP76 induce oxidative stress and endothelial cell apoptosis in immune-mediated vascular diseases and atherosclerosis," Blood 111(9):4559-4570 (2007).
Masliah et al., "Effects of α-synuclein immunization in a mouse model of Parkinson's disease," Neuron 46:857-868 (2005).
Masliah et al., "Passive Immunization Reduces Behavioral and Neuropathological Deficits in an Alpha-Synuclein Transgenic Model of Lewy Body Disease," PLoS One 4:1-17 (2011).
McLean et al., "Membrane Association and Protein Conformation of α-Synuclein in Intact Neurons Effect of Parkinson' s Disease-Linked Mutations," J. Biol. Chem 275(12):8812-8816 (2000).
Miller et al., "α-Synuclein in blood and brain from familial Parkinson disease with SNCA locus triplication," Neurology 62:1835-1838 (2004).
Milne et al., "Heat-Labile Antigens of *Salmonella enteritidis* I. Extraction of Antigens," J Bacterial. 92(3):543-548 (1966).
Näsström et al., "P4-284: Oligomeric amorphous species of alpha-synuclein induce toxicity in a cellular model," Alzh Dem: J Alzh Assoc 4(4):T754 (2008).
Näsström et al., "The lipid peroxidation metabolite 4-oxo-2-nonenal cross-links α-synuclein causing rapid formation of stable oligomers," Biochem. Biophys. Res. Comm. 378:872-876 (2009).
Näsström et al., "Antibodies against α-synuclein reduce oligomerization in living cells," PLoS ONE 6(10):e27230 (2011).
Okochi et al., "Constitutive phosphorylation of the Parkinson's disease associated alpha-synuclein," J Biol Chem 275: 390-397 (2000).
Olanow et al., "Parkinson's Disease and Alpha Synuclein: Is Parkinson's Disease a Prion-Like Disorder?" Movement Disorders 28(1):31-40 (2013).
Oueslati, "Implication of Alpha-Synuclein Phosphorylation at S129 in Synucleinopathies: What Have We Learned in the Last Decade?" Journal of Parkinson's Disease 6:39-51 (2016).
Perez De La Lastra et al., "Epitope mapping of 10 monoclonal antibodies against the pig analogue of human membrane cofactor protein (MCP)," Immunology 96(4):663-670 (1999).
Qin et al., "Effect of 4-hydroxy-2-nonenal modification on α-synuclein aggregation," J Biol Chem 282(8):5862-5870 (2007).
Reichmann et al., "Reshaping human antibodies for therapy," Nature 332:323-327 (1988).
Ruesink et al., "Stabilization of α-synuclein oligomers using formaldehyde," PLoS ONE 14(10): e0216764 (2019).
Schenk et al., "First in human assessment of PRX002, an anti-alpha-synuclein monoclonal antibody, in healthy volunteers," Movement Disorders 32(2):211-218 (2017).
Schneider et al., "Over-expression of alpha-synuclein in human neural progenitors Teads to specific changes in fate and differentiation," Human Molecular Genetics 16(6):651-666 (2007).

(56) References Cited

OTHER PUBLICATIONS

Seo et al., "α-Synuclein regulates neuronal survival via Bcl-2 family expression and PI3/Akt kinase pathway," FASEB J 16(13): 1826-1828 (2002).
Serpell et al., "Fiber diffraction of synthetic α-synuclein filaments shows amyloid-like cross-β conformation," PNAS 97(9):4897-4902 (2000).
Shamoto-Nagai et al., "In parkinsonian substantia nigra, α-synuclein is modified by acrolein, a lipid-peroxidation product, and accumulates in the dopamine neurons with inhibition of proteasome activity," J Neural Transm 114:1559-1567 (2007).
Sharma et al., "A close association of torsinA and α-synuclein in lewy bodies: a fluorescence resonance energy transfer study," American J. Pathology 159(1):339-344 (2001).
Sharon et al., "The Formation of Highly Soluble Oligomers of alpha-Synuclein Is Regulated by Fatty Acids and Enhanced in Parkinson's Disease," Neuron 37:583-595 (2003).
Souza et al., "Dityrosine Cross-linking Promotes Formation of Stable a-Synuclein Polymers," JBC 275:24 18344-18349 (2000).
Stefanis, "A-Synuclein in Parkinson's Disease," Cold Spring Harb Perspect Med 4:a009399 (2012).
Tickle et al., "A fully automated primary screening system for the discovery of therapeutic antibodies directly from B cells," J Biomol Screen 20(4):492-497 (2015).
Toyokuni et al., "The monoclonal antibody specific for the 4-hydroxy-2-nonenal histidine adduct," FEBS Letters 359:189-191 (1995).
Tran et al., "α-Synuclein Immunotherapy Blocks Uptake and Templated Propagation of Misfolded alpha-Synuclein and Neurodegeneration," Cell Reports 7(6):2054-2065 (2014).
Trostchansky et al., "Interaction with phospholipids modulates α-synuclein nitration and lipid-protein adduct formation," Biochem. J. 393: 343-349 (2006).
Vaikath et al., "Generation and Characterization of novel conformation-specific monoclonal antibodies for alpha-synuclein pathology," Neurobiology of Disease 79: 81-99 (2015).
Van Der Putten et al., "Neuropathology in mice expressing human α-synuclein," J. Neuroscience 20(16):6021-6029 (2000).
Van Diggelen et al., "Two conformationally distinct α-synuclein oligomers share common epitopes and the ability to impair long-term potentiation," PLoS ONE 14(3):e0213663 (2019).
Visanji et al., "α-Synuclein-Based Animal Models of Parkinson's Disease: Challenges and Opportunities in a New Era," Trends in Neurosciences, 39(11) 750-762 (2016).
Vogiatzi et al., "Wild type α-synuclein is degraded by chaperone-mediated autophagy and macroautophagy in neuronal cells," JBC 283(35):23542-23556 (2008).
Volpicelli-Daley et al., "Exogenous a-Synuclein Fibrils Induce Lewy Body Pathology Leading to Synaptic Dysfunction and Neuron Death," Neuron 72, 57-71 (2011).
Wahlberg et al., "Development of oligomer-specific alpha-synuclein antibodies," Alzheimer's & Dementia 4(4) Suppl. T481-T482, p. 2-372 (2008).
Weber et al., "From rabbit antibody repertoires to rabbit monoclonal antibodies," Experimental and Molecular Medicine 49: e305 (2017).
Yamashita et al., "Recent advances in the generation of human monoclonal Antibody," Cytotechnology 55:55-60 (2007).
Information on H3C Ab from U Iowa—D2 in Opposition of EP 2282758 submitted Aug. 16, 2019.
Datasheet for the 211 antibody—D14 in Opposition of EP 2282758 submitted Aug. 16, 2019.
Cosmo Bio News Topics Digest 2004—D17 in Opposition of EP 2282758 submitted Aug. 16, 2019.
Webpage for 610787 antibody—D20 in Opposition of EP 2282758 submitted Aug. 16, 2019.
Datasheet for 610787 antibody—D21 in Opposition of EP 2282758 submitted Aug. 16, 2019.
Screenshot for MAB3249 antibody—D29 in Opposition of EP 2282758 submitted Aug. 16, 2019.
MAb3249 Datasheet—D30 in Opposition of EP 2282758 submitted Aug. 16, 2019.
Screenshot for ab48506 antibody—D33 in Opposition of EP 2282758 submitted Aug. 16, 2019.
Screenshot of HNEJ-2 antibody—D34 in Opposition of EP 2282758 submitted Aug. 16, 2019.
Asano thesis 2007 Marshall University—D36 in Opposition of EP 2282758 submitted Aug. 16, 2019.
Experimental report for 8A5 antibody—D40 in Opposition of EP 2282758 submitted Aug. 16, 2019.
Product sheet for 8A5 producing cell line—D41 in Opposition of EP 2282758 submitted Aug. 16, 2019.
Patentee's letter of Jul. 9, 2014 re EP2539366—D45 in Opposition of EP 2282758 submitted Aug. 16, 2019.
Technical Report—Binding data of anti-alpha synuclein antibodies—D1 in Opposition of EP 2282758 submitted Aug. 21, 2019.
Tocris—Datasheet for DHA—D6 in Opposition of EP 2282758 submitted Aug. 21, 2019.
Exhibit 1 submitted by patentee Feb. 27, 2018—D12 in Opposition of EP 2282758 submitted Aug. 21, 2019.
EP Appl. No. 08022188—priority to WO2010069603—E6 in Opposition of EP 2282758 submitted Aug. 21, 2019.
Letter dated Mar. 14, 2017—D1 in Opposition of EP3067066 submitted Dec. 24, 2019.
Letter dated Jan. 8, 2018 filed during examination—D2 in Opposition of EP 3067066 submitted Dec. 24, 2019.
Letter dated Jul. 30, 2018 filed during examination—D3 in Opposition of EP 3067066 submitted Dec. 24, 2019.
Letter dated Aug. 24, 2018 filed during examination—D4 in Opposition of EP 3067066 submitted Dec. 24, 2019.
Response filed May 31, 2011 in U.S. Appl. No. 12/037,081—D5 in Opposition of EP 3067066 submitted Dec. 24, 2019.
ATCC deposit receipt for antibody 9E4 dated Feb. 26, 2007—D6 in Opposition of EP 3067066 submitted Dec. 24, 2019.
Declaration of E Masliah filed in U.S. Appl. No. 11/710,248—D27 in Opposition of EP 3067066 submitted Jun. 8, 2020.
Kunik et al., "Structural Consensus among Antibodies Defines the Antigen Binding Site," PLoS Computational Biology 8(2): e1002388 (2012).
Schenk et al., "First-in-Human Assessment of PRX001, an Anti-[alpha] Synuclein Monoclonal Antibody, in Healthy Volunteers," Movement Disorders 32(2): 211-218 (2017).
Weber et al., "From Rabbit Antibody Repertoires to Rabbit Monoclonal Antibodies," Experimental & Molecular Medicine 49: e305 (2017).
The International Search Report issued in PCT/EP2018/084697 dated Feb. 19, 2019.
Declaration of Leda Alfonso Trujillo filed in Ecuador Application SENADI-2020-39610, mailed May 5, 2021.
Declaration of Leda Alfonso Trujillo filed in Ecuador Application SENADI-2020-39623, mailed May 5, 2021.
Dehay et al., "Targeting α-synuclein fortreating Parkinson's disease: mechanistic and therapeutic considerations," Lancet Neurol. 14(8):855-866 (2015).
Kim et al., "Transneuronal Propagation of Pathologic α-Synuclein from the Gut to the Brain Models Parkinson's Disease," Neuron. 103(4):627-641 (2019).
Shen et al., "Identifying the Pathological Domain of Alpha-Synuclein as a Therapeutic for Parkinson's Disease," Int J Mol Sci. 20(9):2338 (2019).
Sumikura et al., "Distribution of α-synuclein in the spinal cord and dorsal root ganglia in an autopsy cohort of elderly persons," Acta neuropathologica communications 3(1):1-11 (2015).
Non-final Office Action in U.S. Appl. No. 16/772,043 dated Jul. 7, 2021.

* cited by examiner

ANTI-ALPHA-SYNUCLEIN ANTIBODIES

REFERENCE TO AN ELECTRONIC SEQUENCE LISTING

The contents of the electronic sequence listing (0089-0027US1_SL.txt; Size: 60.0 KB; and Date of Creation Jun. 10, 2020) is herein incorporated by reference in its entirety.

FIELD OF THE INVENTION

The present invention relates to anti-alpha synuclein antibodies and method of using the same to treat synucleinopathies. In particular, the present invention relates to anti-human alpha synuclein antibodies and their use in the treatment of Parkinson's Disease.

BACKGROUND OF THE INVENTION

Alpha synuclein is a small soluble 140 amino acid long protein existing in radically different forms. Alpha synuclein is mainly found in pre-synaptic nerve terminals and although its precise function is unknown researchers believe it plays a central role in multiple neurodegenerative processes.

Over the past 15 years, alpha synuclein has been shown to play a key role in the pathogenesis of all forms of Parkinson's disease. Genetic mutations or gene multiplications of the alpha synuclein gene cause familial early onset Parkinson's disease (PD). Interestingly in gene locus multiplication families, the pathogenic effect is clearly dependent on the gene dosage. Gene duplications cause a relatively early onset form of PD (~47 years old) which has a normal disease course, while gene triplications are associated with a very early age of onset (~33 years old) and a very rapid disease course. In all forms of Parkinson's disease alpha synuclein is the main constituent of Lewy bodies, the key pathological hallmark of the disease.

Lewy body pathology expands during the course of the disease and it is proposed that alpha synuclein acts as a prion like protein, which misfolds to form toxic oligomers and aggregates that can spread from affected to unaffected neurons (Olanow C. W et al. Movement Disorders, Vol 28, No. 1, 2013). Current existing therapies are not capable of stopping the disease spreading and only aid the treatment of the symptoms associated with the progressive loss of motor-neurons dependent activities. In 2014, Tran H. T. et al. (Tran H. T. et al, Cell Reports 7, 2054-2065, 2014) showed that intraperitoneal administration of a monoclonal antibody for misfolded alpha synuclein to mice previously injected intrastriatally with alpha synuclein preformed fibrils reduced the Lewy bodies pathology, ameliorated substantia nigra dopaminergic neuron loss and improved motor impairments. Hence, there still remains the need of a passive immune-therapy that could exert therapeutic effects in PD and other alpha synucleinopathies.

SUMMARY OF THE INVENTION

The present invention addresses the above-identified need by providing anti-alpha synuclein antibodies according to the following embodiments.

Embodiment 1: An antibody or antigen-binding fragment thereof which binds to alpha synuclein, wherein the antibody comprises:
a. a light chain variable region comprising:
  i. a CDR-L1 comprising SEQ ID NO: 44;
  ii. a CDR-L2 comprising SEQ ID NO: 2 and
  iii. a CDR-L3 comprising SEQ ID NO: 3; and
b. a heavy chain variable region comprising:
  i. a CDR-H1 comprising SEQ ID NO: 4;
  ii. a CDR-H2 comprising SEQ ID NO: 45 and
  iii. a CDR-H3 comprising SEQ ID NO: 46.

Embodiment 2: The antibody or antigen-binding fragment thereof according to embodiment 1, which binds to alpha synuclein to an epitope comprising, with reference to SEQ ID NO: 10, residues E123, Y125, E126, M127, P128, S129, E130 and E131; wherein the epitope optionally comprises A124 and G132.

Embodiment 3: The antibody or antigen-binding fragment thereof according to any one of claim 1 or 2, wherein the antibody or antigen-binding fragment prevents aggregation of alpha synuclein induced by alpha synuclein fibrils.

Embodiment 4: The antibody or antigen-binding fragment thereof according to any one of embodiments 1 to 3, wherein the antibody or antigen-binding fragment thereof is capable of binding alpha synuclein as a monomer and in fibrils.

Embodiment 5: The antibody or antigen-binding fragment thereof according to any one of the preceding embodiments which has a higher binding affinity for alpha synuclein in fibrils compared to alpha synuclein as monomer characterized by a constant of dissociation ($K_D$) at least 10-fold higher for monomeric alpha synuclein than for alpha synuclein in fibrils.

Embodiment 6: The antibody or antigen-binding fragment thereof according to any one of the preceding embodiments which has a ($K_D$) for alpha synuclein in fibrils of 300 pM or less.

Embodiment 7: The antibody or antigen-binding fragment thereof according to any one of the preceding embodiments which does not bind beta synuclein and/or gamma synuclein.

Embodiment 8: The antibody or antigen-binding fragment thereof according to any one of the preceding embodiments wherein the antibody is a chimeric, humanized or human antibody.

Embodiment 9: The antibody according to any one of the preceding embodiments, wherein the antibody is a full-length antibody.

Embodiment 10: The antibody according to embodiment 9, wherein the full-length antibody is selected from an IgG1, IgG4 or IgG4P.

Embodiment 11: The antigen-binding fragment thereof according to any one of the embodiments 1 to 8, wherein the antigen-binding fragment is selected from a Fab, a Fab', a F(ab')$_2$, a scFv, a dAb or a $V_{HH}$.

Embodiment 12: The antibody or antigen-binding fragment thereof according to any one of the preceding claims wherein the antibody or antigen-binding fragment thereof comprises:
a. a light chain variable region comprising a CDR-L1 comprising SEQ ID NO: 1; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
b. a light chain variable region comprising SEQ ID NO: 15 and a heavy chain variable region comprising SEQ ID NO: 31; or
c. a light chain comprising SEQ ID NO: 17 and a heavy chain comprising SEQ ID SEQ ID NO: 33.

Embodiment 13: The antibody or antigen-binding fragment thereof according to claim any one of claims 1 to 11, wherein the antibody or antigen-binding fragment thereof comprises:
  a. a light chain variable region comprising a CDR-L1 comprising SEQ ID NO: 1; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
  b. a light chain variable region comprising SEQ ID NO: 15 and a heavy chain variable region comprising SEQ ID NO: 23; or
  c. a light chain comprising SEQ ID NO: 17 and a heavy chain comprising SEQ ID SEQ ID NO: 25.

Embodiment 14: The antibody or antigen-binding fragment thereof according to any one of claims 1 to 11 wherein the antibody or antigen-binding fragment thereof comprises:
  a. a light chain variable region comprising a CDR-L1 comprising SEQ ID NO: 1; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 8 and a CDR-H3 comprising SEQ ID NO: 9; or
  b. a light chain variable region comprising SEQ ID NO: 15 and a heavy chain variable region comprising SEQ ID NO: 27 or 35; or
  c. a light chain comprising SEQ ID NO: 17 and a heavy chain comprising SEQ ID SEQ ID NO: 29 or 37.

Embodiment 15: The antibody or antigen-binding fragment thereof according to any one of claims 1 to 11 wherein the antibody or antigen-binding fragment thereof comprises:
  a. a light chain variable region comprising a CDR-L1 comprising SEQ ID NO: 7; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
  b. a light chain variable region comprising SEQ ID NO: 19 and a heavy chain variable region comprising SEQ ID NO: 23 or 31; or
  c. a light chain comprising SEQ ID NO: 21 and a heavy chain comprising SEQ ID SEQ ID NO: 25 or 33.

Embodiment 16: The antibody or antigen-binding fragment thereof according to any one of claims 1 to 11, wherein the antibody or antigen-binding fragment thereof comprises:
  a. a light chain variable region comprising a CDR-L1 comprising SEQ ID NO: 7; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 8 and a CDR-H3 comprising SEQ ID NO: 9; or
  b. a light chain variable region comprising SEQ ID NO: 19 and a heavy chain variable region comprising SEQ ID NO: 27 or 35; or
  c. a light chain comprising SEQ ID NO: 21 and a heavy chain comprising SEQ ID SEQ ID NO: 29 or 37.

Embodiment 17: An antibody or antigen-binding fragment thereof which:
  a. Competes for binding alpha synuclein with the antibody or antigen-binding fragment thereof according to any one of the preceding claims; and/or
  b. cross-blocks or is cross-blocked by the antibody or antigen-binding fragment thereof according to any one of the preceding claims for binding alpha synuclein; and/or
  c. binds alpha synuclein to the same epitope as the antibody or antigen-binding fragment thereof according to any one of the preceding claims; and/or
  d. comprises a heavy chain variable region having at least 80% identity or similarity to the sequence according to SEQ ID NO: 23, SEQ ID NO: 31, SEQ ID NO: 27 or SEQ ID NO: 35; and/or
  e. comprises a light chain variable region having at least 80% identity or similarity to the sequence according to SEQ ID NO: 15 or SEQ ID NO: 19.

Embodiment 18: An isolated polynucleotide encoding the antibody or antigen-binding fragment thereof according to any one of embodiments 1 to 16.

Embodiment 19: The isolated polynucleotide according to embodiment 18, wherein the polynucleotide encodes:
  a. a light chain variable region, wherein the polynucleotide:
    i. is at least 90% identical to SEQ ID NO: 16 or SEQ ID NO: 20; or
    ii. comprises SEQ ID NO: 16 or 20; or
    iii. consists essentially of SEQ ID NO: 16 or SEQ ID NO: 20;
  b. a heavy chain variable region, wherein the polynucleotide:
    i. is at least 90% identical to SEQ ID NO: 24 or SEQ ID NO: 28 or SEQ ID NO: 32 or SEQ ID NO: 36; or
    ii. comprises SEQ ID NO: 24 or SEQ ID NO: 28 or SEQ ID NO: 32 or SEQ ID NO: 36; or
    iii. consists essentially of SEQ ID NO: 24 or SEQ ID NO: 28 or SEQ ID NO: 32 or SEQ ID NO: 36;
  c. a light chain, wherein the polynucleotide:
    i. is at least 90% identical to SEQ ID NO: 18 or SEQ ID NO: 22; or
    ii. comprises SEQ ID NO: 18 or 22; or
    iii. consists essentially of SEQ ID NO: 18 or SEQ ID NO: 22;
  d. a heavy chain, wherein the polynucleotide:
    i. is at least 90% identical to SEQ ID NO: 26 or SEQ ID NO: 30 or SEQ ID NO: 34 or SEQ ID NO: 38; or
    ii. comprises SEQ ID NO: 26 or SEQ ID NO: 30 or SEQ ID NO: 34 or SEQ ID NO: 38; or
    iii. consists essentially of SEQ ID NO: 26 or SEQ ID NO: 30 or SEQ ID NO: 34 or SEQ ID NO: 38.

Embodiment 20: A cloning or expression vector comprising one or more polynucleotides according to any one of embodiments 18 or 19.

Embodiment 21: A host cell comprising:
  a. one or more polynucleotides according to any one of embodiments 18 or 19 or
  b. one or more expression vectors according to embodiment 20.

Embodiment 22: A process for the production of an antibody or antigen-binding fragment thereof according to any one of embodiments 1 to 17, comprising culturing the host cell according to embodiment 21 under suitable conditions for producing the antibody or antigen-binding fragment thereof and isolating the antibody or antigen-binding fragment thereof.

Embodiment 23: A pharmaceutical composition comprising the antibody or antigen-binding fragment thereof according to any one of embodiments 1 to 17 and one or more pharmaceutically acceptable carriers, excipients or diluents.

Embodiment 24: The antibody or antigen-binding fragment thereof according to any one of embodiments 1 to 17 or the pharmaceutical composition according to embodiment 23 for use in therapy.

Embodiment 25: The antibody or antigen-binding fragment thereof according to any one of embodiments 1 to 17 or the pharmaceutical composition according to embodiment 23 for use in the treatment of one or more synucleinopathies.

Embodiment 26: The antibody or antigen-binding fragment thereof of use according to embodiment 25 wherein the synucleinopathies is selected from Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1).

Embodiment 27: The antibody or antigen-binding fragment thereof of use according to embodiment 26 wherein the synucleinopathy is Parkinson's disease.

Embodiment 28: A method of treating a synucleinopathy in a patient comprising administering to said patient a therapeutically effective amount of an antibody or antigen-binding fragment thereof according to any one of embodiments 1 to 17 or the pharmaceutical composition according to embodiment 23.

Embodiment 29: The method according to embodiment 29 wherein the synucleinopathy is selected from Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), preferably Parkinson's disease.

Embodiment 30: The antibody or antigen-binding fragment thereof according to any one of embodiments 1 to 16 for use in the diagnosis of alpha synucleinopathies, preferably in the diagnosis of Parkinson's disease.

DETAILED DESCRIPTION OF THE INVENTION

Figure 1A:
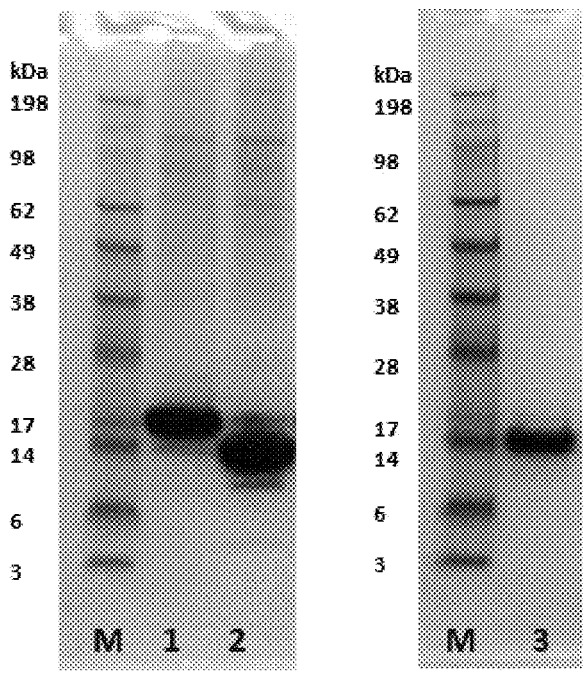
FIGS. 1A and 1B. (A) SDS-PAGE of samples of alpha synuclein expression. Alpha synuclein with His tag (1) and after removal of His tag by TEV protease (2), Superdex 75 size exclusion chromatography on the TEV protease treated human alpha-synuclein (3). Protein molecular weight marker SeeBluePlus2 (Invitrogen) (M). (B) SDS-PAGE of human alpha-synuclein purified from Expi293 supernatant as wildtype untagged protein (4) Protein molecular weight marker SeeBluePlus2 (Invitrogen) (M).

The present disclosure will now be described with respect to particular non-limiting aspects and embodiments thereof and with reference to certain figures and examples.

Technical terms are used by their common sense unless indicated otherwise. If a specific meaning is conveyed to certain terms, definitions of terms will be given in the context of which the terms are used.

Where the term "comprising" is used in the present description and claims, it does not exclude other elements. For the purposes of the present disclosure, the term "consisting of" is considered to be a preferred embodiment of the term "comprising of".

Where an indefinite or definite article is used when referring to a singular noun, e.g. "a", "an" or "the", this includes a plural of that noun unless something else is specifically stated.

As used herein, the terms "treatment", "treating" and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. Treatment thus covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A "therapeutically effective amount" refers to the amount of an anti-alpha synuclein antibody or antigen-binding fragment thereof that, when administered to a mammal or other subject for treating a disease, is sufficient to produce such treatment for the disease. The therapeutically effective amount will vary depending on the anti-alpha synuclein antibody or antigen-binding fragment thereof, the disease and its severity and the age, weight, etc., of the subject to be treated.

The term "isolated" means, throughout this specification, that the antibody, antigen-binding fragment or polynucleotide, as the case may be, exists in a physical milieu distinct from that in which it may occur in nature. The present invention provides for an antibody or antigen-binding fragment thereof which binds to alpha synuclein, wherein the antibody comprises:

a. a light chain variable region comprising:
  i. a CDR-L1 comprising SEQ ID NO: 44;
  ii. a CDR-L2 comprising SEQ ID NO: 2 and
  iii. a CDR-L3 comprising SEQ ID NO: 3; and
b. a heavy chain variable region comprising:
  iv. a CDR-H1 comprising SEQ ID NO: 4;
  v. a CDR-H2 comprising SEQ ID NO: 45 and
  vi. a CDR-H3 comprising SEQ ID NO: 46.

In SEQ ID NO: 44, Xaa is asparagine (Asn; N) or arginine (Arg; R). Independently, in SEQ ID NO: 45, Xaa is serine (Ser; S) or asparagine (Asn N) and in SEQ ID NO: 46, Xaa is asparagine (Asn N) or histidine (His; H).

In one embodiment, Xaa in SEQ ID NO: 44 and 46 is asparagine and Xaa in SEQ ID NO: 45 is serine.

In one embodiment, the antibody or antigen-binding fragment thereof which binds to alpha synuclein, wherein the antibody comprises:

a. a light chain variable region comprising:
  i. a CDR-L1 comprising SEQ ID NO: 1;
  ii. a CDR-L2 comprising SEQ ID NO: 2 and
  iii. a CDR-L3 comprising SEQ ID NO: 3; and
b. a heavy chain variable region comprising:
  iv. a CDR-H1 comprising SEQ ID NO: 4;
  v. a CDR-H2 comprising SEQ ID NO: 5 and
  vi. a CDR-H3 comprising SEQ ID NO: 6.

Alpha synuclein (or alpha syn; a-synuclein; a-syn or any other known synonym) refers to the general name of this protein and includes, without being limited to, alternative splicing variants, mutants and alpha synuclein from other species (mouse, monkey, etc.). Unless otherwise specified, when human alpha synuclein is intended or explicitly mentioned, such alpha synuclein comprises the sequence given in SEQ ID NO: 10 or in Uniprot P37840.

The term 'antibody' as used herein generally relates to intact (whole) antibodies i.e. comprising the elements of two heavy chains and two light chains. The antibody may comprise further additional binding domains for example as per the molecule DVD-Ig as disclosed in WO 2007/024715, or the so-called (FabFv)$_2$Fc described in WO2011/030107. Thus, antibody as employed herein includes bi, tri or tetra-valent full-length antibodies.

Antigen-binding fragments of antibodies include single chain antibodies (i.e. a full length heavy chain and light chain); Fab, modified Fab, Fab', modified Fab', F(ab')$_2$, Fv, Fab-Fv, Fab-dsFv, single domain antibodies (e.g. $V_H$ or $V_L$ or $V_{HH}$), scFv, bi, tri or tetra-valent antibodies, Bis-scFv, diabodies, tribodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilized versions thereof, the Fab-dsFv, was first disclosed in WO2010/035012. Other antibody fragments for use in the present invention include the Fab and Fab' fragments described in International patent applications WO2005/003169, WO2005/003170 and WO2005/003171. Multi-valent antibodies may comprise multiple specificities e.g. bispecific or may be monospecific (see for example WO 92/22583 and WO05/113605). One such example of the latter is a Tri-Fab (or TFM) as described in WO92/22583.

An alternative antigen-binding fragment comprises a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in International Patent Application Publication No, WO2015/197772, which is hereby incorporated by reference in its entirety and particularly with respect to the discussion of antibody fragments.

A typical Fab' molecule comprises a heavy and a light chain pair in which the heavy chain comprises a variable region VH, a constant domain CH1 and a natural or modified hinge region and the light chain comprises a variable region VL and a constant domain CL. Dimers of a Fab' according to the present disclosure create a F(ab')$_2$ where, for example, dimerization may be through the hinge.

The antibody or antigen-binding fragment thereof according to the present invention binds to an epitope of alpha synuclein.

In one embodiment, the antibody or antigen-binding fragment thereof comprises:
a. a light chain variable region comprising:
i. a CDR-L1 comprising SEQ ID NO: 44;
ii. a CDR-L2 comprising SEQ ID NO: 2 and
iii. a CDR-L3 comprising SEQ ID NO: 3; and
b. a heavy chain variable region comprising:
iv. a CDR-H1 comprising SEQ ID NO: 4;
v. a CDR-H2 comprising SEQ ID NO: 45 and
vi. a CDR-H3 comprising SEQ ID NO: 46 and binds to alpha synuclein to an epitope comprising, with reference to SEQ ID NO: 10, residues E123, Y125, E126, M127, P128, S129, E130 and E131, wherein the epitope optionally comprises A124 and G132.

In SEQ ID NO: 44, Xaa is asparagine (Asn; N) or arginine (Arg; R). Independently, in SEQ ID NO: 45, Xaa is serine (Ser; S) or asparagine (Asn N) and in SEQ ID NO: 46, Xaa is asparagine (Asn N) or histidine (His; H).

In one embodiment, Xaa in SEQ ID NO: 44 and 46 is asparagine and Xaa in SEQ ID NO: 45 is serine.

In one embodiment, the antibody or antigen-binding fragment thereof which binds to alpha synuclein comprises:
a. a light chain variable region comprising:
i. a CDR-L1 comprising SEQ ID NO: 1;
ii. a CDR-L2 comprising SEQ ID NO: 2 and
iii. a CDR-L3 comprising SEQ ID NO: 3; and
b. a heavy chain variable region comprising:
iv. a CDR-H1 comprising SEQ ID NO: 4;
v. a CDR-H2 comprising SEQ ID NO: 5 and
vi. a CDR-H3 comprising SEQ ID NO: 6 and binds to alpha synuclein to an epitope comprising, with reference to SEQ ID NO: 10, residues E123, Y125, E126, M127, P128, S129, E130 and E131, wherein the epitope optionally comprises A124 and G132.

Within the present invention, the term "epitope" is used interchangeably for both conformational and linear epitopes, where a conformational epitope is composed of discontinued sections of the antigen's amino acid primary sequence and a linear epitope is formed by a sequence formed by continuous amino acids.

The epitope can be identified by any suitable epitope mapping method known in the art in combination with any one of the antibodies provided by the present invention. Examples of such methods include screening peptides of varying lengths derived from full length alpha synuclein for binding to the antibody or fragment thereof of the present invention and identify the smallest fragment that can specifically bind to the antibody containing the sequence of the epitope recognized by the antibody. Alpha synuclein peptides may be produced synthetically or by proteolytic digestion of the alpha synuclein protein. Peptides that bind the antibody can be identified by, for example, mass spectrometric analysis. In another example, NMR spectroscopy or X-ray crystallography can be used to identify the epitope bound by an antibody of the present invention. Typically, when the epitope determination is performed by X-ray crystallography, amino acid residues of the antigen within 4 Å from CDRs are considered to be amino acid residues part of the epitope. Once identified, the epitope may serve for preparing fragments which bind an antibody of the present invention and, if required, used as an immunogen to obtain additional antibodies which bind the same epitope.

In one embodiment the epitope of the antibody or antigen-binding fragment thereof is determined by X-ray crystallography using an alpha synuclein peptide comprising residues 123 to 132 with reference to SEQ ID NO: 10.

Preferably, the antibody or antigen-binding fragment thereof according to the present invention prevents alpha synuclein aggregation induced by alpha synuclein fibrils.

Within this specific context, the term "prevent" (and grammatical variations thereof) is used herein interchangeably with the term "inhibit" and indicates the effect the antibodies according to the present invention have with respect to alpha synuclein aggregation induced by alpha synuclein fibrils. The effect may be prophylactic in terms of completely or partially preventing the aggregation; or completely or partially reducing, i.e. blocking aggregation that has already commenced from further progressing, or completely or partially reducing the occurrence of further aggregation; or completely or partially reversing aggregation which has already occurred.

Without wishing to be bound by theory it is believed that the antibody or antigen-binding fragment thereof according to the present invention binds to alpha synuclein:
i) in monomeric form and prevents alpha synuclein to form oligomers and aggregates; and/or
ii) in oligomeric and fibrillar form and prevents alpha synuclein to spread from neuron to neuron and/or
iii) in oligomeric and/or fibrillar form and prevents alpha synuclein aggregation induced by alpha synuclein fibrils, preferably endogenous alpha synuclein aggregation.

The term "fibrils", "fibrillar form" or "in fibrils" as used herein with respect to alpha synuclein is meant to refer to non-monomeric forms of alpha synuclein, including alpha synuclein oligomers, which may constitute the spreading species within and between brain structures.

Therefore, in one embodiment, the antibody or antigen-binding fragment thereof binds alpha synuclein and comprises:
a. a light chain variable region comprising:
i. a CDR-L1 comprising SEQ ID NO: 44;
ii. a CDR-L2 comprising SEQ ID NO: 2 and
iii. a CDR-L3 comprising SEQ ID NO: 3; and
b. a heavy chain variable region comprising:
iv. a CDR-H1 comprising SEQ ID NO: 4;
v. a CDR-H2 comprising SEQ ID NO: 45 and
vi. a CDR-H3 comprising SEQ ID NO: 46 prevents alpha synuclein aggregation induced by alpha synuclein fibrils. Preferably, the antibody or antigen-binding fragment thereof binds to alpha synuclein to an epitope comprising, with reference to SEQ ID NO: 10, residues E123, Y125, E126, M127, P128, S129, E130 and E131, wherein the epitope optionally comprises A124 and G132.

In SEQ ID NO: 44, Xaa is asparagine (Asn; N) or arginine (Arg; R). Independently, in SEQ ID NO: 45, Xaa is serine (Ser; S) or asparagine (Asn N) and in SEQ ID NO: 46, Xaa is asparagine (Asn N) or histidine (His; H).

In one embodiment, Xaa in SEQ ID NO: 44 and 46 is asparagine and Xaa in SEQ ID NO: 45 is serine.

In one preferred embodiment, the antibody or antigen-binding fragment thereof which binds to alpha synuclein comprises:
a. a light chain variable region comprising:
i. a CDR-L1 comprising SEQ ID NO: 1;
ii. a CDR-L2 comprising SEQ ID NO: 2 and
iii. a CDR-L3 comprising SEQ ID NO: 3; and
b. a heavy chain variable region comprising:
iv. a CDR-H1 comprising SEQ ID NO: 4;
v. a CDR-H2 comprising SEQ ID NO: 5 and
vi. a CDR-H3 comprising SEQ ID NO: 6 and prevents alpha synuclein aggregation induced by alpha synuclein fibrils. Preferably, the antibody or antigen-binding fragment thereof binds to alpha synuclein to an epitope comprising, with reference to SEQ ID NO: 10, residues E123, Y125, E126, M127, P128, S129, E130 and E131, wherein the epitope optionally comprises A124 and G132.

In one embodiment, the antibody or antigen-binding fragment thereof according to the present invention is capable of binding alpha synuclein as a monomer and in fibrils. In one embodiment, the antibody or antigen-binding fragment thereof has a stronger binding affinity for alpha synuclein in fibrils compared to alpha synuclein as monomer. This is characterized by a constant of dissociation ($K_D$) at least 10-fold higher for monomeric alpha synuclein than for alpha synuclein in fibrils.

In one embodiment, the antibody or antigen-binding fragment thereof according to the present invention has a constant of dissociation ($K_D$) of less than 15 nM for monomeric alpha synuclein. In another embodiment, the antibody or antigen-binding fragment thereof according to the present invention has a constant of dissociation ($K_D$) of less than 10 nM for alpha synuclein in fibrils. In one preferred embodiment, the antibody or antigen-binding fragment thereof according to the present invention has a constant of dissociation ($K_D$) of less than 300 pM for alpha synuclein in fibrils.

The term "$K_D$" as used herein refers to the constant of dissociation which is obtained from the ratio of $K_d$ to $K_a$ (i.e. $K_d/K_a$) and is expressed as a molar concentration (M). $K_d$ and $K_a$ refers to the dissociation rate and association rate, respectively, of a particular antigen-antibody (or antigen-binding fragment thereof) interaction. $K_D$ values for antibodies can be determined using methods well established in the art. A method for determining the $K_D$ of an antibody is by using surface plasmon resonance, such as Biacore® system for example as described in the Examples herein, using isolated natural or recombinant alpha synuclein, a suitable fusion protein/polypeptide thereof or fibrils thereof. In one example affinity is measured using recombinant human alpha synuclein as described in the Examples herein. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

In one embodiment, the antibody or antigen-binding fragment thereof according to the present invention has a higher binding affinity (i.e. smaller $K_D$) for alpha synuclein in fibrils compared to alpha synuclein as monomer. The term "affinity" refers to the strength of an interaction between the antibody or antigen-binding fragment thereof and alpha synuclein.

In one embodiment, the antibody or antigen-binding fragment thereof according to the present invention has an $IC_{50}$ of less than 10 nM for blocking alpha synuclein aggregation induced by alpha synuclein in fibrils, preferably, the antibody or antigen-binding fragment thereof according to the present invention has an $IC_{50}$ of less than 5 nM for blocking alpha synuclein aggregation induced by alpha synuclein in fibrils. Examples of cell-based aggregation assays are disclosed in the examples.

The term $IC_{50}$ as used herein refers to the half maximal inhibitory concentration which is a measure of the effectiveness of a substance, such as an antibody, in inhibiting a specific biological or biochemical function, in the present invention aggregation induced by alpha synuclein, preferably alpha synuclein in fibrils. The $IC_{50}$ is a quantitative measure which indicates how much of a particular substance is needed to inhibit a given biological process by half.

In one embodiment, the antibody or antigen-binding fragment thereof according to the present invention has an $IC_{50}$ of less than 10 nM for blocking alpha synuclein aggregation induced by alpha synuclein in fibrils, preferably, the antibody or antigen-binding fragment thereof according to the present invention has an $IC_{50}$ of less than 5 nM for blocking alpha synuclein aggregation induced by alpha synuclein in fibrils in in-vitro assays.

The antibody or antigen-binding fragment thereof according to the present invention do not bind beta synuclein and/or gamma synuclein and are specific for alpha synuclein.

"Specific" as employed herein is intended to refer to an antibody that only recognizes the antigen to which it is specific or an antibody that has significantly higher binding affinity to the antigen to which it is specific (e.g. alpha synuclein) compared to binding to antigens to which it is non-specific (gamma and beta synucleins), for example at least 5, 6, 7, 8, 9, 10 times higher binding affinity.

Antibodies according to the present invention may be obtained using any suitable method known in the art. The alpha synuclein polypeptide/protein including fusion proteins, cells (recombinantly or naturally) expressing the polypeptide can be used to produce antibodies which specifically recognize alpha synuclein. The polypeptide may be the 'mature' polypeptide or a biologically active fragment or derivative thereof.

In one embodiment, the polypeptide (i.e. antigen) is human alpha synuclein monomer or a fragment thereof, preferably produced as described in the Examples below.

Polypeptides, for use to immunize a host, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The alpha synuclein polypeptide or a fragment thereof may in some instances be part of a larger protein such as a fusion protein for example fused to an affinity tag or similar.

Antibodies generated against the alpha synuclein polypeptide may be obtained, where immunization of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and WO2004/106377.

Screening for antibodies can be performed using assays to measure binding to alpha synuclein and/or assays to measure the inhibition of alpha synuclein to form fibrils in the presence of the antibody or fragment thereof.

The antibody or antigen-binding fragment thereof according to the present invention comprises complementarity determining regions (CDRs), three from a heavy chain and three from a light chain. Generally, the CDRs are in a framework and together form a variable region. By convention, the CDRs in the heavy chain variable region of an antibody or antigen-binding fragment thereof are referred as CDR-H1, CDR-H2 and CDR-H3 and in the light chain variable regions as CDR-L1, CDR-L2 and CDR-L3. They are numbered sequentially in the direction from the N-terminus to the C-terminus of each chain.

CDRs are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus, unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one preferred embodiment, the antibody or antigen-binding fragment thereof comprises a light chain variable region comprising a CDR-L1 comprising SEQ ID NO: 1, a CDR-L2 comprising SEQ ID NO: 2 and a CDR-L3 comprising SEQ ID NO: 3, and a heavy chain variable region comprising a CDR-H1 comprising SEQ ID NO: 4, a CDR-H2 comprising SEQ ID NO: 5 and a CDR-H3 comprising SEQ ID NO: 6.

Alternatively, the antibody or antigen-binding fragment comprises a light chain variable region comprising a CDR-L1 comprising SEQ ID NO: 1; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 8 and a CDR-H3 comprising SEQ ID NO: 9.

In another embodiment, the antibody or antigen-binding fragment comprises a light chain variable region comprising a CDR-L1 comprising SEQ ID NO: 7; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6.

In yet another embodiment, the antibody or antigen-binding fragment comprises a light chain variable region comprising a CDR-L1 comprising SEQ ID NO: 7; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 8 and a CDR-H3 comprising SEQ ID NO: 9.

In one embodiment the antibody or antigen-binding fragment thereof according to the present invention may comprise the framework regions of the animal in which the antibody was raised. For example, if the antibody was raised in rabbit, it will comprise the CDRs as defined above and the framework regions of the rabbit antibody such as an antibody comprising a light chain variable region according to SEQ ID NO: 11 (which nucleotide sequence is shown in SEQ ID NO: 12) and a heavy chain variable region according to SEQ ID NO: 13 (which nucleotide sequence is shown in SEQ ID NO: 14).

In one embodiment, the antibody may be a chimeric, humanized or human antibody or fragment thereof.

Chimeric antibodies are typically produced using recombinant DNA methods. The DNA may be modified by substituting the coding sequence for human L and H chains for the corresponding non-human (e.g. murine) H and L constant regions (Morrison; PNAS 81, 6851 (1984)).

Human antibodies comprise heavy or light chain variable regions or full length heavy or light chains that are "the product of" or "derived from" a particular germline sequence if the variable regions or full-length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody or fragment thereof that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Human antibodies may be produced by a number of methods known to those of skill in the art. Human antibodies can be made by the hybridoma method using human myeloma or mouse-human heteromyeloma cells lines (Kozbor, J Immunol; (1984) 133:3001; Brodeur, Monoclonal Isolated Antibody Production Techniques and Applications, pp 51-63, Marcel Dekker Inc, 1987). Alternative methods include the use of phage libraries or transgenic mice both of which utilize human variable region repertoires (Winter G; (1994) Annu Rev Immunol 12:433-455, Green L L, (1999) J Immunol Methods 231:1 1-23).

In one preferred embodiment of the present invention, the antibody or antigen-binding fragment thereof according to the disclosure are humanized.

Therefore, the antibody or antigen-binding fragment thereof binds alpha synuclein and comprises:
 a. a light chain variable region comprising:
  i. a CDR-L1 comprising SEQ ID NO: 44;
  ii. a CDR-L2 comprising SEQ ID NO: 2 and
  iii. a CDR-L3 comprising to SEQ ID NO: 3; and
 b. a heavy chain variable region comprising:
  iv. a CDR-H1 comprising SEQ ID NO: 4;
  v. a CDR-H2 comprising SEQ ID NO: 45 and
  vi. a CDR-H3 comprising SEQ ID NO: 46
wherein the antibody or antigen-binding fragment thereof is humanized. Preferably, the humanized antibody or antigen-binding fragment thereof prevents alpha synuclein aggregation induced by alpha synuclein fibrils, and more preferably binds to alpha synuclein to an epitope comprising, with reference to SEQ ID NO: 10, residues E123, Y125, E126, M127, P128, S129, E130 and E131, wherein the epitope optionally comprises A124 and G132.

In SEQ ID NO: 44, Xaa is asparagine (Asn; N) or arginine (Arg; R). Independently, in SEQ ID NO: 45, Xaa is serine (Ser; S) or asparagine (Asn N) and in SEQ ID NO: 46, Xaa is asparagine (Asn N) or histidine (His; H).

In one embodiment, the humanized antibody or antigen-binding fragment thereof binds alpha synuclein and comprises:
 a. a light chain variable region comprising:
  i. a CDR-L1 comprising SEQ ID NO: 44;
  ii. a CDR-L2 comprising SEQ ID NO: 2 and
  iii. a CDR-L3 comprising to SEQ ID NO: 3; and
 b. a heavy chain variable region comprising:
  iv. a CDR-H1 comprising SEQ ID NO: 4;
  v. a CDR-H2 comprising SEQ ID NO: 45 and
  vi. a CDR-H3 comprising SEQ ID NO: 46
and prevents alpha synuclein aggregation induced by alpha synuclein fibrils, and binds to alpha synuclein to an epitope comprising, with reference to SEQ ID NO: 10, residues E123, Y125, E126, M127, P128, S129, E130 and E131, wherein in SEQ ID NO: 44, Xaa is asparagine (Asn; N) in SEQ ID NO: 45, Xaa is serine (Ser; S) and in SEQ ID NO: 46, Xaa is asparagine (Asn N).

In one preferred embodiment, the humanized antibody or antigen-binding fragment thereof binds alpha synuclein and comprises:
 a. a light chain variable region comprising:
  i. a CDR-L1 comprising SEQ ID NO: 1;
  ii. a CDR-L2 comprising SEQ ID NO: 2 and
  iii. a CDR-L3 comprising to SEQ ID NO: 3; and
 b. a heavy chain variable region comprising:
  iv. a CDR-H1 comprising SEQ ID NO: 4;
  v. a CDR-H2 comprising SEQ ID NO: 5 and
  vi. a CDR-H3 comprising SEQ ID NO: 6
and prevents alpha synuclein aggregation induced by alpha synuclein fibrils, and binds to alpha synuclein to an epitope comprising, with reference to SEQ ID NO: 10, residues E123, Y125, E126, M127, P128, S129, E130 and E131

As used herein, the term "humanized" antibody or antigen-binding fragment thereof refers to an antibody or antigen-binding fragment thereof wherein the heavy and/or light chain contains one or more CDRs (including, if desired, one or more modified CDRs) from a donor antibody (e.g. a non-human antibody such as a murine or rabbit monoclonal antibody) grafted into a heavy and/or light chain variable region framework of an acceptor antibody (e.g. a human antibody). For a review, see Vaughan et al, Nature Biotechnology, 16, 535-539, 1998. In one embodiment, rather than the entire CDR being transferred, only one or more of the specificity determining residues from any one of the CDRs described herein above are transferred to the human antibody framework (see for example, Kashmiri et al., 2005, Methods, 36, 25-34). In one embodiment, only the specificity determining residues from one or more of the CDRs described herein above are transferred to the human antibody framework. In another embodiment, only the specificity determining residues from each of the CDRs described herein above are transferred to the human antibody framework.

When the CDRs are grafted, any appropriate acceptor variable region framework sequence may be used having regard to the class/type of the donor antibody from which the CDRs are derived, including mouse, primate and human framework regions.

Suitably, the humanized antibody according to the present invention has a variable domain comprising human acceptor framework regions as well as one or more of the CDRs provided specifically herein. Thus, provided in one embodiment is a blocking humanized antibody which binds alpha synuclein, preferably human alpha synuclein, wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://www.imgt.org/

In a humanized antibody or antigen-binding fragment thereof according to the present invention, the acceptor heavy and light chains do not necessarily need to be derived from the same antibody and may, if desired, comprise composite chains having framework regions derived from different chains.

A suitable framework region for the light chain of the humanized antibody or antigen-binding fragment thereof according to the present invention is derived from the human germline IGKV1-16 JK4 having SEQ ID NO:39 and which nucleotide sequence is shown in SEQ ID NO: 40.

A suitable framework region for the heavy chain of the humanized antibody or antigen-binding fragment thereof according to the present invention is derived from the human germline IGHV3-23 JH4 having the sequence as shown in SEQ ID NO: 41 and which nucleotide sequence is shown in SEQ ID NO: 42.

Accordingly, in one embodiment there is provided a humanized antibody or antigen-binding fragment thereof comprising:

the sequence given in SEQ ID NO: 1 or SEQ ID NO: 7 for CDR-L1, the sequence given in SEQ ID NO: 2 for CDR-L2 and the sequence given in SEQ ID NO: 3 for CDRL3, wherein the light chain framework region is derived from the human germline IGKV1-16 JK4; and the sequence given in SEQ ID NO: 4 for CDR-H1, the sequence given in SEQ ID NO: 5 or SEQ ID NO: 8 for CDR-H2 and the sequence given in SEQ ID NO: 6 or SEQ ID NO: 9 for CDR-H3, wherein the heavy chain framework region is derived from the human germline IGHV3-23 JH4.

In the humanized antibody or antigen-binding fragment thereof according to the present invention, the framework regions may not have the same exact sequences as those of the acceptor antibody. For instance, unusual residues may be changed to more frequently-occurring residues for that acceptor chain class or type. Alternatively, selected residues in the acceptor framework regions may be changed so that they correspond to the residues found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967.

Thus, in one embodiment 1, 2, 3, 4, 5, 6, 7 or 8 residues in the framework are replaced with an alternative amino acid residue.

Accordingly, in one embodiment, there is provided a humanized antibody or antigen-binding fragment thereof, wherein at least the residues at each of positions 48 and 72 of the variable domain of the light chain (with reference to SEQ ID NO: 15 or 19) are donor residues, see for example the sequences given in SEQ ID NO: 15, 17, 19 and 21. Preferably, residue 48 of the light chain variable domain is glutamine and/or residue 72 of the light chain variable domain is glutamine.

More preferably, residues 48 and 72 are both glutamine in the humanized light chain variable region of the humanized antibody or antigen-binding fragment thereof according to the present invention.

In another embodiment, there is provided a humanized antibody or antigen-binding fragment thereof, wherein at least the residues at each of positions 24, 47, 48, 49, 73 and 97 (with reference to SEQ ID NO: 31 or 35) or 24, 47, 48, 49, 78 and 97 of the variable domain of the heavy chain (with reference to SEQ ID NO: 23 and 27) are donor residues, see for example the sequences given in SEQ ID NO: 23, 25, 27, 29, 31, 33, 35 and 37.

Preferably residue 24 of the heavy chain variable domain is valine and/or residue 47 of the heavy chain variable domain is tyrosine and/or residue 48 of the heavy chain variable domain is isoleucine and/or residue 49 of the heavy chain variable domain is glycine and/or residue 97 of the heavy chain variable domain is arginine and/or residue 73 of the heavy chain variable domain is serine and/or residue 78 of the heavy chain variable domain is valine.

Preferably residue 24 is valine, residue 47 is tyrosine, residue 48 is isoleucine, residue 49 is glycine, residue 73 is serine and residue 97 is arginine in the humanized heavy chain variable region according to the present invention. Also, preferably residue 24 is valine, residue 47 is tyrosine, residue 48 is isoleucine, residue 49 is glycine, residue 78 is valine and residue 97 is arginine in the humanized heavy chain variable region of the humanized antibody or antigen-binding fragment thereof according to the present invention.

In one preferred embodiment of the present invention the antibody or antigen-binding fragment thereof binds alpha synuclein and comprises a light chain variable region comprising SEQ ID NO: 15 and a heavy chain variable region comprising SEQ ID NO: 31.

In another embodiment, the antibody or antigen-binding fragment thereof comprises:
  a light chain variable region comprising SEQ ID NO: 15 and a heavy chain variable region comprising SEQ ID NO: 23; or
  a light chain variable region comprising SEQ ID NO: 15 and a heavy chain variable region comprising SEQ ID NO: 27 or 35; or
  a light chain variable region comprising SEQ ID NO: 19 and a heavy chain variable region comprising SEQ ID NO: 23 or 31; or
  a light chain variable region comprising SEQ ID NO: 19 and a heavy chain variable region comprising SEQ ID NO: 27 or 35.

In one embodiment, the invention provides an antibody or an antigen-binding fragment thereof comprising a sequence which is 80% similar or identical to a sequence disclosed herein, for example 85%, 90%, 91%, 92%, 93%, 94%, 95% 96%, 97%, 98% or 99% over part or whole of the relevant sequence, for example a variable domain sequence, a CDR sequence or a variable domain sequence, excluding the CDRs. In one embodiment, the relevant sequence is SEQ ID NO: 15. In one embodiment the relevant sequence is SEQ ID NO: 23 or SEQ ID NO: 31.

In one embodiment, the present invention provides an antibody or an antigen-binding fragment thereof which binds human alpha synuclein comprising a light chain, wherein the variable domain of the light chain comprises a sequence having at least 80%, 85%, 90%, 91%, 92%, 93%, 94%, 95% 96%, 97%, 98% or 99% identity or similarity to the sequence given in SEQ ID NO:15 or SEQ ID NO: 19 and/or the variable domain of the heavy chain comprises a sequence having at least 80%, 85%, 90%, 91%, 92%, 93%, 94%, 95% 96%, 97%, 98% or 99% identity or similarity to the sequence given in SEQ ID NO: 31, SEQ ID NO: 23, SEQ ID NO: 27 or SEQ ID NO: 35.

In one embodiment, the present invention provides an antibody or an antigen-binding fragment thereof which binds human alpha synuclein wherein the antibody or an antigen-binding fragment thereof has a light chain variable domain which is at least 90%, 91%, 92%, 93%, 94%, 95% 96%, 97%, 98% or 99% similar or identical to the sequence given in SEQ ID NO: 15 but wherein the antibody or an antigen-binding fragment thereof has the sequence given in SEQ ID NO: 1 or SEQ ID NO: 7 for CDR-L1, the sequence given in SEQ ID NO: 2 for CDR-L2 and the sequence given in SEQ ID NO: 3 for CDR-L3.

In one embodiment, the present invention provides an antibody or an antigen-binding fragment thereof which binds human alpha synuclein wherein the antibody or an antigen-binding fragment thereof has a heavy chain variable domain which is at least 90%, 91%, 92%, 93%, 94%, 95% 96%, 97%, 98% or 99% similar or identical to the sequence given in SEQ ID NO: 31 but wherein the antibody or an antigen-binding fragment thereof has the sequence given in SEQ ID NO: 4 for CDR-H1, the sequence given in SEQ NO: 5 or SEQ ID NO: 8 for CDR-H2 and the sequence given in SEQ ID NO: 6 or SEQ ID NO: 9 for CDR-H3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In one embodiment, the antigen-binding fragment according to the present invention may be, but is not limited to, a Fab, modified Fab, Fab', modified Fab', F(ab')2, Fv, single domain antibodies (e.g. VH or VL or VHH), scFv, dsscFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in WO2005/003169, WO2005/003170 and WO2005/003171. Multi-valent antibodies may comprise multiple specificities e.g. bispecific or may be monospecific (see for example WO 92/22853, WO05/113605, WO2009/040562 and WO2010/035012).

An alternative antigen-binding fragment comprises a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in International Patent Application Publication No, WO2015/197772, which is hereby incorporated by reference in its entirety and particularly with respect to the discussion of antibody fragments.

In another embodiment, the antibody or antigen-binding fragment thereof according to the present invention is part of an alpha synuclein binding fusion protein which comprises for example fused antigen-binding fragments of the present invention, for example as a Fab or Fab' fragment, and one or two single domain antibodies (dAb) linked directly or indirectly thereto, for example as described in WO2009/040562, WO2010035012, WO2011/030107, WO2011/061492 and WO2011/086091 all incorporated herein by reference. In one embodiment, the fusion protein comprises two domain antibodies, for example as a variable heavy (VH) and variable light (VL) pairing, optionally linked by a disulphide bond.

In one embodiment, the Fab or Fab' element of the fusion protein has the same or similar specificity to the single domain antibody or antibodies. In one embodiment, the Fab or Fab' has a different specificity to the single domain antibody or antibodies, that is to say the fusion protein is multivalent. In one embodiment, a multivalent fusion protein according to the present invention has an albumin binding site, for example a VH/VL pair therein provides an albumin binding site.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example, IgG4 molecules in which the serine at position 241 has been changed to proline as described in Angal et al. (Angal et al., Molecular Immunology, 1993, 30 (1), 105-108) and termed IgG4P herein, may be used.

In one embodiment, the antibody is a full-length antibody, preferably selected from an IgG1, and IgG4 or an IgG4P.

Therefore, the present invention provides for a full-length humanized antibody which binds alpha synuclein and comprises:

a. a light chain variable region comprising:
   i. a CDR-L1 comprising SEQ ID NO: 44;
   ii. a CDR-L2 comprising SEQ ID NO: 2 and
   iii. a CDR-L3 comprising SEQ ID NO: 3; and
b. a heavy chain variable region comprising:
   iv. a CDR-H1 comprising SEQ ID NO: 4;
   v. a CDR-H2 comprising SEQ ID NO: 45 and
   vi. a CDR-H3 comprising SEQ ID NO: 46 wherein the humanized antibody prevents alpha synuclein aggregation induced by alpha synuclein fibrils, and preferably binds to alpha synuclein to an epitope comprising, with reference to SEQ ID NO: 10, residues E123, Y125, E126, M127, P128, S129, E130 and E131, wherein the epitope optionally comprises A124 and G132 and wherein the antibody is an IgG4P isoform.

In SEQ ID NO: 44, Xaa is asparagine (Asn; N) or arginine (Arg; R). Independently, in SEQ ID NO: 45, Xaa is serine (Ser; S) or asparagine (Asn N) and in SEQ ID NO: 46, Xaa is asparagine (Asn N) or histidine (His; H).

In one preferred embodiment, the full-length humanized antibody which binds alpha synuclein and comprises:
  a. a light chain variable region comprising:
    i. a CDR-L1 comprising SEQ ID NO: 44;
    ii. a CDR-L2 comprising SEQ ID NO: 2 and
    iii. a CDR-L3 comprising to SEQ ID NO: 3; and
  b. a heavy chain variable region comprising:
    iv. a CDR-H1 comprising SEQ ID NO: 4;
    v. a CDR-H2 comprising SEQ ID NO: 45 and
    vi. a CDR-H3 comprising SEQ ID NO: 46
and prevents alpha synuclein aggregation induced by alpha synuclein fibrils, and preferably binds to alpha synuclein to an epitope comprising, with reference to SEQ ID NO: 10, residues E123, Y125, E126, M127, P128, S129, E130 and E131, wherein the epitope optionally comprises A124 and G132 and wherein the antibody is an IgG4P isoform, wherein in SEQ ID NO: 44, Xaa is asparagine (Asn; N), in SEQ ID NO: 45, Xaa is serine (Ser; S) and in SEQ ID NO: 46, Xaa is asparagine (Asn N).

In a most preferred embodiment, the full-length humanized antibody which binds alpha synuclein and comprises:
  a. a light chain variable region comprising:
    i. a CDR-L1 comprising SEQ ID NO: 1;
    ii. a CDR-L2 comprising SEQ ID NO: 2 and
    iii. a CDR-L3 comprising to SEQ ID NO: 3; and
  b. a heavy chain variable region comprising:
    iv. a CDR-H1 comprising SEQ ID NO: 4;
    v. a CDR-H2 comprising SEQ ID NO: 5 and
    vi. a CDR-H3 comprising SEQ ID NO: 6
and prevents alpha synuclein aggregation induced by alpha synuclein fibrils, and preferably binds to alpha synuclein to an epitope comprising, with reference to SEQ ID NO: 10, residues E123, Y125, E126, M127, P128, S129, E130 and E131, wherein the epitope optionally comprises A124 and G132.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In one embodiment, a C-terminal amino acid from the antibody is cleaved during post-translation modifications.

In one embodiment, an N-terminal amino acid from the antibody is cleaved during post-translation modifications.

In one embodiment, the antibody or an antigen-binding fragment thereof comprises a light chain variable region according to SEQ ID NO: 15 and a heavy variable region selected from SEQ ID NO: 23 or SEQ ID NO: 31. For example, the antibody may be a full length IgG4 antibody comprising a light chain variable region according to SEQ ID NO: 15 and a heavy chain variable region selected from SEQ ID NO: 23 or SEQ ID NO: 31. In another embodiment, the antibody is a full length IgG4 antibody comprising a light chain according to SEQ ID NO: 17 and a heavy chain according to SEQ ID NO: 25 or SEQ ID NO: 33. In yet another embodiment the antigen-binding fragment is a Fab' comprising a light chain variable region according to SEQ ID NO: 15 and a heavy chain variable region selected from SEQ ID NO: 23 or SEQ ID NO: 31.

In another embodiment, the antibody or an antigen-binding fragment thereof comprises a light chain variable region according to SEQ ID NO: 15 and a heavy chain variable region selected from SEQ ID NO: 27 or SEQ ID NO: 35. For example, the antibody is a full length IgG4 antibody comprising a light chain variable region according to SEQ ID NO: 15 and a heavy chain variable region selected from SEQ ID NO: 27 or SEQ ID NO: 35. In another embodiment, the antibody is full length IgG4 antibody comprising a light chain according to SEQ ID NO: 17 and a heavy chain according to SEQ ID NO: 29 or SEQ ID NO: 37. In yet another embodiment the antigen-binding fragment is a Fab' comprising a light variable region according to SEQ ID NO: 15 and a heavy variable region selected from SEQ ID NO: 27 or SEQ ID NO: 35.

In another embodiment, the antibody or an antigen-binding fragment thereof comprises a light chain variable region according to SEQ ID NO: 19 and a heavy chain variable region selected from SEQ ID NO: 27 or SEQ ID NO: 35. For example, the antibody is a full length IgG4 antibody comprising a light chain variable region according to SEQ ID NO: 19 and a heavy chain variable region selected from SEQ ID NO: 27 or SEQ ID NO: 35. In another embodiment, the antibody is full length IgG4 antibody comprising a light chain according to SEQ ID NO: 21 and a heavy chain according to SEQ ID NO: 29 or SEQ ID NO: 37. In yet another embodiment the antigen-binding fragment is a Fab' comprising a light chain variable region according to SEQ ID NO: 19 and a heavy chain variable region selected from SEQ ID NO: 27 or SEQ ID NO: 35.

In another embodiment, the antibody or an antigen-binding fragment thereof comprises a light chain variable region according to SEQ ID NO: 19 and a heavy chain variable region selected from SEQ ID NO: 23 or SEQ ID NO: 31. For example, the antibody is a full length IgG4 antibody comprising a light chain variable region according to SEQ ID NO: 19 and a heavy chain variable region selected from SEQ ID NO: 23 or SEQ ID NO: 31. In another embodiment, the antibody is full length IgG4 antibody comprising a light chain according to SEQ ID NO: 21 and a heavy chain according to SEQ ID NO: 25 or SEQ ID NO: 33. In yet another embodiment the antigen-binding fragment is a Fab' comprising a light chain variable region according to SEQ ID NO: 21 and a heavy chain variable region selected from SEQ ID NO: 25 or SEQ ID NO: 33.

In a preferred embodiment, the antibody binds alpha synuclein and is a full-length IgG4 antibody comprising a light chain variable region comprising SEQ ID NO: 15 and a heavy chain variable comprising SEQ ID NO: 31. More preferably, the antibody prevents alpha synuclein aggregation induced by alpha synuclein fibrils, and even more preferably the antibody binds to alpha synuclein to an epitope comprising, with reference to SEQ ID NO: 10, residues E123, Y125, E126, M127, P128, S129, E130 and E131, wherein the epitope optionally comprises A124 and G132.

In another preferred embodiment, the antibody binds alpha synuclein and is a full-length IgG4 antibody comprising a light chain comprising SEQ ID NO: 17 and a heavy chain comprising SEQ ID NO: 33. More preferably the antibody prevents alpha synuclein aggregation induced by alpha synuclein fibrils, and even more preferably the antibody binds to alpha synuclein to an epitope comprising, with reference to SEQ ID NO: 10, residues E123, Y125, E126, M127, P128, S129, E130 and E131, wherein the epitope optionally comprises A124 and G132.

Furthermore, the present invention also provides for an antibody or antigen-binding fragment thereof which competes for binding alpha synuclein with the antibody or antigen-binding fragment thereof according to the present invention.

Therefore, the present invention provides for an antibody or antigen-binding fragment thereof which competes for binding alpha synuclein with the antibodies or antigen-binding fragments according to the present invention by cross-blocking or being cross-blocked by the antibody or antigen-binding fragment thereof of the invention; and in particular an antibody or antigen-binding fragment thereof comprising a heavy chain variable region comprising SEQ ID NO: 23, SEQ ID NO: 31, SEQ ID NO: 27 or SEQ ID NO: 35 and a light chain variable region comprising SEQ ID NO: 15 or SEQ ID NO: 19.

In another embodiment, the antibody or antigen-binding fragment thereof competes for binding alpha synuclein at the same epitope as the antibody or antigen-binding fragment thereof according to the present invention and in particular, competes with an antibody or antigen-binding fragment thereof with a heavy chain variable region comprising SEQ ID NO: 23, SEQ ID NO: 31, SEQ ID NO: 27 or SEQ ID NO: 35 and a light chain variable region comprising SEQ ID NO: 15 or SEQ ID NO: 19 and for binding alpha synuclein to an epitope comprising, with reference to SEQ ID NO: 10, at least residues M127, P128, S129, E130 and E131, preferably residues E123, Y125, E126, M127, P128, S129, E130 and E131.

In one embodiment, such antibody or antigen-binding fragment thereof competes with the antibodies or fragments thereof according to the present invention and has a heavy chain variable region having at least 80% identity or similarity to the sequence according to SEQ ID NO: 23, SEQ ID NO: 31, SEQ ID NO: 27 or SEQ ID NO: 35; and/or has a light chain variable region having at least 80% identity or similarity to the sequence according to SEQ ID NO: 15 or SEQ ID NO: 19.

Competing antibodies can be identified using any suitable method in the art, for example by using competition ELISA or BIAcore assays where binding of the cross-blocking antibody to human alpha synuclein prevents the binding of an antibody of the present invention or vice versa. Such competing assays may use isolated natural or recombinant alpha synuclein or a suitable fusion protein/polypeptide. In one example competition is measured using recombinant human alpha synuclein (SEQ ID NO: 10). In one example the recombinant human alpha synuclein tagged at the N-terminus or C-terminus (for example a 6×His tag fusion with a TEV recognition site) is used as per examples herein. In another example, competition is measured using recombinant human alpha synuclein fibrils.

In one embodiment, the competing antibodies are fully human or humanized. In one embodiment, the competing antibodies have an affinity for human alpha synuclein of 100 pM or less, preferably 50 pM or less.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the anti-alpha synuclein antibody or antigen-binding fragment thereof according to the present invention may be engineered to have an appropriate isoelectric point. This may lead to antibodies and/or fragments with more robust properties, in particular suitable solubility and/or stability profiles and/or improved purification characteristics.

Thus, in one aspect the invention provides a humanized antibody or antigen-binding fragment thereof which binds alpha synuclein and is engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value, acidic residues may be introduced to lower the pI, as required. It is important that when manipulating the pI care must be taken to retain the desirable activity of the antibody or fragment. Thus, in one embodiment the engineered antibody or antigen-binding fragment thereof has the same or substantially the same activity as the "unmodified" antibody or fragment.

Programs such as **ExPASY http://www.expasy.ch/tools/pi_tool.html, and http://www.iut-arles.up.univ-mrs.fr/w3bb/d_abim/compo-p.html, may be used to predict the isoelectric point of the antibody or fragment.

It will be appreciated that the affinity of antibodies provided by the present invention may be altered using any suitable method known in the art. The present invention therefore also relates to variants of the antibody molecules of the present invention, which have an improved affinity for alpha synuclein, in particular human alpha synuclein. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

Within the present invention, affinity maturation was performed by IOTA (WO2014198951).

If desired the antibody or antigen-binding fragment thereof according to the present invention may be conjugated to one or more effector molecule(s). It will be appreciated that the effector molecule may comprise a single effector molecule or two or more such molecules so linked as to form a single moiety that can be attached to the antibodies or antigen-binding fragment thereof of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

In one embodiment, the polymer is albumin or a fragment thereof, such as human serum albumin or a fragment thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example, the antibody or antigen-binding fragment according to the present invention are attached to poly (ethyleneglycol) (PEG) moieties. In one particular embodiment, the antigen-binding fragment according to the present invention and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

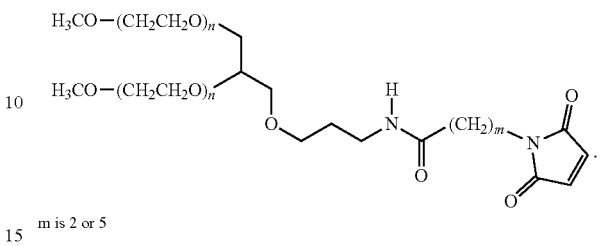

m is 2 or 5

That is to say each PEG is about 20,000 Da.

Thus in one embodiment the PEG is 2,3-Bis(methylpolyoxyethylene-oxy)-1-{[3-(6-maleimido-1-oxohexyl) amino]propyloxy} hexane (the 2 arm branched PEG, —CH2) 3NHCO(CH2)5-MAL, Mw 40,000 known as SUN-BRIGHT GL2-400MA3.

Further alternative PEG effector molecules of the following type:

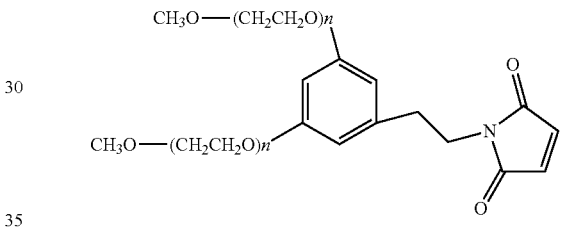

are available from Dr Reddy, NOF and Jenkem.

In one embodiment, the Fab or Fab' according to the present invention is conjugated to a PEG molecule.

In one embodiment, there is provided an antibody which is PEGylated (for example with a PEG described herein), attached through a cysteine amino acid residue at or about amino acid 226 in the chain, for example amino acid 226 of the heavy chain (by sequential numbering), for example amino acid 223 of SEQ ID NO: 33.

In one embodiment, the present disclosure provides a Fab'PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one embodiment, there is provided a Fab' conjugated to a polymer, such as a PEG molecule, a starch molecule or an albumin molecule. In one embodiment, there is provided a scFv conjugated to a polymer, such as a PEG molecule, a starch molecule or an albumin molecule. In one embodiment, the Fab or Fab' according to the present disclosure is conjugated to human serum albumin. In one embodiment, the antibody or fragment is conjugated to a starch molecule, for example to increase the half-life. Methods of conjugating starch to a protein as described in U.S. Pat. No. 8,017,739 incorporated herein by reference.

The present invention also provides an isolated polynucleotide encoding the antibody or antigen-binding fragment thereof according to the present invention. The isolated polynucleotide according to the present invention may comprise synthetic DNA, for instance produced by chemical processing, cDNA, genomic DNA or any combination thereof.

Standard techniques of molecular biology may be used to prepare DNA sequences coding for the antibody or antigen-binding fragment thereof of the present invention. Desired DNA sequences may be synthesized completely or in part using oligonucleotide synthesis techniques. Site-directed mutagenesis and polymerase chain reaction (PCR) techniques may be used as appropriate.

In one embodiment, the isolated polynucleotide according to the invention encodes:
  a. a light chain variable region, wherein the polynucleotide:
    i. is at least 90% identical to SEQ ID NO: 16 or SEQ ID NO: 20; or
    ii. comprises SEQ ID NO: 16 or 20; or
    iii. consists essentially of SEQ ID NO: 16 or SEQ ID NO: 20;
  b. a heavy chain variable region, wherein the polynucleotide:
    i. is at least 90% identical to SEQ ID NO: 24 or SEQ ID NO: 28 or SEQ ID NO: 32 or SEQ ID NO: 36; or
    ii. comprises SEQ ID NO: 24 or SEQ ID NO: 28 or SEQ ID NO: 32 or SEQ ID NO: 36; or
    iii. consists essentially of SEQ ID NO: 24 or SEQ ID NO: 28 or SEQ ID NO: 32 or SEQ ID NO: 36;
  c. a light chain, wherein the polynucleotide:
    i. is at least 90% identical to SEQ ID NO: 18 or SEQ ID NO: 22; or
    ii. comprises SEQ ID NO: 18 or 22; or
    iii. consists essentially of SEQ ID NO: 18 or SEQ ID NO: 22;
  d. a heavy chain, wherein the polynucleotide:
    i. is at least 90% identical to SEQ ID NO: 26 or SEQ ID NO: 30 or SEQ ID NO: 34 or SEQ ID NO: 38; or
    ii. comprises SEQ ID NO: 26 or SEQ ID NO: 30 or SEQ ID NO: 34 or SEQ ID NO: 38; or
    iii. consists essentially of SEQ ID NO: 26 or SEQ ID NO: 30 or SEQ ID NO: 34 or SEQ ID NO: 38;
  e. a light chain variable region, wherein the polynucleotide:
    i. is at least 90% identical to SEQ ID NO: 12; or
    ii. comprises SEQ ID NO: 12; or
    iii. consists essentially of SEQ ID NO: 12;
  f. a heavy chain variable region, wherein the polynucleotide:
    i. is at least 90% identical to SEQ ID NO: 14; or
    ii. comprises SEQ ID NO: 14; or
    iii. consists essentially of SEQ ID NO: 14.

In one embodiment, the present invention provides an isolated polynucleotide encoding the heavy chain of an antibody Fab' fragment or of an IgG1 or IgG4 antibody of the present invention which comprises the sequence given in SEQ ID NO: 24, 28, 32 or 36. Also provided is an isolated polynucleotide encoding the light chain of an antibody Fab' fragment or of an IgG1 or IgG4 antibody of the present invention which comprises the sequence given in SEQ ID NO: 16 or 20.

In another embodiment, the present invention provides an isolated polynucleotide encoding the heavy chain and the light chain of an IgG4(P) antibody of the present invention in which the polynucleotide encoding the heavy chain comprises the sequence given in SEQ ID NO: 26, 30, 34 or 38 and the polynucleotide encoding the light chain comprises the sequence given in SEQ ID NO: 18 or 22.

The present invention also provides for a cloning or expression vector comprising one or more polynucleotides described herein. In one example, the cloning or expression vector according to the present invention comprises one or more isolated polynucleotides comprising a sequence selected from SEQ ID NO: 16, 18, 20, 22, 24, 26, 28, 30, 32, 34, 36 or 38.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more isolated polynucleotide sequences according to the invention or one or more cloning or expression vectors comprising one or more isolated polynucleotide sequences encoding an antibody of the present invention. Any suitable host cell/vector system may be used for expression of the polynucleotide sequences encoding the antibody or antigen-binding fragment thereof of the present invention. Bacterial, for example E. coli, and other microbial systems may be used or eukaryotic, for example mammalian, host cell expression systems may also be used. Suitable mammalian host cells include CHO, myeloma or hybridoma cells.

Suitable types of Chinese Hamster Ovary (CHO cells) for use in the present invention may include CHO and CHO-K1 cells including dhfr-CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NSO myeloma cells and SP2 cells, COS cells. The host cell may be stably transformed or transfected with the isolated polynucleotide sequences or the expression vectors according to the present invention.

In one embodiment, the host cell according to the present invention is a CHO-DG44 cell stably transfected with an expression vectors comprising the isolated polynucleotide sequences of the present invention, preferably comprising the isolated polynucleotide sequences according to SEQ ID NO: 18 and 26 or SEQ ID NO: 18 and 34 or SEQ ID NO: 18 and 30 or SEQ ID NO: 18 and 38.

The present invention also provides a process for the production of an antibody or an antigen-binding fragment thereof according to the present invention comprising culturing a host cell according to the present invention under conditions suitable for producing the antibody or antigen-binding fragment thereof according to the invention, and isolating the antibody or antigen-binding fragment thereof.

The antibody or antigen-binding fragment thereof may comprise only a heavy or light chain polypeptide, in which case only a heavy chain or light chain polypeptide coding sequence needs to be used to transfect the host cells. For production of antibodies or antigen-binding fragments thereof comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Thus, there is provided a process for culturing a host cell and expressing an antibody or fragment thereof, isolating the latter and optionally purifying the same to provide an isolated antibody or fragment. In one embodiment, the process further comprises the step of conjugating an effector molecule to the isolated antibody or fragment, for example conjugating to a PEG polymer in particular as described herein.

Thus, in one embodiment there is provided a purified anti-alpha synuclein antibody or fragment thereof, for example a humanized antibody or fragment thereof, in particular an antibody or fragment thereof according to the invention, in substantially purified from, in particular free or substantially free of endotoxin and/or host cell protein or DNA.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less such as 100 µg per mg or less, in particular 20 µg per mg, as appropriate.

As the antibodies of the present invention are useful in the treatment, diagnosis and/or prophylaxis of a pathological condition such as an alpha synucleinopathy, the present invention also provides for a pharmaceutical or diagnostic composition comprising an antibody or antigen-binding fragment thereof according to the present invention in combination with one or more of a pharmaceutically acceptable carrier, excipient or diluent.

Preferably, the pharmaceutical or diagnostic composition comprises a humanized antibody which binds alpha synuclein and comprises:
 a. a light chain variable region comprising:
  i. a CDR-L1 comprising SEQ ID NO: 44;
  ii. a CDR-L2 comprising SEQ ID NO: 2 and
  iii. a CDR-L3 comprising SEQ ID NO: 3; and
 b. a heavy chain variable region comprising:
  iv. a CDR-H1 comprising SEQ ID NO: 4;
  v. a CDR-H2 comprising SEQ ID NO: 45 and
  vi. a CDR-H3 comprising SEQ ID NO: 46.

More preferably, the pharmaceutical or diagnostic composition comprises a humanized antibody which binds alpha synuclein and comprises:
 a. a light chain variable region comprising:
  i. a CDR-L1 comprising SEQ ID NO: 1;
  ii. a CDR-L2 comprising SEQ ID NO: 2 and
  iii. a CDR-L3 comprising SEQ ID NO: 3; and
 b. a heavy chain variable region comprising:
  iv. a CDR-H1 comprising SEQ ID NO: 4;
  v. a CDR-H2 comprising SEQ ID NO: 5 and
  vi. a CDR-H3 comprising SEQ ID NO: 6.

In one embodiment, the antibody or antigen-binding fragment thereof according to the present invention is the sole active ingredient. In another embodiment, the antibody or antigen-binding fragment thereof according to the present invention is in combination with one or more additional active ingredients. Alternatively, the pharmaceutical compositions comprise the antibody or antigen-binding fragment thereof according to the present invention which is the sole active ingredient and it may be administered individually to a patient in combination (e.g. simultaneously, sequentially or separately) with other agents, drugs or hormones.

In another embodiment, the pharmaceutical composition comprises an antibody or antigen-binding fragment thereof comprising a light chain variable region of SEQ ID NO: 15 or 19 and comprising a heavy chain variable region of SEQ ID NO: 23, 27, 31 or 35, for example SEQ ID NO: 15 and SEQ ID NO: 23 or SEQ ID NO: 15 and SEQ ID NO: 31.

Preferably, the present invention provides for a pharmaceutical composition comprising an antibody or antigen-binding fragment thereof which binds alpha synuclein and comprises a light chain variable region of SEQ ID NO: 15 and a heavy chain variable region of SEQ ID NO: 31.

The pharmaceutical compositions according to the invention may be administered suitably to a patient to identify the therapeutically effective amount required. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg. Pharmaceutical compositions may be conveniently presented in unit dose forms containing a predetermined amount of an active agent of the invention per dose.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion, in intravenous, inhalable or sub-cutaneous form. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody or antigen-binding fragment thereof according to the invention may be in dry form, for reconstitution before use with an appropriate sterile liquid. Solid forms suitable for solution in, or suspension in, liquid vehicles prior to injection may also be prepared.

Once formulated, the compositions of the invention can be administered directly to the subject. Accordingly, provided herein is the use of an antibody or an antigen-binding fragment thereof according to the invention for the manufacture of a medicament.

The subjects to be treated can be animals. Preferably, the pharmaceutical compositions according to the present invention are adapted for administration to human subjects.

Hence, in another aspect the present invention provides for the antibody or antigen-binding fragment thereof or a pharmaceutical composition comprising the antibody or antigen-binding fragment thereof for use in therapy, wherein the antibody or antigen-binding fragment thereof binds alpha synuclein and comprises:

a. a light chain variable region comprising:
  i. a CDR-L1 comprising SEQ ID NO: 44;
  ii. a CDR-L2 comprising SEQ ID NO: 2 and
  iii. a CDR-L3 comprising SEQ ID NO: 3; and
b. a heavy chain variable region comprising:
  iv. a CDR-H1 comprising SEQ ID NO: 4;
  v. a CDR-H2 comprising SEQ ID NO: 45 and
  vi. a CDR-H3 comprising SEQ ID NO: 46.

Preferably, the antibody or antigen-binding fragment thereof is humanized and prevents alpha synuclein aggregation induced by alpha synuclein fibrils, and more preferably binds to alpha synuclein to an epitope comprising, with reference to SEQ ID NO: 10, residues E123, Y125, E126, M127, P128, S129, E130 and E131, wherein the epitope optionally comprises A124 and G132.

In a preferred embodiment, the antibody or antigen-binding fragment thereof or a pharmaceutical composition comprising the antibody or antigen-binding fragment thereof for use in therapy, is an antibody or antigen-binding fragment thereof that binds alpha synuclein and comprises:
a. a light chain variable region comprising:
  i. a CDR-L1 comprising SEQ ID NO: 1;
  ii. a CDR-L2 comprising SEQ ID NO: 2 and
  iii. a CDR-L3 comprising to SEQ ID NO: 3; and
b. a heavy chain variable region comprising:
  iv. a CDR-H1 comprising SEQ ID NO: 4;
  v. a CDR-H2 comprising SEQ ID NO: 5 and
  vi. a CDR-H3 comprising SEQ ID NO: 6.

Preferably, the antibody or antigen-binding fragment thereof is humanized and prevents alpha synuclein aggregation induced by alpha synuclein fibrils, and more preferably binds to alpha synuclein to an epitope comprising, with reference to SEQ ID NO: 10, residues E123, Y125, E126, M127, P128, S129, E130 and E131, wherein the epitope optionally comprises A124 and G132.

In particular, the use in therapy comprises the use in the treatment of one or more alpha synucleinopathies.

In yet another aspect, the present invention provides for method of treating one or more synucleinopathies in a patient comprising administering to said patient a therapeutically effective amount of the antibody or antigen-binding fragment thereof according to the present invention or a pharmaceutical composition comprising the antibody or antigen-binding fragment thereof, wherein the antibody or antigen-binding fragment thereof binds alpha synuclein and comprises:
a. a light chain variable region comprising:
  i. a CDR-L1 comprising SEQ ID NO: 44;
  ii. a CDR-L2 comprising SEQ ID NO: 2 and
  iii. a CDR-L3 comprising to SEQ ID NO: 3; and
b. a heavy chain variable region comprising:
  iv. a CDR-H1 comprising SEQ ID NO: 4;
  v. a CDR-H2 comprising SEQ ID NO: 45 and
  vi. a CDR-H3 comprising SEQ ID NO: 46.

Preferably, the antibody or antigen-binding fragment thereof is humanized and prevents alpha synuclein aggregation induced by alpha synuclein fibrils, and more preferably binds to alpha synuclein to an epitope comprising, with reference to SEQ ID NO: 10, residues E123, Y125, E126, M127, P128, S129, E130 and E131, wherein the epitope optionally comprises A124 and G132.

In one preferred embodiment, the antibody or antigen-binding fragment thereof or a pharmaceutical composition comprising the antibody or antigen-binding fragment thereof is for use in the treatment of one or more alpha synucleinopathies, wherein the antibody or antigen-binding fragment thereof binds alpha synuclein and comprises:
a. a light chain variable region comprising a CDR-L1 comprising SEQ ID NO: 1; a CDR-L2 comprising SEQ ID NO: 2 and a CDR-L3 comprising to SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
b. a light chain variable region comprising SEQ ID NO: 15 and a heavy variable region comprising SEQ ID NO: 31; or
c. a light chain comprising SEQ ID NO: 17 and a heavy chain comprising SEQ ID NO: 33.

Preferably, this antibody or antigen-binding fragment thereof is humanized and prevents alpha synuclein aggregation induced by alpha synuclein fibrils, and more preferably binds to alpha synuclein to an epitope comprising, with reference to SEQ ID NO: 10, residues E123, Y125, E126, M127, P128, S129, E130 and E131, wherein the epitope optionally comprises A124 and G132.

In another preferred embodiment, the present invention provides for a method of treating one or more alpha synucleinopathies in a patient comprises administering to said patient a therapeutically effective amount of the antibody or antigen-binding fragment thereof according to the present invention or a pharmaceutical composition comprising the antibody or antigen-binding fragment thereof, wherein the antibody or antigen-binding fragment thereof binds alpha synuclein and comprises:
a. a light chain variable region comprising a CDR-L1 comprising SEQ ID NO: 1; a CDR-L2 comprising SEQ ID NO: 2 and a CDR-L3 comprising to SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
b. a light chain variable region comprising SEQ ID NO: 15 and a heavy variable region comprising SEQ ID NO: 31; or
c. a light chain comprising SEQ ID NO: 17 and a heavy chain comprising SEQ ID NO: 33.

Preferably, the antibody or antigen-binding fragment thereof is humanized and prevents alpha synuclein aggregation induced by alpha synuclein fibrils, and more preferably binds to alpha synuclein to an epitope comprising, with reference to SEQ ID NO: 10, residues E123, Y125, E126, M127, P128, S129, E130 and E131, wherein the epitope optionally comprises A124 and G132.

Alternatively, the antibody or antigen-binding fragment thereof or the pharmaceutical composition comprising the antibody or antigen-binding fragment thereof is for use in therapy or for use in the treatment of one or more alpha synucleinopathies and is an antibody or antigen-binding fragment thereof comprising:
a. a light chain variable region comprising a CDR-L1 comprising SEQ ID NO: 1 or SEQ ID NO: 7; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 or SEQ ID NO: 8 and a CDR-H3 comprising SEQ ID NO: 6 or SEQ ID NO: 9; or
b. a light chain variable region comprising SEQ ID NO: 15 or 19 and a heavy chain variable region comprising SEQ ID NO: 23 or SEQ ID NO: 27 or SEQ ID NO: 31 or SEQ ID NO: 35; or c. a light chain comprising SEQ ID NO: 17 or SEQ ID NO: 21 and a heavy chain comprising SEQ ID NO: 25 or SEQ ID NO: 29 or SEQ ID NO: 33 or SEQ ID NO: 37.

In another embodiment of the present invention, the method of treating one or more alpha synucleinopathies in a patient comprising administering to said patient a therapeutically effective amount of the antibody or antigen-binding fragment thereof according to the present invention or a pharmaceutical composition comprising the antibody or antigen-binding fragment thereof, wherein the antibody or antigen-binding fragment thereof binds alpha synuclein and comprises:
  a. a light chain variable region comprising a CDR-L1 comprising SEQ ID NO: 1 or SEQ ID NO: 7; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 or SEQ ID NO: 8 and a CDR-H3 comprising SEQ ID NO: 6 or SEQ ID NO: 9; or
  b. a light chain variable region comprising SEQ ID NO: 15 or 19 and a heavy chain variable region comprising SEQ ID NO: 23 or SEQ ID NO: 27 or SEQ ID NO: 31 or SEQ ID NO: 35; or
  c. a light chain comprising SEQ ID NO: 17 or SEQ ID NO: 21 and a heavy chain comprising SEQ ID NO: 25 or SEQ ID NO: 29 or SEQ ID NO: 33 or SEQ ID NO: 37.

Alpha synucleinopathies according to the present invention comprise, but are not limited to, Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1). Preferably, the alpha synucleinopathy is Parkinson's disease (PD).

In another embodiment, the antibody or antigen-binding fragment thereof or the pharmaceutical composition comprising the antibody or antigen-binding fragment thereof is for use in treating Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), preferably Parkinson's disease (PD), and is an antibody or antigen-binding fragment thereof comprising:
  a. a light chain variable region comprising a CDR-L1 comprising SEQ ID NO: 1; a CDR-L2 comprising SEQ ID NO: 2 and a CDR-L3 comprising to SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
  b. a light chain variable region comprising SEQ ID NO: 15 and a heavy variable region comprising SEQ ID NO: 31; or
  c. a light chain comprising SEQ ID NO: 17 and a heavy chain comprising SEQ ID NO: 33.

In another embodiment, the antibody or antigen-binding fragment thereof or the pharmaceutical composition comprising the antibody or antigen-binding fragment thereof is for use in treating Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), preferably Parkinson's disease (PD), and is an antibody or antigen-binding fragment thereof comprising:
  a. a light chain variable region comprising a CDR-L1 comprising SEQ ID NO: 1 or SEQ ID NO: 7; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 or SEQ ID NO: 8 and a CDR-H3 comprising SEQ ID NO: 6 or SEQ ID NO: 9; or
  b. a light chain variable region comprising SEQ ID NO: 15 or 19 and a heavy chain variable region comprising SEQ ID NO: 23 or SEQ ID NO: 27 or SEQ ID NO: 31 or SEQ ID NO: 35; or
  c. a light chain comprising SEQ ID NO: 17 or SEQ ID NO: 21 and a heavy chain comprising SEQ ID NO: 25 or SEQ ID NO: 29 or SEQ ID NO: 33 or SEQ ID NO: 37.

In another embodiment, there is provided a method of treating Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), preferably Parkinson's disease (PD), in a patient comprising administering to said patient a therapeutically effective amount of an antibody or antigen-binding fragment thereof or a pharmaceutical composition comprising the antibody or antigen-binding fragment thereof, wherein the antibody or antigen-binding fragment thereof comprises:
  a. a light chain variable region comprising a CDR-L1 comprising SEQ ID NO: 1; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
  b. a light chain variable region comprising SEQ ID NO: 15 and a heavy variable region comprising SEQ ID NO: 31; or
  c. a light chain comprising SEQ ID NO: 17 and a heavy chain comprising SEQ ID NO: 33.

In another embodiment, the method of treating Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), preferably Parkinson's disease (PD), in a patient comprises administering to said patient a therapeutically effective amount of an antibody or antigen-binding fragment thereof or a pharmaceutical composition comprising the antibody or antigen-binding fragment thereof, wherein the antibody or antigen-binding fragment thereof comprises:
  a. a light chain variable region comprising a CDR-L1 comprising SEQ ID NO: 1 or SEQ ID NO: 7; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 or SEQ ID NO: 8 and a CDR-H3 comprising SEQ ID NO: 6 or SEQ ID NO: 9; or
b. a light chain variable region comprising SEQ ID NO: 15 or 19 and a heavy chain variable region comprising SEQ ID NO: 23 or SEQ ID NO: 27 or SEQ ID NO: 31 or SEQ ID NO: 35; or
c. a light chain comprising SEQ ID NO: 17 or SEQ ID NO: 21 and a heavy chain comprising SEQ ID NO: 25 or SEQ ID NO: 29 or SEQ ID NO: 33 or SEQ ID NO: 37.

Alternatively, the invention also provides for the use of an antibody or an antigen-binding fragment thereof for the manufacture of a medicament for treating an alpha synucleinopathy, wherein the alpha synucleinopathy is preferably Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), more preferably Parkinson's disease (PD), wherein the antibody or antigen-binding fragment thereof comprises:
a. a light chain variable region comprising a CDR-L1 comprising SEQ ID NO: 1; a CDR-L2 comprising SEQ ID NO: 2 and a CDR-L3 comprising to SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
b. a light chain variable region comprising SEQ ID NO: 15 and a heavy variable region comprising SEQ ID NO: 31; or
c. a light chain comprising SEQ ID NO: 17 and a heavy chain comprising SEQ ID NO: 33.

Also part of the present invention is the use of the anti-alpha synuclein antibodies or antigen-binding fragments for use as diagnostically active agents or in diagnostic assays, for example for diagnosing alpha synucleinopathies such as Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1).

The diagnosis may preferably be performed on biological samples. A "biological sample" encompasses a variety of sample types obtained from an individual and can be used in a diagnostic or monitoring assay. The definition encompasses cerebrospinal fluid, blood such as plasma and serum, and other liquid samples of biological origin such as urine and saliva, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides.

Diagnostic testing may preferably be performed on biological samples which are not in contact with the human or animal body. Such diagnostic testing is also referred to as in vitro testing. In vitro diagnostic testing may rely on an in vitro method of detecting alpha synuclein in a biological sample which has been obtained from an individual comprising the steps of i) contacting the biological sample with anti-alpha synuclein antibody or antigen-binding fragment thereof as described herein; and ii) detecting binding of the anti-alpha synuclein antibody or antigen-binding fragment thereof to alpha synuclein. By comparing the detected alpha synuclein level or the presence of a specific post-translationally modified form of alpha synuclein with a suitable control, one or more alpha synucleinopathies may be identified. Such a detection method can thus be used to determine whether a subject has, or is at risk of developing, an alpha synucleinopathy, including determining the stage (severity) of an alpha synucleinopathy.

Therefore, the present invention provides for an antibody or antigen-binding fragment thereof for use in the diagnosis of alpha synucleinopathies, preferably in the diagnosis or Parkinson's disease, wherein the antibody or antigen-binding fragment thereof binds alpha synuclein and comprises:
a. a light chain variable region comprising a CDR-L1 comprising SEQ ID NO: 44; a CDR-L2 comprising SEQ ID NO: 2 and a CDR-L3 comprising to SEQ ID NO: 3; and a heavy chain variable region comprising a CDR-H1 comprising SEQ ID NO: 4; a CDR-H2 comprising SEQ ID NO: 45 and a CDR-H3 comprising SEQ ID NO: 46.

Preferably, the antibody or antigen-binding fragment thereof for use in the diagnosis of alpha synucleinopathies, preferably in the diagnosis or Parkinson's disease, wherein the antibody or antigen-binding fragment thereof binds alpha synuclein and comprises:
a. a light chain variable region comprising a CDR-L1 comprising SEQ ID NO: 1; a CDR-L2 comprising SEQ ID NO: 2 and a CDR-L3 comprising to SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
b. a light chain variable region comprising SEQ ID NO: 15 and a heavy variable region comprising SEQ ID NO: 31; or
c. a light chain comprising SEQ ID NO: 17 and a heavy chain comprising SEQ ID NO: 33.

The sequences included in the present invention are shown in Table 1:

TABLE 1

| Name | SEQ ID NO: | SEQUENCE |
|---|---|---|
| CDR-L1 | 1 | QASQSVYKNNYLA |
| CDR-L2 | 2 | GASTLAS |
| CDR-L3 | 3 | AGYKGGRNDGFA |
| CDR-H1 | 4 | GIDLSSHDMY |

TABLE 1 -continued

| Name | SEQ ID NO: | SEQUENCE |
|---|---|---|
| CDR-H2 | 5 | AIYASGSTYYASWAKG |
| CDR-H3 | 6 | IHYGNSGGL |
| CDR-L1 N33R | 7 | QASQSVYKNRYLA |
| CDR-H2 S56N | 8 | AIYASGNTYYASWAKG |
| CDR-H3 N102H | 9 | IHYGHSGGL |
| Human alpha synuclein P37840 | 10 | MDVFMKGLSKAKEGVVAAAEKTKQGVAEAAGKTKEGVLYVGSKTKEGVVHGVAT VAEKTKEQVTNVGGAVVTGVTAVAQKTVEGAGSIAAATGFVKKDQLGKNEEGAP QEGILEDMPVDPDNEAYEMPSEEGYQDYEPEA |
| Rabbit VL | 11 | AIVMTQTPSSKSVAVGDTVTINCQASQSVYKNNYLAWFQQKPGQPPKQLIYGAS TLASGVPSRFKGSGSGTQFTLTISDVVCDDAATYYCAGYKGGRNDGFAFGGGTE VVVK |
| Rabbit VL nucleotide | 12 | Gccatcgtgatgacccagactccatcttccaagtctgtcgctgtgggagacaca gtcaccatcaattgccaggccagtcagagtgtttataagaacaactacttagcc tggtttcaacagaaaccagggcagcctcccaaaacaactgatctatggtgcgtcc actctggcatctggggtcccatcgcggttcaaaggcagtggatctgggacacag ttcactctcaccatcagcgatgtggtgtgtgacgatgctgccacttactactgt gcaggatataaaggtggtcgtaatgatggttttgctttcggcggagggaccgag gtggtggtcaaa |
| Rabbit VH | 13 | QSVEESGGRLVTPGTPLTLTCTVSGIDLSSHDMYWVRQAPGKGLEYIGAIYASG STYYASWAKGRFTISKTSTTVDLKMTSLTTEDTATYFCARIHYGNSGGLWGQGT LVTVSS |
| Rabbit VH nucleotide | 14 | Cagtcggtggaggagtccggggggtcgcctggtcacgcctgggacacccctgaca ctcacctgcacagtctctggaatcgacctcagtagccacgacatgtattgggtc cgccaggctccagggaaggggctggaatacattggagccatttatgctagtggt agcacatactacgcgagctgggcgaaaggccgattcaccatctccaagacctcg accacggtggatctgaaaatgaccagtctgacaacggaggacacggccacctat ttctgtgccagaattcattatggtaatagtggtgggttgtggggccaaggcacc ctggtcaccgtctcgagt |
| 6470 gL3 VL | 15 | DIQMTQSPSSLSASVGDRVTITCQASQSVYKNNYLAWFQQKPGKAPKQLIYGAS TLASGVPSRFSGSGSGTQFTLTISSLQPEDFATYYCAGYKGGRNDGFAFGGGTK VEIK |
| 6470 gL3 VL nucl. | 16 | Gacattcagatgacccagtcccttcatcactgtccgcgagcgtgggcgacaga gtgaccattacgtgccaagccagccagtccgtgtacaagaacaactacctggcc tggttccagcaaaagcccgggaaggcgccaaaacagcttatctacggtgcatcc actctcgcctcgggagtgccgagccgcttctcgggatctgggtccggaactcag ttcacccctgactatctcgtccctgcaacccgaggatttcgccacctactactgc gccggctataagggaggacggaacgacggcttcgcttttggtggaggcaccaag gtcgaaatcaag |
| 6470 gL3 Light chain | 17 | DIQMTQSPSSLSASVGDRVTITCQASQSVYKNNYLAWFQQKPGKAPKQLIYGAS TLASGVPSRFSGSGSGTQFTLTISSLQPEDFATYYCAGYKGGRNDGFAFGGGTK VEIKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFNR GEC |
| 6470 gL3 Light chain nucl. | 18 | Gacattcagatgacccagtcccttcatcactgtccgcgagcgtgggcgacaga gtgaccattacgtgccaagccagccagtccgtgtacaagaacaactacctggcc tggttccagcaaaagcccgggaaggcgccaaaacagcttatctacggtgcatcc actctcgcctcgggagtgccgagccgcttctcgggatctgggtccggaactcag ttcacccctgactatctcgtccctgcaacccgaggatttcgccacctactactgc gccggctataagggaggacggaacgacggcttcgcttttggtggaggcaccaag gtcgaaatcaagcgtacggtggccgctcccctccgtgttcatcttcccaccctcc gacgagcagctgaagtccggcaccgcctccgtcgtgtgcctgctgaacaacttc taccccgcgaggccaaggtgcagtggaaggtggacaacgccctgcagtccggc aactcccaggaatccgtcaccgagcaggactccaaggacagcacctactccctg tcctcacccctgaccctgtccaaggccgactacgagaagcacaaggtgtacgcc tgcgaagtgacccaccagggcctgtccagccccgtgaccaagtccttcaaccgg ggcgagtgc |

TABLE 1 -continued

| Name | SEQ ID NO: | SEQUENCE |
|---|---|---|
| 6470 gL3 VL N33R | 19 | DIQMTQSPSSLSASVGDRVTITCQASQSVYKNRYLAWFQQKPGKAPKQLIYGAS TLASGVPSRFSGSGSGTQFTLTISSLQPEDFATYYCAGYKGGRNDGFAFGGGTK VEIK |
| 6470 gL3 VL N33R nucl. | 20 | Gacattcagatgacccagtccccttcatcactgtccgcgagcgtgggcgacaga gtgaccattacgtgccaagccagccagtccgtgtacaagaaccgttacctggcc tggttccagcaaaagcccgggaaggcgccaaaacagcttatctacggtgcatcc actctcgcctcgggagtgccgagccgcttctcgggatctgggtccggaactcag ttcaccctgactatctcgtccctgcaacccgaggatttcgccacctactactgc gccggctataagggaggacggaacgacggcttcgcttttggtggaggcaccaag gtcgaaatcaag |
| 6470 gL3 Light chain N33R | 21 | DIQMTQSPSSLSASVGDRVTITCQASQSVYKNRYLAWFQQKPGKAPKQLIYGAS TLASGVPSRFSGSGSGTQFTLTISSLQPEDFATYYCAGYKGGRNDGFAFGGGTK VEIKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFNR GEC |
| 6470 gL3 Light chain N33R nucl. | 22 | Gacattcagatgacccagtccccttcatcactgtccgcgagcgtgggcgacaga gtgaccattacgtgccaagccagccagtccgtgtacaagaaccgttacctggcc tggttccagcaaaagcccgggaaggcgccaaaacagcttatctacggtgcatcc actctcgcctcgggagtgccgagccgcttctcgggatctgggtccggaactcag ttcaccctgactatctcgtccctgcaacccgaggatttcgccacctactactgc gccggctataagggaggacggaacgacggcttcgcttttggtggaggcaccaag gtcgaaatcaagcgtacggtggccgctcccctccgtgttcatcttcccaccctcc gacgagcagctgaagtccggcaccgcctcgtcgtgtgcctgctgaacaacttc taccccgcgaggccaaggtgcagtggaaggtggacaacgccctgcagtccggc aactcccaggaatccgtcaccgagcaggactccaaggacagcacctactcctg tcctccaccctgaccctgtccaaggccgactacgagaagcacaaggtgtacgcc tgcgaagtgacccaccagggcctgtccagcccgtgaccaagtccttcaaccgg ggcgagtgc |
| 6470 gH23 VH | 23 | EVQLLESGGGLVQPGGSLRLSCAVSGIDLSSHDMYWVRQAPGKGLEYIGAIYAS GSTYYASWAKGRFTISRDNSKNTVYLQMNSLRAEDTAVYYCARIHYGNSGGLWG QGTLVTVSS |
| 6470 gH23 VH nucl | 24 | Gaggttcagctgctggagtctggaggcgggcttgtccagcctggagggagcctg cgtctctcttgtgcagtaagcggcatcgacctgtccagccacgacatgtattgg gtacgtcaggcaccgggtaaaggtctggaatacatcggcgccatttatgctagt ggtagcacatactacgcgagctgggcgaaaggccgtttcaccatctcccgtgac aactctaaaaacaccgtgtacctgcagatgaactctctgcgtgcggaagacact gcggtttactattgcgcgcgtattcattatggtaatagtggtgggttgtgggt cagggtactctggttaccgtctcgagc |
| 6470 gH23 Heavy chain | 25 | EVQLLESGGGLVQPGGSLRLSCAVSGIDLSSHDMYWVRQAPGKGLEYIGAIYAS GSTYYASWAKGRFTISRDNSKNTVYLQMNSLRAEDTAVYYCARIHYGNSGGLWG QGTLVTVSSASTKGPSVFPLAPCSRSTSESTAALGCLVKDYFPEPVTVSWNSGA LTSGVHTFPAVLQSSGLYSLSSVVTVPSSSLGTKTYTCNVDHKPSNTKVDKRVE SKYGPPCPPCPAPEFLGGPSVFLFPPKPKDTLMISRTPEVTCVVVDVSQEDPEV QFNWYVDGVEVHNAKTKPREEQFNSTYRVVSVLTVLHQDWLNGKEYKCKVSNKG LPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHNH YTQKSLSLSLGK |
| 6470 gH23 Heavy chain nucl. | 26 | gaggttcagctgctggagtctggaggcgggcttgtccagcctggagggagcctg cgtctctcttgtgcagtaagcggcatcgacctgtccagccacgacatgtattgg gtacgtcaggcaccgggtaaaggtctggaatacatcggcgccatttatgctagt ggtagcacatactacgcgagctgggcgaaaggccgtttcaccatctcccgtgac aactctaaaaacaccgtgtacctgcagatgaactctctgcgtgcggaagacact gcggtttactattgcgcgcgtattcattatggtaatagtggtgggttgtgggt cagggtactctggttaccgtctcgagcgcttctacaaagggcccctccgtgttc cctctggccccttgctccggtccacctcgagctacctcgagtcctctgggctgc ctggtcaaggactacttccccgagcccgtgacagtgtcctggaactctggcgcc ctgacctccggcgtgcacaccttccctgccgtgctgcagtcctccggcctgtac tccctgtcctccgtcgtgaccgtgccctcctccagcctgggcaccaagacctac acctgtaacgtggaccacaaagcctccaacaccaaggtggacaagcgggtggaa tctaagtacggccccctgcccccctgccctgcccctgaatttctgggcgga cctccgtgttcctgttcccccaaagcccaaggacaccctgatgatctcccgg acccccgaagtgacctgcgtggtggtggacgtgtcccaggaagatcccgaggtc cagttcaattggtacgtggacggcgtggaagtgcacaatgccaagaccaagccc agagaggaacagttcaactccacctaccgggtggtgtccgtgctgaccgtgctg caccaggactggctgaacggcaaagagtacaagtgcaaggtgtccaacaagggc ctgccctccagcatcgaaaagaccatctccaaggccaagggccagccccgcgag ccccaggtgtacaccctgccccctagccaggaagagatgaccaagaaccaggtg tccctgacctgtctggtcaagggcttctaccccctccgacattgccgtggaatgg TABLE 1 -continued

| Name | SEQ ID NO: | SEQUENCE |
|---|---|---|
| | | gagtccaacggccagcccgagaacaactacaagaccacccccctgtgctggac<br>agcgacggctccttcttcctgtactctcggctgaccgtggacaagtcccggtgg<br>caggaaggcaacgtcttctcctgctccgtgatgcacgaggccctgcacaaccac<br>tacacccagaagtccctgtccctgagcctgggcaag |
| 6470 gH23 VH S56N N102H | 27 | EVQLLESGGGLVQPGGSLRLSCAVSGIDLSSHDMYWVRQAPGKGLEYIGAIYAS<br>GNTYYASWAKGRFTISRDNSKNTVYLQMNSLRAEDTAVYYCARIHYGHSGGLWG<br>QGTLVTVSS |
| 6470 gH23 VH S56N N102H nucl. | 28 | Gaggttcagctgctggagtctggaggcgggcttgtccagcctggagggagcctg<br>cgtctctcttgtgcagtaagcggcatcgacctgtccagccacgacatgtattgg<br>gtacgtcaggcaccgggtaaaggtctggaatacatcggcgccatttatgctagt<br>ggtaatacatactacgcgagctgggcgaaaggccgtttcaccatctcccgtgac<br>aactctaaaaacaccgtgtacctgcagatgaactctctgcgtgcggaagacact<br>gcggtttactattgcgcgcgtattcattatggtcacagtggtgggttgtgggt<br>cagggtactctggttaccgtctcgagc |
| 6470 gH23 Heavy chain S56N N102H | 29 | EVQLLESGGGLVQPGGSLRLSCAVSGIDLSSHDMYWVRQAPGKGLEYIGAIYAS<br>GNTYYASWAKGRFTISRDNSKNTVYLQMNSLRAEDTAVYYCARIHYGHSGGLWG<br>QGTLVTVSSASTKGPSVFPLAPCSRSTSESTAALGCLVKDYFPEPVTVSWNSGA<br>LTSGVHTFPAVLQSSGLYSLSSVVTVPSSSLGTKTYTCNVDHKPSNTKVDKRVE<br>SKYGPPCPPCPAPEFLGGPSVFLFPPKPKDTLMISRTPEVTCVVVDVSQEDPEV<br>QFNWYVDGVEVHNAKTKPREEQFNSTYRVVSVLTVLHQDWLNGKEYKCKVSNKG<br>LPSSIEKTISKAKGQPREPQVYTLPPSQEEMTKNQVSLTCLVKGFYPSDIAVEW<br>ESNGQPENNYKTTPPVLDSDGSFFLYSRLTVDKSRWQEGNVFSCSVMHEALHNH<br>YTQKSLSLSLGK |
| 6470 gH23 Heavy chain S56N N102H nucl. | 30 | gaggttcagctgctggagtctggaggcgggcttgtccagcctggagggagcctg<br>cgtctctcttgtgcagtaagcggcatcgacctgtccagccacgacatgtattgg<br>gtacgtcaggcaccgggtaaaggtctggaatacatcggcgccatttatgctagt<br>ggtaatacatactacgcgagctgggcgaaaggccgtttcaccatctcccgtgac<br>aactctaaaaacaccgtgtacctgcagatgaactctctgcgtgcggaagacact<br>gcggtttactattgcgcgcgtattcattatggtcacagtggtgggttgtgggt<br>cagggtactctggttaccgtctcgagcgcttctacaaagggcccctccgtgttc<br>cctctggccccttgctcccggtccacctccgagtctaccgccgctctgggctgc<br>ctggtcaaggactacttccccgagcccgtgacagtgtcctggaactctggcgcc<br>ctgacctccggcgtgcacaccttccctgccgtgctgcagtcctccggcctgtac<br>tccctgtcctccgtcgtgaccgtgccctcctccagcctgggcaccaagacctac<br>acctgtaacgtggaccacaagccctccaacaccaaggtggacaagcgggtggaa<br>tctaagtacggcccctccctgccccccctgccctgccctgaatttctgggcgga<br>ccttccgtgttcctgttcccccccaaagcccaaggacacccctgatgatctcccgg<br>acccccgaagtgacctgcgtggtggtggacgtgtcccaggaagatcccgaggtc<br>cagttcaattggtacgtggacggcgtggaagtgcacaatgccaagaccaagccc<br>agagaggaacagttcaactccacctaccgggtggtgtccgtgctgaccgtgctg<br>caccaggactggctgaacggcaaagagtacaagtgcaaggtgtccaacaagggc<br>ctgccctccagcatcgaaaagaccatctccaaggccaagggccagccccgcgag<br>ccccaggtgtacaccctgccccctagccaggaagagatgaccaagaaccaggtg<br>tccctgacctgtctggtcaagggcttctaccccctccgacattgccgtggaatgg<br>gagtccaacggccagcccgagaacaactacaagaccacccccctgtgctggac<br>agcgacggctccttcttcctgtactctcggctgaccgtggacaagtcccggtgg<br>caggaaggcaacgtcttctcctgctccgtgatgcacgaggccctgcacaaccac<br>tacacccagaagtccctgtccctgagcctgggcaag |
| 6470 gH36 VH | 31 | EVQLLESGGGLVQPGGSLRLSCAVSGIDLSSHDMYWVRQAPGKGLEYIGAIYAS<br>GSTYYASWAKGRFTISRDSSKNTLYLQMNSLRAEDTAVYYCARIHYGNSGGLWG<br>QGTLVTVSS |
| 6470 gH36 VH nucl | 32 | Gaggttcagctgctggagtctggaggcgggcttgtccagcctggagggagcctg<br>cgtctctcttgtgcagtaagcggcatcgacctgtccagccacgacatgtattgg<br>gtacgtcaggcaccgggtaaaggtctggaatacatcggcgccatttatgctagt<br>ggtagcacatactacgcgagctgggcgaaaggccgtttcaccatctcccgtgac<br>tccagcaaaaacaccctgtacctgcagatgaactctctgcgtgcggaagacact<br>gcggtttactattgcgcgcgtattcattatggtaatagtggtgggttgtgggt<br>cagggtactctggttaccgtctcgagc |
| 6470 gH36 Heavy chain | 33 | EVQLLESGGGLVQPGGSLRLSCAVSGIDLSSHDMYWVRQAPGKGLEYIGAIYAS<br>GSTYYASWAKGRFTISRDSSKNTLYLQMNSLRAEDTAVYYCARIHYGNSGGLWG<br>QGTLVTVSSASTKGPSVFPLAPCSRSTSESTAALGCLVKDYFPEPVTVSWNSGA<br>LTSGVHTFPAVLQSSGLYSLSSVVTVPSSSLGTKTYTCNVDHKPSNTKVDKRVE<br>SKYGPPCPPCPAPEFLGGPSVFLFPPKPKDTLMISRTPEVTCVVVDVSQEDPEV<br>QFNWYVDGVEVHNAKTKPREEQFNSTYRVVSVLTVLHQDWLNGKEYKCKVSNKG<br>LPSSIEKTISKAKGQPREPQVYTLPPSQEEMTKNQVSLTCLVKGFYPSDIAVEW<br>ESNGQPENNYKTTPPVLDSDGSFFLYSRLTVDKSRWQEGNVFSCSVMHEALHNH<br>YTQKSLSLSLGK |

TABLE 1 -continued

| Name | SEQ ID NO: | SEQUENCE |
|---|---|---|
| 6470 gH36 Heavy chain nucl. | 34 | gaggttcagctgctggagtctggaggcgggcttgtccagcctggagggagcctg<br>cgtctctcttgtgcagtaagcggcatcgacctgtccagccacgacatgtattgg<br>gtacgtcaggcaccgggtaaaggtctggaatacatcggcgccatttatgctagt<br>ggtagcacatactacgcgagctgggcgaaaggccgtttcaccatctcccgtgac<br>tccagcaaaaacaccctgtacctgcagatgaactctctgcgtgcggaagacact<br>gcggtttactattgcgcgcgtattcattatggtaatagtggtgggttgtgggt<br>cagggtactctggttaccgtctcgagcgcttctacaaagggcccctccgtgttc<br>cctctggcccttgctcccggtccacctccgagtctaccgccgctctgggctgc<br>ctggtcaaggactacttccccgagcccgtgacagtgtcctggaactctggcgcc<br>ctgacctccggcgtgcacaccttccctgccgtgctgcagtcctccggcctgtac<br>tccctgtcctccgtcgtgaccgtgccctcctccagcctgggcaccaagacctac<br>acctgtaacgtggaccacaagcctccaacaccaaggtggacaagcgggtggaa<br>tctaagtacggcccctccctgccccctgccctgccctgaatttctgggcgga<br>ccttccgtgttcctgttccccccaaagcccaaggacaccctgatgatctcccgg<br>accccgaagtgacctgcgtggtggtggacgtgtcccaggaagatcccgaggtc<br>cagttcaattggtacgtggacggcgtggaagtgcacaatgccaagaccaagccc<br>agagaggaacagttcaactccacctaccgggtggtgtccgtgctgaccgtgctg<br>caccaggactggctgaacggcaaagagtacaagtgcaaggtgtccaacaagggc<br>ctgcccctccagcatcgaaaagaccatctccaaggccaagggccagcccgcgag<br>ccccaggtgtacaccctgcccccctagccaggaagagatgaccaagaaccaggtg<br>tccctgacctgtctggtcaagggcttctaccccctcgacattgccgtggaatgg<br>gagtccaacggccagcccgagaacaactacaagaccacccccctgtgctggac<br>agcgacggctccttcttcctgtactctcggctgaccgtggacaagtcccggtgg<br>caggaaggcaacgtcttctcctgctccgtgatgcacgaggccctgcacaaccac<br>tacacccagaagtccctgtccctgagcctgggcaag |
| 6470 gH36 VH S56N N102H | 35 | EVQLLESGGGLVQPGGSLRLSCAVSGIDLSSHDMYWVRQAPGKGLEYIGAIYAS<br>GNTYYASWAKGRFTISRDSSKNTLYLQMNSLRAEDTAVYYCARIHYGHSGGLWG<br>QGTLVTVSS |
| 6470 gH36 VH S56N N102H nucl. | 36 | Gaggttcagctgctggagtctggaggcgggcttgtccagcctggagggagcctg<br>cgtctctcttgtgcagtaagcggcatcgacctgtccagccacgacatgtattgg<br>gtacgtcaggcaccgggtaaaggtctggaatacatcggcgccatttatgctagt<br>ggtaatacatactacgcgagctgggcgaaaggccgtttcaccatctcccgtgac<br>tccagcaaaaacaccctgtacctgcagatgaactctctgcgtgcggaagacact<br>gcggtttactattgcgcgcgtattcattatggtcacagtggtgggttgtgggt<br>cagggtactctggttaccgtctcgagc |
| 6470 gH36 Heavy chain S56N N102H | 37 | EVQLLESGGGLVQPGGSLRLSCAVSGIDLSSHDMYWVRQAPGKGLEYIGAIYAS<br>GNTYYASWAKGRFTISRDSSKNTLYLQMNSLRAEDTAVYYCARIHYGHSGGLWG<br>QGTLVTVSSASTKGPSVFPLAPCSRSTSESTAALGCLVKDYFPEPVTVSWNSGA<br>LTSGVHTFPAVLQSSGLYSLSSVVTVPSSSLGTKTYTCNVDHKPSNTKVDKRVE<br>SKYGPPCPPCPAPEFLGGPSVFLFPPKPKDTLMISRTPEVTCVVVDVSQEDPEV<br>QFNWYVDGVEVHNAKTKPREEQFNSTYRVVSVLTVLHQDWLNGKEYKCKVSNKG<br>LPSSIEKTISKAKGQPREPQVYTLPPSQEEMTKNQVSLTCLVKGFYPSDIAVEW<br>ESNGQPENNYKTTPPVLDSDGSFFLYSRLTVDKSRWQEGNVFSCSVMHEALHNH<br>YTQKSLSLSLGK |
| 6470 gH36 Heavy chain S56N N102H nucl. | 38 | gaggttcagctgctggagtctggaggcgggcttgtccagcctggagggagcctg<br>cgtctctcttgtgcagtaagcggcatcgacctgtccagccacgacatgtattgg<br>gtacgtcaggcaccgggtaaaggtctggaatacatcggcgccatttatgctagt<br>ggtaatacatactacgcgagctgggcgaaaggccgtttcaccatctcccgtgac<br>tccagcaaaaacaccctgtacctgcagatgaactctctgcgtgcggaagacact<br>gcggtttactattgcgcgcgtattcattatggtcacagtggtgggttgtgggt<br>cagggtactctggttaccgtctcgagcgcttctacaaagggcccctccgtgttc<br>cctctggcccttgctcccggtccacctccgagtctaccgccgctctgggctgc<br>ctggtcaaggactacttccccgagcccgtgacagtgtcctggaactctggcgcc<br>ctgacctccggcgtgcacaccttccctgccgtgctgcagtcctccggcctgtac<br>tccctgtcctccgtcgtgaccgtgccctcctccagcctgggcaccaagacctac<br>acctgtaacgtggaccacaagcctccaacaccaaggtggacaagcgggtggaa<br>tctaagtacggcccctccctgccccctgccctgccctgaatttctgggcgga<br>ccttccgtgttcctgttccccccaaagcccaaggacaccctgatgatctcccgg<br>accccgaagtgacctgcgtggtggtggacgtgtcccaggaagatcccgaggtc<br>cagttcaattggtacgtggacggcgtggaagtgcacaatgccaagaccaagccc<br>agagaggaacagttcaactccacctaccgggtggtgtccgtgctgaccgtgctg<br>caccaggactggctgaacggcaaagagtacaagtgcaaggtgtccaacaagggc<br>ctgcccctccagcatcgaaaagaccatctccaaggccaagggccagcccgcgag<br>ccccaggtgtacaccctgcccccctagccaggaagagatgaccaagaaccaggtg<br>tccctgacctgtctggtcaagggcttctaccccctcgacattgccgtggaatgg<br>gagtccaacggccagcccgagaacaactacaagaccacccccctgtgctggac<br>agcgacggctccttcttcctgtactctcggctgaccgtggacaagtcccggtgg<br>caggaaggcaacgtcttctcctgctccgtgatgcacgaggccctgcacaaccac<br>tacacccagaagtccctgtccctgagcctgggcaag |

TABLE 1 -continued

| Name | SEQ ID NO: | SEQUENCE |
|---|---|---|
| Human IGKV1-16 JK4 acceptor framework | 39 | DIQMTQSPSSLSASVGDRVTITCRASQGISNYLAWFQQKPGKAPKSLIYAASSL QSGVPSRFSGSGSGTDFTLTISSLQPEDFATYYCQQYNSYPLTFGGGTKVEIK |
| Human IGKV1-16 JK4 acceptor framework nucl. | 40 | Gacatccagatgacccagtctccatcctcactgtctgcatctgtaggagacaga gtcaccatcacttgtcgggcgagtcagggcattagcaattatttagcctggttt cagcagaaaccagggaaagcccctaagtccctgatctatgctgcatccagtttg caaagtggggtcccatcaaggttcagcggcagtggatctgggacagatttcact ctcaccatcagcagcctgcagcctgaagattttgcaacttattactgccaacag tataatagttaccctctcactttcggcggagggaccaaggtggagatcaaa |
| Human IGHV3-23 JH4 acceptor framework | 41 | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCAKYFDYWGQGTL VTVSS |
| Human IGHV3-23 JH4 acceptor framework nucl. | 42 | Gaggtgcagctgttggagtctgggggaggcttggtacagcctggggggtccctg agactctcctgtgcagcctctggattcacctttagcagctatgccatgagctgg gtccgccaggctccagggaaggggctggagtgggtctcagctattagtggtagt ggtggtagcacatactacgcagactccgtgaagggccggttcaccatctccaga gacaattccaagaacacgctgtatctgcaaatgaacagcctgagagccgaggac acggccgtatattactgtgcgaaatactttgactactggggccaaggaaccctg gtcaccgtctcctca |
| Rabbit Fc human 68-140 a-syn | 43 | GAVVTGVTAVAQKTVEGAGSIAAATGFVKKDQLGKNEEGAPQEGILEDMPVDPD NEAYEMPSEEGYQDYEPEAVEKTVAPSTCSKPTCPPPELLGGPSVFIFPPKPKD TLMISRTPEVTCVVVDVSQDDPEVQFTWYINNEQVRTARPPLREQQFNSTIRVV STLPIAHQDWLRGKEFKCKVHNKALPAPIEKTISKARGQPLEPKVYTMGPPREE LSSRSVSLTCMINGFYPSDISVEWEKNGKAEDNYKTTPAVLDSGSYFLYSKLS VPTSEWQRGDVFTCSVMHEALHNHYTQKSISRSPGK |
| CDR-L1 X33 | 44 | QASQSVYKNXYLA (x = N or R) |
| CDR-H2 X56 | 45 | AIYASGXTYYASWAKG (X = S or N) |
| CDR-H3 X102 | 46 | IHYGXSGGL (X = N or H) |
| 6470 rabbit light chain | 47 | AIVMTQTPSSKSVAVGDTVTINCQASQSVYKNNYLAWFQQKPGQPPKQLIYGAS TLASGVPSRFKGSGSGTQFTLTISDVVCDDAATYYCAGYKGGRNDGFAFGGGTE VVVKRTPVAPTVLIFPPAADQVATGTVTIVCVANKYFPDVTVTWEVDGTTQTTG IENSKTPQNSADCTYNLSSTLTLTSTQYNSHKEYTCKVTQGTTSVVQSFNRGDC |
| 6470 rabbit heavy chain | 48 | QSVEESGGRLVTPGTPLTLTCTVSGIDLSSHDMYWVRQAPGKGLEYIGAIYASG STYYASWAKGRFTISKTSTTVDLKMTSLTTEDTATYFCARIHYGNSGGLWGQGT LVTVSSGQPKAPSVFPLAPCCGDTPSSTVTLGCLVKGYLPEPVTVTWNSGTLTN GVRTFPSVRQSSGLYSLSSVVSVTSSSQPVTCNVAHPATNTKVDKTVAPSTCSK PTCPPPELLGGPSVFIFPPKPKDTLMISRTPEVTCVVVDVSQDDPEVQFTWYIN NEQVRTARPPLREQQFNSTIRVVSTLPTAHQDWLRGKEEKCKVHNKALPAPIEK TISKARGQPLEPKVYTMGPPREELSSRSVSLTCMINGFYPSDISVEWEKNGKAE DNYKTTPAVLDSGSYFLYSKLSVPTSEWQRGDVFTCSVMHEALHNHYTQKSIS RSPGK |
| 6470 rabbit Fab heavy chain | 49 | QSVEESGGRLVTPGTPLTLTCTVSGIDLSSHDMYWVRQAPGKGLEYIGAIYASG STYYASWAKGRFTISKTSTTVDLKMTSLTTEDTATYFCARIHYGNSGGLWGQGT LVTVSSGQPKAPSVFPLAPCCGDTPSSTVTLGCLVKGYLPEPVTVTWNSGTLTN GVRTFPSVRQSSGLYSLSSVVSVTSSSQPVTCNVAHPATNTKVDKTVAPSTCSK PHHHHHHHHHH |

The invention will now be further described by way of examples with references to embodiments illustrated in the accompanying drawings.

EXAMPLES

Example 1: Expression of Human Alpha Synuclein Monomer and Fibrils

A gene encoding human alpha-synuclein was generated synthetically and sub-cloned into vector pMH 10His TEV (containing a CMV promoter) using standard molecular biology techniques, to create a vector engineered to produce alpha synuclein with an N-terminal 10His-TEV tag. The resulting vector was transfected into Expi293F cells using the Expi293TM Expression System (Invitrogen), following manufacturer's protocols. Alpha synuclein protein accumulated in the culture media from where it was recovered using an immobilized metal ion affinity chromatography HisTrap excel column (GE Healthcare). The column was washed with 25 mM TrisHCl, 300 mM NaCl, pH8.0, and the protein eluted with a stepped gradient of 500 mM imidazole in the same buffer. The 10His tag was removed using TEV protease. The sample was then concentrated and desalted before reapplying the cleaved protein to the HisTrap excel column and collecting the cleaved alpha synuclein in the flow through. The alpha synuclein was further purified by gel filtration on a HiLoad 26/600 Superdex 75 column (GE Healthcare), and endotoxin removed by passage over a *Proteus* NoEndo cartridge (Generon). The purified alpha synuclein was confirmed to be monomeric by SEC MALS (FIG. 1A).

Figure 1B:
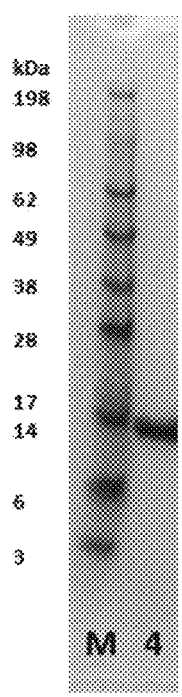

Wild type (un-tagged) human alpha-synuclein was also expressed in Expi293F cells. The protein was recovered from the culture media via anion exchange using a HiTrap Q column (GE Healthcare). The column was washed with 20 mM TrisHCl pH 8.0, and protein eluted using a sodium chloride gradient to 400 mM. Fractions were concentrated and desalted by passing over a HiPrep 26/10 column (GE Healthcare) and eluted with 20 mM TrisHCl pH 8.0. The protein was further purified using a MonoQ 10/100GL column, eluted with a sodium chloride gradient to 400 mM in 20 mM TrisHCl pH 8.0, followed by gel filtration on a HiLoad 26/600 Superdex 75 column (GE Healthcare), with elution in PBS pH 7.4 (FIG. 1B).

Figure 2A:
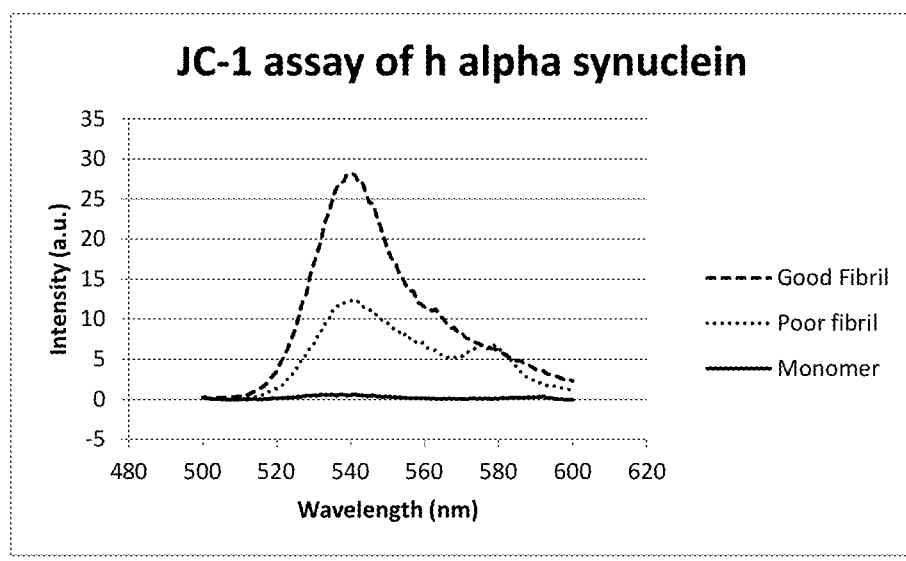
FIGS. 2A and 2B. (A) Fibril analysis by JC-1 assay of a monomer with no fluorescence and of fibrils with a maximum fluorescence at 540 nm. (B) Typical example for the random coil spectrum of monomeric human alpha-synuclein (wavelength 1646 cm$^{-1}$) and inter β-sheet formation in recombinant human alpha-synuclein fibrils (wavelength 1625-1630 cm$^{-1}$)
Figure 2B:
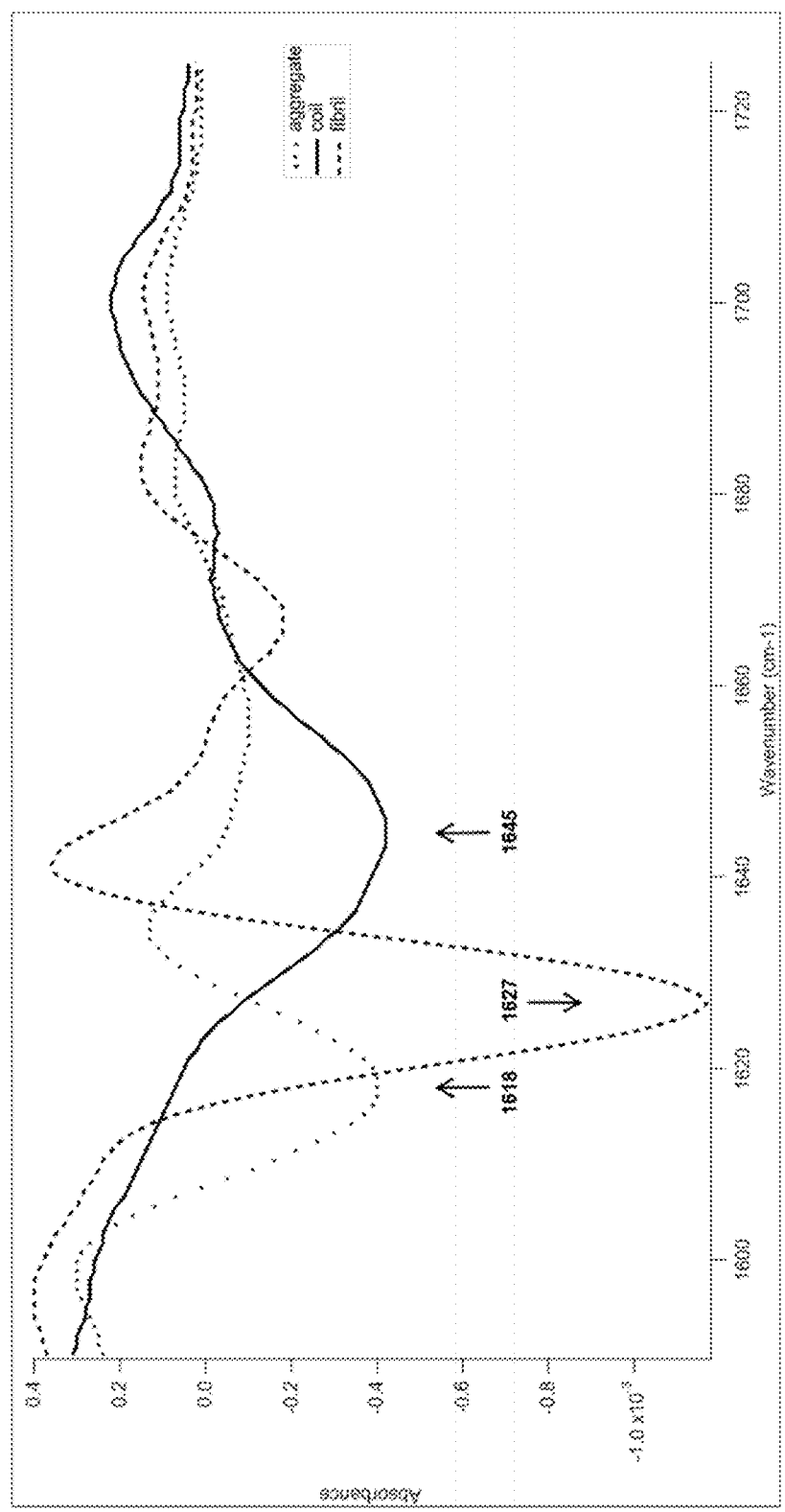

This wild type (un-tagged) alpha-synuclein monomer was used to prepare alpha-synuclein fibrils were obtained by agitating purified, recombinant alpha-synuclein monomer (9-10 mg/mL in PBS pH7.4) at 1200 rpm, 37° C. in a Vortemp56 shaking incubator (Labnet) continuously for 10 days. Fibril formation was assessed by JC-1 assay (Lee et al., Biochem. J. 2009, 418, 311-323), and C Fourier Transform Infrared spectroscopy of the solution. Unincorporated monomer in the fibril solutions was assessed by ultracentrifugation and by passage through a 100KDa cut-off membrane followed by gel electrophoresis. Only fibrils with a JC-1 response >15, low amount of soluble monomer (<5%) and a FTIR spectrum with the main absorption between 1625 and 1630 cm-1 were used in further studies (FIG. 2). The prepared fibrils were stored at −80° C.

Example 2: Immunization and Antibodies Isolation

Numerous immunization strategies using various species and immunogens were performed. Antibody 6470 was derived from a female New Zealand White rabbit (>2 kg) which had received sub-cutaneous immunization with a rabbit Fc fusion protein, comprising human alpha-synuclein residues 68-140 fused to rabbit Fc (SEQ ID NO: 43).

The alpha-synuclein (68-140) rabbit Fc fusion protein for immunization was expressed in Expi293F cells, using the Expi293TM Expression System (Invitrogen), following manufacturer's protocols. Protein was purified from the supernatant by affinity chromatography using a MabSelect-Sure column (GE Healthcare). The column was equilibrated with 50 mM Glycine/sodium Glycinate pH 8.8 buffer, and eluted with a gradient of 0.1M citric acid pH 2.0 in the same buffer. Protein fractions were neutralized with 2M Tris HCl pH8.5, concentrated and further purified by gel filtration on a HiLoad 26/600 Superdex 200 column (GE Healthcare) equilibrated and eluted in PBS pH 7.4. Rabbits received a primary immunization comprising 500 pg of the fusion protein emulsified in an equal volume of complete Freund's adjuvant (CFA). The rabbits were given 2 booster injections at 21-day intervals using incomplete Freund's adjuvant (IFA), with bleeds taken, from the ear, 14 days after immunization. Termination occurred 14 days after the final boost with single cell suspensions of spleen, bone marrow and peripheral blood mononuclear cells prepared and frozen in 10% dimethyl sulfoxide (DMSO) in fetal calf serum (FCS) at −80° C.

B Cell Culture

B cell cultures were prepared using a method similar to that described by Tickle et al., 2015. J Biomol Screen: 20 (4), 492-497. Briefly, lymph node or splenocyte derived B cells from immunized animals were cultured at a density of approximately 2000-5000 cells per well in bar-coded 96-well tissue culture plates with 200 µl/well RPMI 1640 medium (Gibco BRL) supplemented with 10% FCS (Sigma Aldrich), 2% HEPES (Sigma Aldrich), 1% L-Glutamine (Gibco BRL), 1% penicillin/streptomycin solution (Gibco BRL), 0.1% β-mercaptoethanol (Gibco BRL), 1% activated human PBMC supernatant (BSS) and X-ray irradiated mutant EL4 murine thymoma cells ($5 \times 10^4$/well) for seven days at 37° C. in an atmosphere of 5% $CO_2$. Cultures were set up using B cells from all animals immunized, and in total, approximately $1.7 \times 10^9$ B cells were sampled.

6470, an antibody according to the present invention, was generated from activated lymph node-derived B cells which were cultured at a density of approximately 5000 cells per well. Lymph node was used in addition to splenocytes for antibody discovery to give us an alternative source of B cells from which to sample and identify novel antibodies. Antibodies with related sequences were identified from B cells derived from the lymph node but not the spleen. Approximately $9.6 \times 10^7$ cells were sampled from the human alpha synuclein C-terminal protein immunized rabbit.

Primary Screening

The presence of human alpha synuclein-specific antibodies in B cell culture supernatants was determined using a homogeneous fluorescence-based binding assay using Superavidin™ beads (Bangs Laboratories) coated with biotinylated recombinant human alpha synuclein full length monomer as a source of target antigen. Recombinant human alpha synuclein as described herein was biotinylated using a 3-fold molar excess of biotin. A low molar excess of biotin was used in order to avoid complete modification of all seven lysine residues that reside within the alpha synuclein molecule. Alpha synuclein monomer was incubated overnight at 40° C. with the biotin and free biotin was removed the following day using a Zeba™ spin desalting column. Screening involved the transfer of 10 µl of supernatant from barcoded 96-well tissue culture plates into barcoded 384-well black-walled assay plates containing biotinylated recombinant human alpha synuclein monomer immobilized on Superavidin beads (10 µl/well) using an Agilent Bravo liquid handler. Binding was revealed with a goat anti-rabbit IgG Fcγ-specific Alexafluor647 conjugate (Jackson). Plates were read on a TTP Labtech Mirrorball in order to identify wells containing alpha synuclein-specific IgG.

Secondary Screening

Following primary screening, positive supernatants were consolidated on 96-well bar-coded master plates using a Beckman Coulter BiomekNXP hit-picking robot and B cells in cell culture plates frozen at −80° C. Master plates were then screened in a streptavidin-capture ELISA assay using biotinylated recombinant human alpha synuclein monomer or biotinylated recombinant human alpha synuclein fibrils. This was carried out to identify wells which gave binding to both monomeric and fibrillar recombinant human alpha synuclein, and to exclude any false positive wells showing off-target binding to the Superavidin™ beads. Given the insoluble nature of the fibrils, conventional ELISA coating protocols, that are used with proteins in solution, were not favored. It was decided that a minimal biotinylation protocol be employed to preserve the fibrillar structure and to facilitate efficient coating of the fibrils on an ELISA plate pre-coated with streptavidin.

Biotinylated alpha synuclein total fibrils were generated, as described herein, by combining biotinylated recombinant alpha synuclein monomer (as described above) with a 50-fold excess of unlabeled recombinant alpha synuclein in PBS. Fibril formation was confirmed by JC1 assay (Lee et al., Biochem. J. 2009, 418, 311-323).

Biotinylated monomer or biotinylated fibrils in PBS were captured onto 384-well Maxisorp plates coated with streptavidin in a carbonate coating buffer ($dH_2O+0.16\%$ $Na_2CO_3+0.3\%$ $NaHCO_3$.) Plates were blocked with 1% w/v PEG/PBS and then incubated with 10 µl/well of B cell culture supernatant (diluted 1:1 with blocking buffer.) Secondary HRP-conjugated goat anti-rabbit IgG Fc antibody (Stratech Scientific Ltd/Jackson ImmunoResearch) was added to plates, followed by visualization of binding with TMB substrate (3,3',5,5'-Tetramethylbenzidine, from EMD Millipore; 10 µl/well). The optical density was measured at 630 nM using BioTek Synergy 2 microplate reader. The primary binding assay identified 640 hits and following ELISA screening, 491 of those were shown to bind to both monomeric and fibrillar recombinant human alpha synuclein.

B cell supernatants demonstrating strongest ELISA binding signals to recombinant fibrils were selected for further analysis by surface plasmon resonance to identify those with the best off-rate on recombinant human alpha synuclein monomer, recombinant human alpha synuclein fibrils and recombinant mouse alpha synuclein fibrils. The supernatants from 80 different B cells were tested, nine wells gave off-rates (kd)<$1\times10^{-5}$ on recombinant human fibrils. Of these, seven gave off-rates (kd) of less than $1\times10^{-5}$ on recombinant mouse fibrils and two gave off-rates (kd) less than $1\times10^{-5}$ on recombinant human monomer. All nine supernatants were selected for variable region recovery.

Variable Region Recovery

To allow recovery of antibody variable region genes from a selection of supernatants of interest, a deconvolution step had to be performed to enable identification of the antigen-specific B cells in a given well that contained a heterogeneous population of B cells. This was achieved using the Fluorescent foci method (Clargo et al., 2014. MAbs: 6(1), 143-159). Briefly, Immunoglobulin-secreting B cells from a positive well were mixed with streptavidin beads (New England Biolabs) coated with biotinylated recombinant human alpha synuclein fibrils (generated using the 1:50 mix as described above) and a 1:1200 final dilution of a goat anti-rabbit Fcγ fragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube.

Antibody variable region genes were recovered from single cells by reverse transcription (RT)-PCR using heavy and light chain variable region-specific primers. Two rounds of PCR were performed with the nested 2° PCR incorporating restriction sites at the 3' and 5' ends allowing cloning of the variable region into a rabbit IgG (VH) or rabbit kappa (VL) mammalian expression vector. Anti-alpha synuclein antibody genes from 5 different supernatants were successfully cloned into expression vectors. Heavy and light chain constructs were co-transfected into Expi-293 cells using ExpiFectamine 293 (Invitrogen) and recombinant antibody expressed in 125 ml Erlenmeyer flask in a volume of 30 ml. After 5-7 days expression, supernatants were harvested and purified using affinity chromatography.

ELISA Screening of Transient Supernatants

Figure 3:
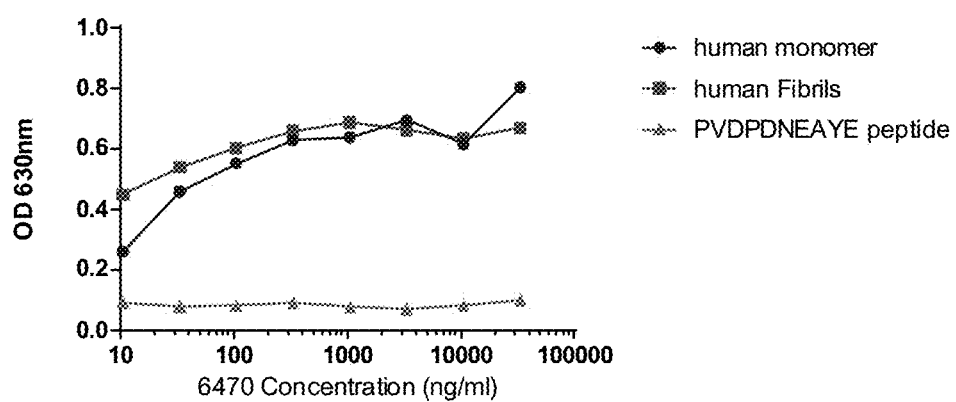
FIG. 3. ELISA binding assay. ELISA binding of rabbit 6470 IgG1 to recombinant human alpha synuclein monomer and fibrils and peptide PVDPDNEAYE of human alpha synuclein.

Purified antibodies were then subject to further screening by ELISA. Biotinylated recombinant human alpha synuclein monomer and fibrils were captured onto 384-well Maxisorp plates (ThermoScientific/Nunc) coated with streptavidin in carbonate coating buffer ($dH2O+0.16\%$ $Na_2CO_3+0.3\%$ $NaHCO_3$). Separate plates were also coated with a biotinylated peptide corresponding to residues 117 to 126 of human alpha synuclein according to SEQ ID NO: 10 (peptide PVDPDNEAYE) to check if transients bound to this or a different region on the molecule. Plates were blocked with 1% w/v PEG/PBS and then incubated with several dilutions of purified transient supernatant. Secondary HRP-conjugated goat anti-rabbit IgG Fc antibody (Stratech Scientific Ltd/Jackson ImmunoResearch) was added to plates, followed by visualization of binding with TMB substrate (3,3',5,5'-Tetramethylbenzidine, from EMD Millipore; 10 µl/well). The optical density was measured at 630 nM using BioTek Synergy 2 microplate reader. Data for 6470, is shown in FIG. 3. As can be seen, 6470 shows binding to both monomeric and fibrillar recombinant human alpha synuclein, but does not show binding to the 117-126 peptide.

Antibodies (IgG) were then tested in a cell-based aggregation assay as described later in example 7. The binding kinetics of all antibodies demonstrating activity in the cell assay were subsequently determined by surface plasmon resonance. The antibodies were tested as IgGs and Fabs to determine avidity (bivalent binding) and affinity (monovalent binding), respectively.

Example 3: Antibodies Characterization

Biacore Kinetics

Interaction kinetics were determined by using surface plasmon resonance technology on a Biacore T200 instrument. Three different ligands including recombinant full-length human alpha synuclein monomer, purified recombinant human alpha synuclein fibrils, and purified recombinant mouse alpha synuclein fibrils, prepared as described herein, were each immobilized on three different flow cells of a CM5 chip surface using amine-coupling chemistry. The three ligands were prepared in 10 mM NaAc, pH 3.5, and immobilized onto separate flow cell surfaces to reach an immobilization level of about 30 response units (RU) for alpha synuclein monomer, about 40 RU for human alpha synuclein fibrils, and about 300 RU for mouse alpha synuclein fibrils respectively, at a flow rate of 10 µl/min. The buffer HBS-EP+ (GE healthcare Bio-Sciences AB) was used as running buffer for both ligand immobilization and kinetics assay. The binding of monoclonal 6470 rabbit IgG1 (comprising SEQ ID NOs: 47 and 48) and monoclonal 6470 rabbit Fab (Comprising SEQ ID NOs: 47 and 49) to the three ligands was then measured. The monoclonal IgG or Fab antibodies were injected at 7 different concentrations from 800 nM to 0.195 nM over the 3 flow cells with a contact time of 3 mins and a disassociation time of 30 mins, at a flow rate of 100 µl/min. The surface was regenerated by one injection of 50 mM HCl for 90 s at 10 µl/min, and another injection of 50 mM HCl for 60 s at 10 µl/min. The data were analyzed using the Biacore T200 evaluation software (version 3.0) using the bivalent analyte model with assumed no bulk contribution (RI=0) and global Rmax for IgG format, and 1:1 model with flexible bulk contribution (local RI) and global Rmax.

The kinetic values for both IgG and Fab binding to the immobilized targets are shown in Table 2. The IgG format showed apparent selective affinity toward human alpha synuclein fibrils comparing to the affinity to human alpha synuclein monomer, as disassociation constant KD is more than 10 times lower for human fibrils.

inhibitor cocktail (2 tablets, Roche) and 10 mg lysozyme (Sigma)). The lysate was clarified by centrifugation at 18 000 rpm, and the cleared lysate passed through a 0.22 µm filter (Stericup, Millipore). The sterile lysate was loaded onto a MonoQ 10/100GL (GE Healthcare) equilibrated with 20 mM Tris/HCl pH 8.0, 5CV and protein was eluted with a gradient to 500 mM NaCl in the same buffer. Further purification of the purest fractions was repeated on the MonoQ 10/100GL column, following a 5-fold dilution in 20 mM Tris/HCl pH 8.0. The purest fractions were pooled, concentrated with a 10 kDa MWCO centrifugal concentrator (Centriprep, Millipore), purified by size exclusion on a HiLoad 26/600 Superdex 75 column (GE Healthcare), and eluted in 25 mM sodium phosphate buffer, 100 mM NaCl (pH 6.4). Fractions from the Superdex 75 column were pooled and Sodium azide (0.02% final concentration) and AEBSF (10 µM final concentration) were added. The final protein concentration was approximately 5 mg/ml.

Rabbit 6470 Fab (comprising a VL of SEQ ID No.: 11 and a VH of SEQ ID No.: 13, and also comprising SEQ ID NOs: 47 and 49) was expressed in CHO SXE as His tagged entities and purified from the supernatant by His-tag affinity chromatography, binding the protein to HisTrap Excel (GE Healthcare) from supernatant and eluting it with 250 mM imidazole in PBS. The elution pool was loaded onto HiTrap GammaBind Plus Sepharose (GE Healthcare), the column

TABLE 2

| sample | human monomer | | | human fibril | | | mouse fibril | | |
|---|---|---|---|---|---|---|---|---|---|
| | ka1 (1/Ms) | kd 1 (1/s) | KD1 (nM) | ka1 (1/Ms) | kd 1 (1/s) | KD1 (nM) | ka1 (1/Ms) | kd 1 (1/s) | KD1 (nM) |
| 6470 rabbit Fab | 1.80E+06 | 2.67E−02 | 14.79 | 1.83E+06 | 2.25E−02 | 12.35 | 1.38E+06 | 2.43E−02 | 17.65 |
| 6470 rabbit IgG1 | 4.75E+06 | 1.42E−02 | 2.98 | 1.76E+06 | 4.78E−04 | 0.27 | 8.89E+05 | 3.07E−04 | 0.34 |

Binding to Beta Synuclein

Figure 4A:
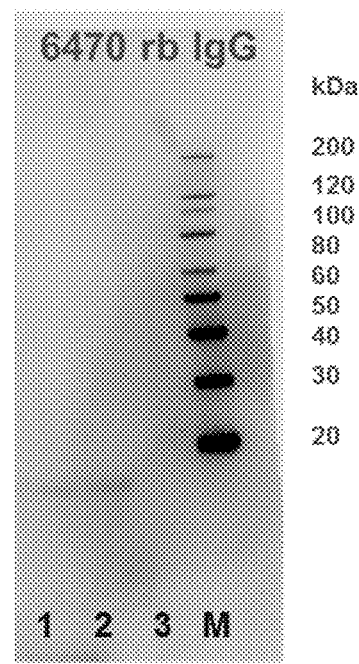
FIGS. 4A and 4B. (A) Western blot showing binding of rabbit 6470 IgG1 to human alpha-synuclein and human beta-synuclein. 1, Human alpha-synuclein; 2, Human alpha-synuclein (rPeptide); 3, Human beta-synuclein (rPeptide); Marker, MagicMark XP. (B) NMR chemical shift changes showing the predicted epitope of 6470 on human alpha synuclein.

The binding of antibodies raised against human alpha synuclein to human beta synuclein were tested by Western blot using rPeptide beta synuclein. One micro gram of synuclein was run on a 4-12% Bis/Tris gel and blotted onto PVDF membrane. The membrane was blocked in PBS with 3% BSA and 0.1% Tween20. 6470 rabbit IgG1 antibody was added to the blocked blot and incubated for 1 hour at room temperature, washed with PBS, 0.1% Tween20 and incubated for 1 hour with a secondary antibody-HRP conjugate (anti rabbit H+L HRP conjugate, Bethyl, A120-101P). The blot was washed extensively in PBS with 0.1% Tween20, PBS and water. Chemi-luminescence was measured after addition of ECL Western blot substrate (Pierce). As shown in FIG. 4(A) lane 3, 6470 rabbit IgG1 does not bind to human beta-synuclein.

Epitope Mapping
NMR

Human alpha-synuclein was cloned into pET28a expression vector, such that the protein was expressed without any tags. The construct was transformed into E. coli BL21(DE3) cells (Stratagene), and cells were grown in defined medium with $C^{13}$ labelled DL-glucose and $N^{15}$ labelled ammonium sulphate in the presence and absence of deuterium oxide ($D_2O$). Expression was induced at OD600 nm=1 with 300 mM IPTG and the culture incubated at 30° C. for 4 hours. Cells were pelleted and lysed by three freeze-thaw cycles in 100 ml lysis buffer (20 mM Tris/HCl pH8.0, 25 units benzonase (Merck Millipore), complete EDTA free protease washed with PBS and protein eluted with 0.1M Glycine-HCl pH 2.6, and pH was adjusted to pH 6 with 0.75M Sodium Phosphate pH 9. The eluted Fab-His protein was buffer exchanged into NMR buffer (25 mM Sodium Phosphate pH 6.4, 100 mM NaCl) on a HiPrep 26/10 desalting column. Fab-His protein fractions were concentrated and protease inhibitors AEBSF (10 pM final concentration) and Sodium azide (0.02% final concentration) were added before filter sterilization over a Millex GV 0.22 µm filter. For crystallography, the concentrated 6470 Fab-His was purified by preparative size exclusion chromatography on a HiLoad 26/600 Superdex 75 (GE Healthcare) column equilibration and eluted with 25 mM Sodium Phosphate pH 6.4, 100 mM NaCl. The purity of the final pools was tested on UPLC-SEC at >99% purity. Final pools were passed through a Millex GV 0.22 mm filter for sterilization.

Backbone Assignment of α-Synuclein

NMR samples were typically 350 µl in volume with a protein concentration of 360 µM 130/15N labelled or 430 µM $^2H/^{13}C/^{15}N$ labelled human a-Synuclein in 5 mm Shigemi tubes. Buffer conditions were 100 mM NaCl, 25 mM Sodium Phosphate pH 6.4, 10 µM AEBSF, 0.02% $NaN_3$. All experiments were recorded at 20° C. on either a 600 MHz Bruker AVIII or a 800 MHz Bruker AVII spectrometer fitted with cryogenically cooled probes. Sequential connections between backbone NMR signals of residues in the protein, $H_N(i)-N(i)-N(i±1)$, were made using a 3D (H)N (CA)NNH experiment (Weisemann et al., 1993 3D Triple-resonance NMR techniques for the sequential assignment of NH and 15N resonances in 15N- and 13C-labelled proteins. J. Biomol. NMR 3) recorded with spectral widths of 28, 28 and 10 ppm and acquisition times of 117 (F1), 117 (F2) and 140 (F3) ms in the $^{15}$N, $^{15}$N and $^1$H dimensions, respectively, with 8 scans per increment and a 1.5 s relaxation delay. Non-uniform sampling was employed with a sampling density of 10% (4000 out of 40000 hyper-complex points) giving a total acquisition time of 2.75 days. Sequential connections were confirmed and residue types identified using TROSY-HNCA (Grzesiek and Bax, 1992 Improved 3D triple-resonance NMR techniques applied to a 31 kDa protein. J. Magn. Reson. 96, 432-440; Salzmann et. al., 1998. TROSY in triple-resonance experiments: new perspectives for sequential NMR assignment of large proteins. Proc. Natl. Acad. Sci. USA. 95, 13585-90) and TROSY-HNCACB (Wittekind and Mueller, 1993 HNCACB, a High-Sensitivity 3D NMR Experiment to Correlate Amide-Proton and Nitrogen Resonances with the Alpha- and Beta-Carbon Resonances in Proteins. J. Magn. Reson. Ser. B 101, 201-205; Salzmann et. al., 1999. TROSY-type Triple Resonance Experiments for Sequential NMR Assignment of Large Proteins. J. Am. Chem. Soc. 121, 844-848) experiments. The TROSY-HNCA experiment was recorded with spectral widths of 23, 28, 10 ppm and acquisition times of 12.1 (F1), 21.7 (F2) and 100 (F3) ms in the $^{13}$C, $^{15}$N and $^1$H dimensions respectively (8 scans per increment, 1.5 s relaxation delay, 1 day total acquisition time) whilst the TROSY-HNCACB was recorded with spectral widths of 56, 28 and 10 ppm and acquisition times of 8.2 (F1), 21.7 (F2) and 100 (F3) ms in the $^{13}$C, $^{15}$N and $^1$H dimensions respectively (8 scans per increment, 1.5 s relaxation delay, 1.7 days total acquisition time). Backbone carbonyl assignments were obtained from a TROSY-HNCO spectrum (Grzesiek and Bax, 1992 Improved 3D triple-resonance NMR techniques applied to a 31 kDa protein. J. Magn. Reson. 96, 432-440; Salzmann et. al., 1998. TROSY in triple-resonance experiments: new perspectives for sequential NMR assignment of large proteins. Proc. Natl. Acad. Sci. USA. 95, 13585-90) recorded with spectral widths of 10, 29, 10 ppm and acquisition times of 80 (F1), 21.7 (F2) and 150 (F3) ms in the $^{13}$C, $^{15}$N and $^1$H dimensions respectively (8 scans per increment and a 1.5 s relaxation delay). Non-uniform sampling was employed with a sampling density of 15% (1208 out of 8050 hyper-complex points) giving a total acquisition time of 19 hours. NMR spectra were processed using NMRPipe (Delaglio et al., 1995 NMRPipe: a multidimensional spectral processing system based on UNIX pipes. J. Biomol. NMR 6, 277-93), with linear prediction used to extend the effective acquisition time in nitrogen by up to 1-fold. The non-uniform sampled data was reconstructed using the Harvard iterative soft thresholding method (Hyberts et al., 2012), with the data reconstructed to the next Fourier number, increasing the indirect acquisition times by up to 60%. Data analysis was carried out using Sparky (Goddard and Kneller, D. G. SPARKY 3. In., University of California, San Francisco), resulting in the assignment of the amide proton and nitrogen resonances of 133 residues, corresponding to 99% of residues (excluding proline residues and the N-terminal methionine).

Mapping of the binding site of the 6470 Fab was carried out using a 150 μM sample of $^2$H/$^{13}$C/$^{15}$N labelled human alpha synuclein containing a 10% molar excess of the unlabelled 6470 Fab. Samples were prepared in the same buffer as described above for the backbone assignment of the alpha synuclein. $^1$H, $^{15}$N and $^{13}$C chemical shift changes were determined by comparison of the TROSY-HNCO (Grzesiek and Bax, 1992 Improved 3D triple-resonance NMR techniques applied to a 31 kDa protein. J. Magn. Reson. 96, 432-440; Salzmann et. al., 1998. TROSY in triple-resonance experiments: new perspectives for sequential NMR assignment of large proteins. Proc. Natl. Acad. Sci. USA. 95, 13585-90) spectrum recorded on the alpha synuclein/Fab complex with an equivalent control spectrum recorded on the free alpha synuclein. The control TROSY-HNCO experiment of the free alpha synuclein was recorded with spectral widths of 10, 28 and 10 ppm and acquisition times of 80 (F1), 22 (F2) and 150 (F3) ms in the $^{13}$C, $^{15}$N, and $^1$H dimensions respectively (16 scans per increment, 1.5 s relaxation delay). Non-uniform sampling was employed with a sampling density of 25% (2013 out of 8050 hyper-complex points) giving a total acquisition time of 2.7 days. The TROSY-HNCO experiment of the alpha synuclein/Fab complex was recorded with spectral widths of 10, 28 and 10 ppm and acquisition times of 80 (F1), 21.7 (F2) and 80 (F3) ms in the $^{13}$C, $^{15}$N, and $^1$H dimensions respectively (32 scans per increment, 1.5 s relaxation delay). Non-uniform sampling was employed with a sampling density of 25% (1119 out of 4477 hyper-complex points) giving a total acquisition time of 2.8 days. NMR spectra were processed using NMRPipe (Delaglio et al., 1995 NMRPipe: a multi-dimensional spectral processing system based on UNIX pipes. J. Biomol. NMR 6, 277-93) with reconstruction of the NUS data performed using mddnmr. Analysis of non-uniformly sampled spectra with Multi-Dimensional Decomposition. Prog. Nucl. Magn. Reson. Spectrosc., 59, p 271-292). The effective acquisition time of the nitrogen dimension was increased by up to 1-fold during the data reconstruction.

Chemical shift changes were analysed using the minimal shift approach (Williamson et al., 1997 Mapping the binding site for matrix metalloproteinase on the N-terminal domain of the tissue inhibitor of metalloproteinases-2 by NMR chemical shift perturbation. Biochemistry 36, 13882-9), essentially as described previously (Veverka et al., 2008 Structural characterization of the interaction of mTOR with phosphatidic acid and a novel class of inhibitor: compelling evidence for a central role of the FRB domain in small molecule-mediated regulation of mTOR. Oncogene 27, 585-95), with the exception of a modification to the equation used to calculate the combined chemical shift change (Δδ) to include the carbonyl chemical shift, resulting in the following equation:

$$\Delta\delta = \frac{\sqrt{(\Delta\delta HN)^2 + (\Delta\delta N\alpha N)^2 + (\Delta\delta C\alpha C)^2}}{3}$$

where $\Delta\delta_{HN}$, $\Delta\delta_N$ and $\Delta\delta_C$ are the differences in the $^1$H, $^{15}$N and $^{13}$C chemical shifts respectively. αN and αC correspond to scaling factors of 0.2 and 0.35, respectively, used to account for differences in the chemical shift ranges of the amide proton, nitrogen and carbonyl chemical shifts.

To identify the Fab binding sites (epitopes) on alpha synuclein, a histogram of combined minimal shift versus protein sequence was used to reveal regions of alpha synuclein containing significantly perturbed signals. If the size of the combined chemical shift change for individual amino acids exceeded a threshold value of the mean of the combined chemical shift change for all the amino acids plus one standard deviation from that mean, these residues were selected for further evaluation as possible contact residues in the Fab binding site.

Significantly perturbed residues were identified as those whose minimal shift was at least greater than the mean plus one standard deviation of all calculated shifts. Four different thresholds were applied to identify residues bound by the Fab. Residues that are involved in the binding site are scored with increasing stringency as: those whose minimal shift exceeds mean plus one standard deviations of all calculated shifts (being >0.018925); those whose minimal shift exceeds mean plus two standard deviations of all calculated shifts (being >0.032049); those whose minimal shift exceeds mean plus three standard deviations of all calculated shifts (being >0.045174); those whose minimal shift exceeds mean plus four standard deviations of all calculated shifts (being >0.058299). In this analysis proline residues cannot be identified as they contain no amide proton.

The epitope for 6470 Fab is therefore defined with increasing stringency as mean plus one standard deviation of all calculated shifts: D121, N122, E123, A124, Y125, E126, M127, S129, E130, Y133, Q134, D135 and Y136; mean plus two standard deviation of all calculated shifts: E123, A124, Y125, E126, M127, S129, E130, D135 and Y136; mean plus three standard deviation of all calculated shifts: Y125, M127, S129, and D135; mean plus four standard deviation of all calculated shifts: M127, S129, and D135.

Figure 4B:
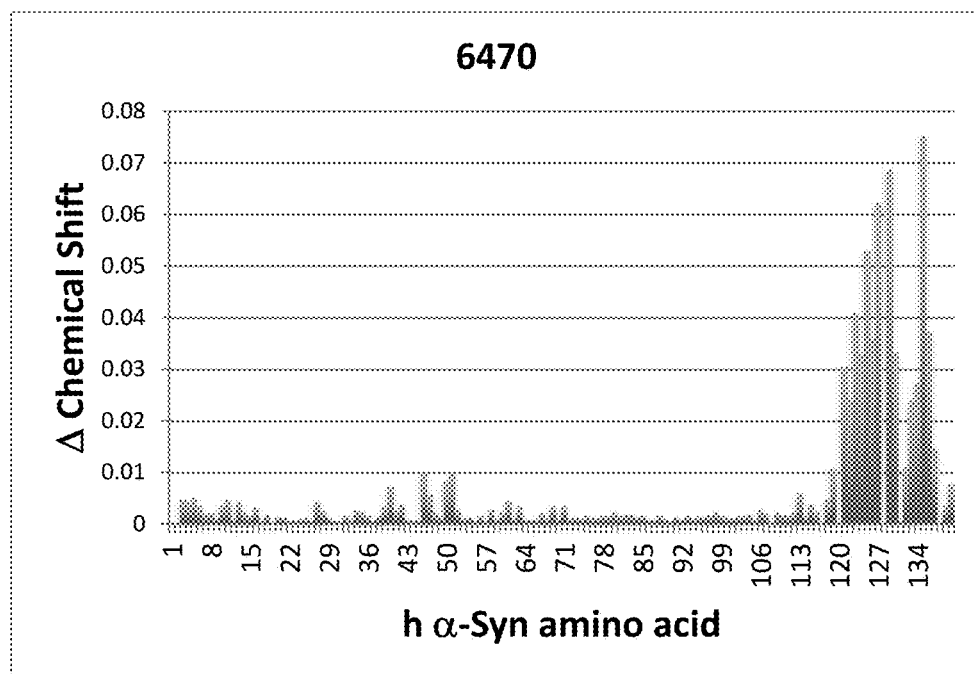

As shown in FIG. 4B, antibody 6470 was found to bind by NMR studies at least the following residues (mean+3 SD) Y125, M127, S129, and D135 and in addition to also bind all the following residues (mean+1 SD) D121, N122, E123, A124, E126, E130, Y133, Q134 and Y136 of human alpha-synuclein (SEQ ID NO: 10).

Peptide Mapping

Further characterization of the epitope bound by 6470 was performed by using short (typically 9-mer or 10-mer) peptides representative of and covering the C-terminal region of human alpha synuclein. These were used in a competitive surface plasmon resonance assay to test whether any were capable of inhibiting binding of the antibody to either monomeric alpha synuclein or pre-formed alpha synuclein fibrils immobilised on a Biacore chip. A peptide showing the maximum level of inhibition was then selected for co-crystallization studies with the antibody in order to confirm the exact epitope.

Peptides were supplied by Peptide Protein Research Ltd., Bishop's Waltham, U.K., and were synthesized by Fmoc solid phase peptide chemistry according to the method of Atherton and Sheppard. (Ref: Atherton, E.; Sheppard, R. C. (1989). Solid Phase peptide synthesis: a practical approach. Oxford, England: IRL Press). N and C peptide termini were capped with acetyl and amide groups respectively except in the case of the peptides representing the N-terminus and C-terminus of a-synuclein where the amino and carboxyl groups respectively remained free. Peptide stock solutions were prepared in DMSO at 10 mM. The full list of peptides is shown in Table 3.

TABLE 3

| Peptide ID | Sequence |
|---|---|
| AS104-113 | EEGAPQEGIL |
| AS109-118 | QEGILEDMPV |
| AS111-120 | GILEDMPVDP |
| AS113-122 | LEDMPVDPDN |
| AS115-124 | DMPVDPDNEA |
| AS117-126 | PVDPDNEAYE |

TABLE 3 -continued

| Peptide ID | Sequence |
|---|---|
| AS119-128 | DPDNEAYEMP |
| AS121-130 | DNEAYEMPSE |
| AS123-132 | EAYEMPSEEG |
| AS125-134 | YEMPSEEGYQ |
| AS127-136 | MPSEEGYQDY |

Recombinant human alpha synuclein monomer and pre-formed alpha synuclein fibrils were immobilized on a CM5 chip using a Biacore 3000 instrument (GE Healthcare). Following activation of the carboxymethyl dextran surface by injection of 100 μl of a fresh 1:1 (v/v) mixture of 50 mM N-hydroxysuccimide and 200 mM 1-ethyl-3-(3-dimethyl-aminopropyl)-carbodiimide at a flow rate of 10 μl/min HBS-EP (GE Healthcare) as running buffer, coupling was achieved by injecting 100 μl of monomer and fibrils, at 5 μM in 10 mM acetate pH 5.0, over separate flow cells. A reference flow cell was activated in the same manner and then all flow cell surfaces were deactivated with a 50 μl pulse of 1 M ethanolamine HCl pH 8.5.

Peptide solutions were prepared in running buffer at 100 μM and a peptide blank control prepared as a 1 in 100 dilution of DMSO in running buffer. A solution of 6470 rabbit Fab (comprising SEQ ID NO: 47 and 49) was prepared at 50.5 nM in running buffer prior to pre-incubating 198 μl with 2 μl of either blank control or diluted peptide to yield a final mixture of 50 nM Fab and 1 pM peptide or control. Sensorgrams were recorded for each sample by injecting 30 μl of the mixture at 10 μl/min and recording a report point 5 seconds before the end of the injection. The chip was regenerated at the end of each cycle by two 10 μl injections of 40 mM HCl and one injection of 5 mM NaOH. Control cycles were alternated with peptide cycles.

The degree of inhibition of each peptide were calculated as the percentage change in response units measured at the report point compared to that of the mean of adjacent control cycles.

Figure 5:
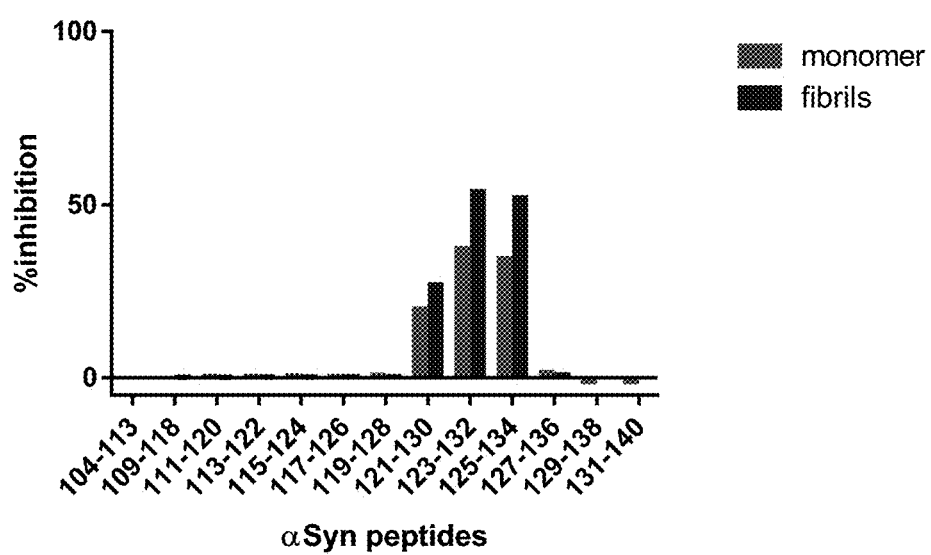
FIG. 5. Inhibition of binding of 6470 IgG to immobilized alpha synuclein (bars at the left, monomer and right fibrils, respectively, for each of the peptides tested).

The level of inhibition of each alpha synuclein peptide is shown in FIG. 5. Significant inhibition of 6470 Fab to either alpha synuclein monomer or fibrils was only observed for the three peptides: AS121-130, AS123-132 and AS125-134, where the highest levels of inhibition were observed for AS123-132 at 37% and 54% for binding of the antibody to monomer and fibrils respectively. Slightly lower levels of inhibition were obtained for peptide AS125-134 at 34% and 52% respectively indicating that the major component of the epitope comprised residues 125 to 132. Peptide AS121-130 inhibited at lower levels of 20% and 27% respectively suggesting that the residues in common to all three peptides: 125 to 130 contributed most to the epitope.

As the epitope of the 6470 antibody appeared to comprise at least the sequence YEMPSEEG, the AS123-132 peptide was investigated in co-crystallization studies with the 6470 Fab.

X-Ray Crystallography

To prepare the complexes, 1 ml of purified 6470 rabbit Fab, at approximately 10 mg/ml was mixed with alpha-synuclein peptide 123-132 (EAYEMPSEEG) in a Fab:peptide molar ratio of 1:2 and incubated for 1 hour at room temperature. Conditions suitable for crystal growth were identified by the sitting drop vapor diffusion method using commercially available crystallization screens (Qiagen). To generate diffraction quality crystals, hanging drop vapor diffusion method was used.

For the 6470 Fab-peptide 123-132 complex, 1 µl of protein solution was mixed with 1 µl of reservoir solution containing 1.6 M ammonium sulphate and 0.1 M Hepes buffer pH 7.5. Crystals were harvested and flash frozen in liquid nitrogen after briefly passing through a cryoprotectant solution containing 1.6 M ammonium sulphate, 0.1 M Hepes buffer pH 7.5 and 20% glycerol. Crystals were harvested and flash frozen in liquid nitrogen after briefly passing through a cryoprotectant solution containing 0.2 M ammonium sulphate, and 35% (v/v) polyethylene glycol 8000.

Diffraction data to 2.9 Å was collected from single crystals of 6470 Fab-peptide 123-132 on beamline i04-1 at the Diamond Synchrotron, Didcot, Oxfordshire, UK, and processed using Mosflm, Aimless and Truncate. The structure of the complex was solved by molecular replacement with Phaser using the coordinates of an in-house Fab as a search model.

Cycles of refinement and model building were performed using CNS (Brunger et al., (2007) Nature Protocols 2, 2728-2733) and COOT (Emsley et al., (2004) Acta crystallographica. Section D, Biological crystallography 60, 2126-2132) until all the refinement statistics converged for both models. Model geometry was validated using Molprobity43. Molecular visualizations were generated with Pymol44. Epitope information described below was derived by considering atoms within 4 Å distance at the Fab/peptide contact surface. The data collection and refinement statistics are shown in Table 4A and Table 4B.

TABLE 4A

| Structure | VR6470 Fab-peptide 123-132 |
| --- | --- |
| Space group | P 3$_1$ 2 1 |
| Cell dimensions | |
| a, b, c (Å) | 111.78, 111.78, 71.93 |
| α, β, γ (°) | 90.00, 90.00, 120.00 |
| Resolution (Å) | 30.00-2.90 (3.08-2.90) |
| R$_{merge}$ | 0.07 (0.36) |
| I/σI | 17.0 (5.1) |
| Completeness (%) | 99.9 (100) |
| Redundancy | 9.8 (10.2) |

TABLE 4B

| Refinement | VR6470 Fab-peptide 123-132 |
| --- | --- |
| Resolution (Å) | 30.00-2.90 |
| No. reflections | 11762 |
| R$_{work}$/R$_{free}$ | 0.2587/0.3192 |
| No. atoms | |
| Protein | 3259 |
| Water | 0 |
| Ligand | 30 |
| B-factors | |
| Peptide | 81.8 |
| Fab | 67.4 |
| R.m.s. deviations | |
| Bond lengths (Å) | 0.005 |
| Bond angles (°) | 1.125 |

Values in parenthesis refer to the high-resolution shell. Rsym=Σ|(I−<I>)|/Σ(I), where I is the observed integrated intensity, <I> is the average integrated intensity obtained from multiple measurements, and the summation is over all observed reflections. Rwork=Σ||Fobs|−k|Fcalc||/Σ|Fobs|, where Fobs and Fcalc are the observed and calculated structure factors, respectively. Rfree is calculated as Rwork using 5% of the reflection data chosen randomly and omitted from the refinement calculations.

The main contact between the heavy and light chain residues and the peptide are shown in Table 5.

TABLE 5

| Chain | residue (SEQ ID NO: 13) | Atom | Chain | Peptide Amino Acid | Peptide Target Atom | Distance (Å) |
| --- | --- | --- | --- | --- | --- | --- |
| H | 96 (HIS) | NE2 [N] | A | 125 (TYR) | CD1 [C] | 3.93 |
| H | 96 (HIS) | CD2 [C] | A | 125 (TYR) | CD1 [C] | 3.93 |
| | | | A | 125 (TYR) | CE1 [C] | 3.69 |
| H | 99 (ASN) | CB [C] | A | 125 (TYR) | CD2 [C] | 3.34 |
| H | 99 (ASN) | N [N] | A | 125 (TYR) | CD2 [C] | 3.57 |
| H | 99 (ASN) | CB [C] | A | 125 (TYR) | CE2 [C] | 3.85 |
| H | 96 (HIS) | CA [C] | A | 125 (TYR) | CE2 [C] | 3.85 |
| H | 96 (HIS) | CB [C] | A | 125 (TYR) | CE2 [C] | 3.93 |
| H | 97 (TYR) | N [N] | A | 125 (TYR) | CE2 [C] | 3.81 |
| H | 99 (ASN) | CA [C] | A | 125 (TYR) | CE2 [C] | 3.99 |
| H | 98 (GLY) | N [N] | A | 125 (TYR) | CE2 [C] | 3.42 |
| H | 98 (GLY) | CA [C] | A | 125 (TYR) | CE2 [C] | 3.91 |
| H | 98 (GLY) | C [C] | A | 125 (TYR) | CE2 [C] | 4 |
| H | 99 (ASN) | N [N] | A | 125 (TYR) | CE2 [C] | 3.12 |
| H | 96 (HIS) | CA [C] | A | 125 (TYR) | CZ [C] | 3.5 |
| H | 96 (HIS) | CB [C] | A | 125 (TYR) | CZ [C] | 3.96 |
| H | 96 (HIS) | C [C] | A | 125 (TYR) | CZ [C] | 3.79 |
| H | 97 (TYR) | N [N] | A | 125 (TYR) | CZ [C] | 3.32 |
| H | 98 (GLY) | N [N] | A | 125 (TYR) | CZ [C] | 3.72 |
| H | 96 (HIS) | CA [C] | A | 125 (TYR) | OH [O] | 3.19 |
| H | 97 (TYR) | N [N] | A | 125 (TYR) | OH [O] | 2.32 |
| H | 97 (TYR) | C [C] | A | 125 (TYR) | OH [O] | 3.64 |
| H | 98 (GLY) | N [N] | A | 125 (TYR) | OH [O] | 3.1 |
| H | 97 (TYR) | CG [C] | A | 125 (TYR) | OH [O] | 3.51 |
| H | 97 (TYR) | CE1 [C] | A | 125 (TYR) | OH [O] | 3.86 |
| H | 97 (TYR) | CA [C] | A | 125 (TYR) | OH [O] | 3.19 |
| H | 97 (TYR) | CB [C] | A | 125 (TYR) | OH [O] | 3.38 |
| H | 97 (TYR) | CD1 [C] | A | 125 (TYR) | OH [O] | 2.84 |
| H | 32 (ASP) | OD1 [O] | A | 126 (GLU) | CA [C] | 3.34 |
| | | | A | 126 (GLU) | CB [C] | 3.78 |
| H | 52 (ALA) | CB [C] | A | 126 (GLU) | CG [C] | 3.92 |
| H | 32 (ASP) | OD1 [O] | A | 126 (GLU) | CG [C] | 3.16 |
| | | | A | 126 (GLU) | CD [C] | 3.47 |
| H | 52 (ALA) | N [N] | A | 126 (GLU) | OE2 [O] | 3.82 |
| H | 52 (ALA) | CB [C] | A | 126 (GLU) | OE2 [O] | 3.92 |
| H | 32 (ASP) | OD1 [O] | A | 126 (GLU) | OE2 [O] | 2.99 |
| H | 51 (TYR) | CB [C] | A | 126 (GLU) | OE2 [O] | 3.93 |
| H | 32 (ASP) | CG [C] | A | 126 (GLU) | OE2 [O] | 3.89 |
| H | 51 (TYR) | CD2 C] | A | 126 (GLU) | OE2 [O] | 3.7 |
| H | 32 (ASP) | OD1 [O] | A | 126 (GLU) | C [C] | 3.2 |
| H | 32 (ASP) | CG [C] | A | 126 (GLU) | C [C] | 3.72 |
| H | 32 (ASP) | OD2 [O] | A | 126 (GLU) | C [C] | 3.79 |
| H | 32 (ASP) | OD1 [O] | A | 126 (GLU) | O [O] | 2.4 |
| H | 32 (ASP) | CG [C] | A | 126 (GLU) | O [O] | 2.8 |
| H | 32 (ASP) | OD2 [O] | A | 126 (GLU) | O [O] | 2.73 |
| H | 51 (TYR) | CD2 [C] | A | 126 (GLU) | O [O] | 3.87 |
| H | 51 (TYR) | CE2 [C] | A | 126 (GLU) | O [O] | 3.96 |
| | | | A | 127 (MET) | CB [C] | 3.99 |
| | | | A | 127 (MET) | C [C] | 3.85 |
| H | 51 (TYR) | CD2 [C] | A | 127 (MET) | O [O] | 3.1 |
| H | 51 (TYR) | CE2 [C] | A | 127 (MET) | O [O] | 3.03 |
| H | 57 (TYR) | OH [O] | A | 129 (SER) | CB [C] | 3.05 |
| H | 57 (TYR) | CZ [C] | A | 129 (SER) | CB [C] | 3.96 |
| H | 57 (TYR) | OH [O] | A | 129 (SER) | OG [O] | 2.78 |
| H | 57 (TYR) | CE2 [C] | A | 129 (SER) | OG [O] | 3.79 |
| H | 57 (TYR) | CZ [C] | A | 129 (SER) | OG [O] | 3.7 |
| Chain | residue (SEQ ID NO: 11) | Atom | Chain | Peptide Amino Acid | Peptide Target Atom | Distance (angstroms) |
| L | 34 (TYR) | OH [O] | A | 123 (GLU) | CD [C] | 3.63 |
| | | | A | 123 (GLU) | OE1 [O] | 3.46 |

TABLE 5-continued

| | | | | | | |
|---|---|---|---|---|---|---|
| L | 34 (TYR) | CE1 [C] | A | 123 (GLU) | OE2 [O] | 3.68 |
| L | 34 (TYR) | CZ [C] | A | 123 (GLU) | OE2 [O] | 3.74 |
| L | 34 (TYR) | OH [O] | A | 123 (GLU) | OE2 [O] | 3.01 |
| | | | A | 125 (TYR) | CE2 [C] | 3.89 |
| L | 34 (TYR) | CE2 [C] | A | 125 (TYR) | CE2 [C] | 3.85 |
| | | | A | 125 (TYR) | CZ [C] | 3.59 |
| L | 34 (TYR) | CD2 [C] | A | 125 (TYR) | OH [O] | 3.66 |
| L | 34 (TYR) | CE2 [C] | A | 125 (TYR) | OH [O] | 3.39 |
| L | 93 (TYR) | CE2 [C] | A | 127 (MET) | CB [C] | 3.75 |
| L | 93 (TYR) | CZ [C] | A | 127 (MET) | CB [C] | 3.62 |
| L | 93 (TYR) | OH [O] | A | 127 (MET) | CB [C] | 3.05 |
| L | 93 (TYR) | CE2 [C] | A | 127 (MET) | CG [C] | 3.4 |
| L | 93 (TYR) | CZ [C] | A | 127 (MET) | CG [C] | 3.69 |
| L | 93 (TYR) | OH [O] | A | 127 (MET) | CG [C] | 3.67 |
| L | 34 (TYR) | CE2 [C] | A | 127 (MET) | CG [C] | 3.95 |
| L | 34 (TYR) | CZ [C] | A | 127 (MET) | SD [S] | 3.49 |
| L | 34 (TYR) | OH [O] | A | 127 (MET) | SD [S] | 3.16 |
| L | 34 (TYR) | CE2 [C] | A | 127 (MET) | SD [S] | 3.05 |
| L | 34 (TYR) | CZ [C] | A | 127 (MET) | CE [C] | 3.72 |
| L | 34 (TYR) | OH [O] | A | 127 (MET) | CE [C] | 3.75 |
| L | 93 (TYR) | CE2 [C] | A | 127 (MET) | CE [C] | 3.22 |
| L | 30 (TYR) | CG [C] | A | 127 (MET) | CE [C] | 3.79 |
| L | 30 (TYR) | CD2 [C] | A | 127 (MET) | CE [C] | 3.35 |
| L | 30 (TYR) | CE2 [C] | A | 127 (MET) | CE [C] | 3.33 |
| L | 34 (TYR) | CE2 [C] | A | 127 (MET) | CE [C] | 3.33 |
| L | 30 (TYR) | CZ [C] | A | 127 (MET) | CE [C] | 3.75 |
| L | 30 (TYR) | OH [O] | A | 128 (PRO) | CD [C] | 3.86 |
| | | | A | 128 (PRO) | CG [C] | 3.43 |
| L | 30 (TYR) | CZ [C] | A | 128 (PRO) | CG [C] | 3.98 |
| L | 93 (TYR) | OH [O] | A | 128 (PRO) | O [O] | 3.45 |
| L | 96 (GLY) | N [N] | A | 128 (PRO) | O [O] | 3.41 |
| L | 96 (GLY) | CA [C] | A | 129 (SER) | CA [C] | 3.88 |
| L | 96 (GLY) | O [O] | A | 129 (SER) | CA [C] | 3.4 |
| L | 96 (GLY) | N [N] | A | 129 (SER) | CA [C] | 3.99 |
| L | 96 (GLY) | O [O] | A | 129 (SER) | CB [C] | 3.56 |
| | | | A | 129 (SER) | C [C] | 3.52 |
| L | 96 (GLY) | CA [C] | A | 130 (GLU) | N [N] | 3.99 |
| L | 96 (GLY) | C [C] | A | 130 (GLU) | N [N] | 3.6 |
| L | 96 (GLY) | O [O] | A | 130 (GLU) | N [N] | 2.73 |
| L | 96 (GLY) | N [N] | A | 130 (GLU) | N [N] | 3.78 |
| L | 96 (GLY) | O [O] | A | 130 (GLU) | CA [C] | 3.71 |
| | | | A | 130 (GLU) | CB [C] | 3.81 |
| L | 97 (ARG) | CD [C] | A | 130 (GLU) | CB [C] | 3.78 |
| | | | A | 130 (GLU) | CG [C] | 3.93 |
| | | | A | 130 (GLU) | CD [C] | 3.72 |
| | | | A | 130 (GLU) | OE1 [O] | 3.85 |
| L | 94 (LYS) | CG [C] | A | 130 (GLU) | OE1 [O] | 3.77 |
| L | 97 (ARG) | CD [C] | A | 130 (GLU) | OE1 [O] | 2.77 |
| L | 97 (ARG) | NE [N] | A | 130 (GLU) | OE1 [O] | 3.75 |
| L | 94 (LYS) | CG [C] | A | 130 (GLU) | OE2 [O] | 3.69 |
| L | 94 (LYS) | O [O] | A | 130 (GLU) | OE2 [O] | 3.63 |
| L | 94 (LYS) | CD [C] | A | 130 (GLU) | OE2 [O] | 3.77 |
| L | 94 (LYS) | CE [C] | A | 130 (GLU) | OE2 [O] | 3.26 |
| L | 97 (ARG) | NE [N] | A | 131 (GLU) | C [C] | 3.94 |
| L | 97 (ARG) | CD [C] | A | 131 (GLU) | O [O] | 3.75 |
| L | 97 (ARG) | NE [N] | A | 131 (GLU) | O [O] | 2.94 |
| L | 97 (ARG) | CZ [C] | A | 131 (GLU) | O [O] | 3.79 |
| L | 97 (ARG) | NH2 [N] | A | 131 (GLU) | O [O] | 2.79 |

Figure 6:
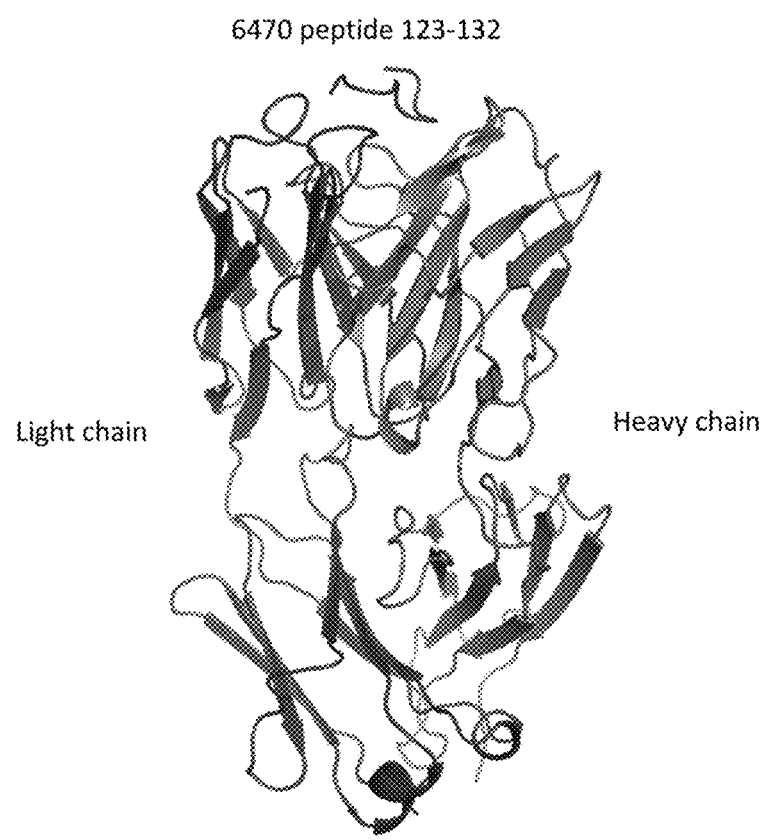
FIG. 6. Schematic representation of the 6470 Fab in complex with peptide 123-132.
Figure 7:
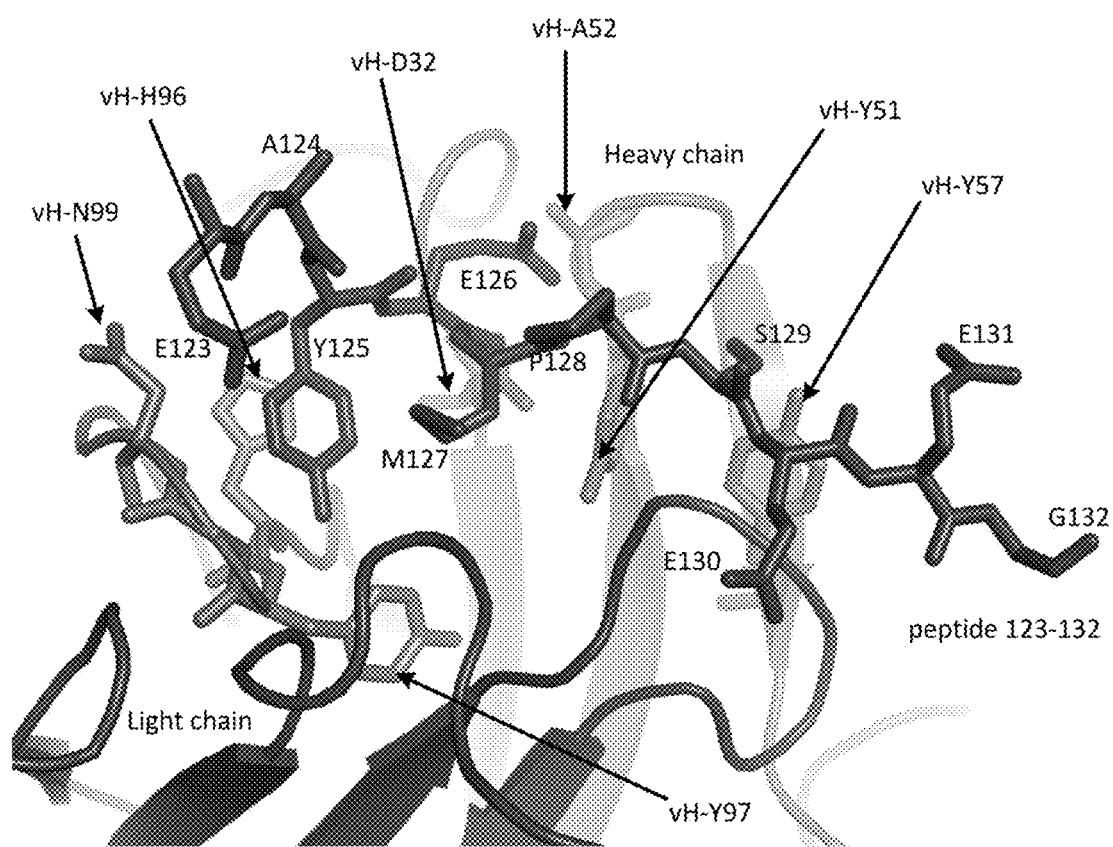
FIG. 7. Schematic representation of 6470 Fab heavy chain contacts with peptide 123-132. The peptide residues are labelled directly, 6470 variable heavy chain residues are labelled vH-residue number.
Figure 8:
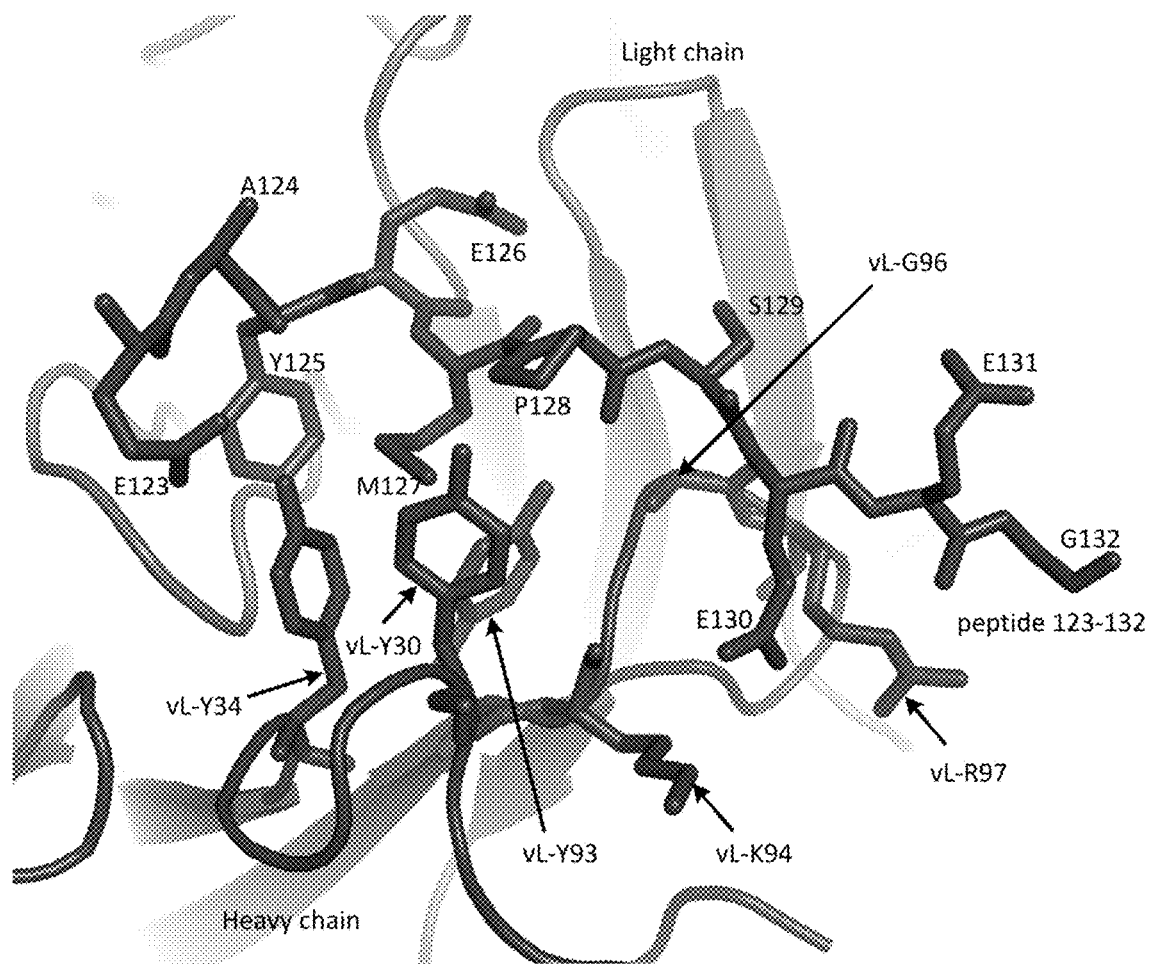
FIG. 8. Schematic representation of 6470 Fab light chain contacts with peptide 123-132. The peptide residues are labelled directly, 6470 variable light chain residues are labelled vL-residue number.

In summary, the epitope comprises residues E123, Y125, E126, M127, P128, S129, E130 and E131. FIG. 6 shows the 6470 Fab in complex with peptide 123-132 and FIGS. 7 and 8 show the contacts between peptide 123-132 and 6470 Fab heavy chain and light chain, respectively.

Example 4: Antibody Humanization and Affinity Maturation

Figure 9:
FIG. 9. Light Chain Humanization. 6470 is for the rabbit variable light chain sequence. 6470gL3 is for the humanized graft of 6470 variable light chain using IGKV1-16 human germline as the acceptor framework. CDRs are shown in bold/underlined. Donor residues are shown in bold/italic and are shaded: Q48 and Q72. The mutation in CDRL1 N33R is shown in bold/underlined and is shaded.
Figure 10:
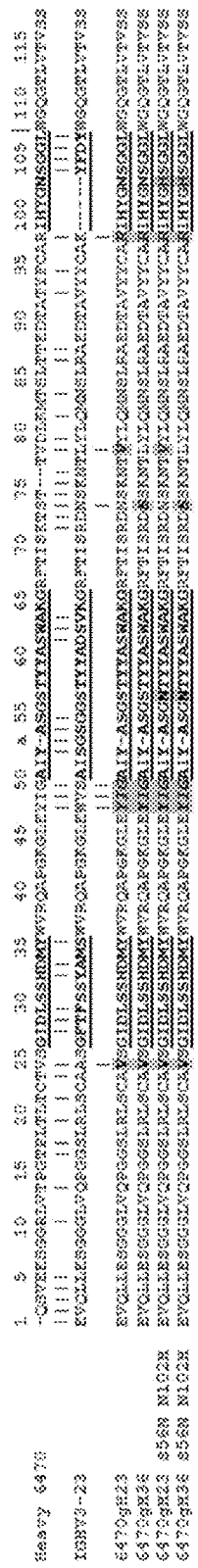
FIG. 10. Heavy Chain Humanization. 6470 is for rabbit variable heavy chain sequence. 6470gH23 and gH36 are for humanized grafts of Antibody 6470 variable heavy chain using IGHV3-23 human germline as the acceptor framework. CDRs are shown in bold/underlined. Donor residues are shown in bold/italic and are shaded: V24, Y47, I48, G49, S73, V78 and R97. The mutations S56N and N102H in CDRH2 and CDRH3, respectively, are shown in bold/underlined and are shaded.

Rabbit antibody 6470 was humanized by grafting the CDRs from the rabbit V-regions onto human germline antibody V-region frameworks. In order to recover the activity of the antibody, a number of framework residues from the rabbit V-regions were also retained in the humanized sequence. These residues were selected using the protocol outlined by Adair et al. (1991) (WO91/09967). Alignments of the rabbit antibody (donor) V-region sequences with the human germline (acceptor) V-region sequences are shown in FIGS. 9 and 10, together with the designed humanized sequences. The CDRs grafted from the donor to the acceptor sequence are as defined by Kabat (Kabat et al., 1987), with the exception of CDR-H1 where the combined Chothia/Kabat definition is used (see Adair et al., WO91/09967).

Genes encoding a number of variant heavy and light chain V-region sequences were designed and constructed by an automated synthesis approach by DNA2.0 Inc. Further variants of heavy and light chain V-regions were created by modifying the VH and VK genes by oligonucleotide-directed mutagenesis, including, in some cases, mutations within CDRs. For transient expression in mammalian cells, the humanized light chain V-region genes were cloned into the UCB light chain expression vector pMhCK, which contains DNA encoding the human Kappa chain constant region (Km3 allotype). The humanized heavy chain V-region genes were cloned into the UCB human gamma-4 heavy chain expression vector pMhγ4PFL, which contains DNA encoding the human gamma-4 heavy chain constant region with the hinge stabilizing mutation S241P (Angal et al., Mol. Immunol. 1993, 30 (1):105-8). Chimeric 6470, comprising the rabbit V-regions (SEQ ID NOs: 11 and 13) and human constant regions was also similarly prepared and used as a comparator antibody. Co-transfection of the resulting heavy and light chain vectors into Expi293™ suspension cells gave expression of the humanized, recombinant antibodies in the human IgG4P. Human V-region IGKV1-16 plus JK4 J-region (IMGT, http://www.imgt.org/) was chosen as the acceptor for antibody 6470 light chain CDRs. The light chain framework residues in graft gL3 are all from the human germline gene, with the exception of residues 48 and 72 (with reference to SEQ ID NO:15), where the donor residues Glutamine (Q48) and Glutamine (Q72) were retained, respectively. Retention of residues Q48 and Q72 was essential for full potency of the humanized antibody (FIG. 9 and Table 6) for binding human alpha synuclein fibrils.

TABLE 6

| Antibodies variants | Light Chain Donor Residues | Heavy Chain Donor Residues | Human fibrils Affinity (KD) pM |
|---|---|---|---|
| Chimeric 6470 | — | — | 99 |
| 6470gL3gH23 | Q48, Q72 | V24, Y47, I48, G49, V78, R97 | 148 |
| 6470gL3gH36 | Q48, Q72 | V24, Y47, I48, G49, S73, R97 | 166 |
| 6470gL6gH23 | Q72 | V24, Y47, I48, G49, V78, R97 | 547 |
| 6470gL6gH36 | Q72 | V24, Y47, I48, G49, S73, R97 | 377 |
| 6470gL8gH23 | Q48 | V24, Y47, I48, G49, V78, R97 | 246 |
| 6470gL8gH36 | Q48 | V24, Y47, I48, G49, S73, R97 | 198 |
| 6470gL3gH25 | Q48, Q72 | V24, I48, G49, K71, S73, V78, R97 | 76000 |

TABLE 6-continued

| Antibodies variants | Light Chain Donor Residues | Heavy Chain Donor Residues | Human fibrils Affinity (KD) pM |
|---|---|---|---|
| 6470gL3gH26 | Q48, Q72 | V24, Y47, G49, K71, S73, V78, R97 | 300 |
| 6470gL3gH27 | Q48, Q72 | V24, Y47, I48, K71, S73, V78, R97 | 22300 |
| 6470gL3gH35 | Q48, Q72 | V24, Y47, I48, G49, K71, S73, V78 | 5282 |
| 6470gL3gH46 | Q48, Q72 | Y47, I48, G49, V78, R97 | 316 |
| 6470gL3gH50 | Q48, Q72 | Y47, I48, G49, S73, R97 | 580 |

Human V-region IGHV3-23 plus JH4 J-region (IMGT, http://www.imgt.org/) was chosen as the acceptor for the heavy chain CDRs of antibody 6470. In common with many rabbit antibodies, the VH gene of antibody 6470 is shorter than the selected human acceptor. When aligned with the human acceptor sequence, framework 1 of the VH region of antibody 6470 lacks the N-terminal residue, which is retained in the humanized antibody (FIG. 10). Framework 3 of the 6470 rabbit VH region also lacks two residues (75 and 76) in the loop between beta sheet strands D and E: in the humanized grafts the gap is filled with the corresponding residues (Lysine 75, K75; Asparagine 76, N76) from the selected human acceptor sequence (FIG. 10). The heavy chain framework residues in grafts gH23 and gH36 are all from the human germline gene, with the exception of one or more residues from the group comprising residues 24, 47, 48, 49, 73, 78 and 97 (with reference to SEQ ID NO: 23 and 31), where the donor residues Valine (V24), Tyrosine (Y47), Isoleucine (I48), Glycine (G49), Serine (S73), Valine (V78) and Arginine (R97) were retained, respectively. Retention of residues V24, Y47, I48, G49 and R97 was essential for full potency of the humanized antibody for binding human alpha synuclein fibrils.

In addition, the humanized VH genes were cloned into the UCB human Fab-HIS expression vector pMhFab10HIS, which contains DNA encoding the human gamma-1 CH1-hinge domain with a C-terminal tag of ten Histidine residues: The Histidine tag facilitates purification of the expressed Fabs by affinity chromatography. Co-transfection of the resulting heavy and light chain vectors into Expi293TM suspension cells gave expression of the humanized, recombinant antibodies in Fab-HIS formats.

Affinity maturation was carried out according to IOTA methods described in WO2014198951. The interface between 6470 rabbit Fab and the alpha synuclein peptide EAYEMPSEEG (123-132) in the complex determined by X-ray crystallography was subjected to analysis to identify mutations that could potentially improve the affinity of 6470 rabbit Fab for alpha synuclein protein. IOTA is a statistical potential tool for determining the probability of a given contact atom type at a protein interface or binding site.

In order to evaluate the effect of these mutations on the potency of the antibodies for binding human alpha synuclein monomer or fibrils, the mutations were firstly studied in the 6470 rabbit Fab (Table 7A). Interaction kinetics were determined by using surface plasmon resonance technology on Biacore T200 instrument as described in Example 3. Residue 33 in CDRL1 (with reference to SEQ ID NO: 11) was mutated from an asparagine (N) to an arginine (R) or lysine (K): mutation of residue 33 to arginine resulted in an increased affinity for alpha synuclein (Table 7A). Residue 55 in CDRH2 was mutated from a serine (S) to an asparagine (N), and residue 99 in CDRH3 was mutated from an asparagine (N) to a lysine (K), or a glutamine (Q) or a histidine (H) or a tryptophan (W) (with reference to SEQ ID NO: 13), mutation of residue 55 to asparagine and residue 99 to histidine resulted in an increased affinity for alpha synuclein (Table 7A). The mutation of the asparagine in CDRH3 (N99H) also removes a potential deamidation site.

TABLE 7A

| | | Monomer | | | Fibril | | |
|---|---|---|---|---|---|---|---|
| Mutation | Chain | ka1 (1/Ms) | kd1 (1/s) | KD1 (nM) | ka1 (1/Ms) | kd1 (1/s) | KD1 (nM) |
| 6470 rabbit Fab | — | 7.23E+06 | 1.24E−01 | 17.2 | 4.58E+06 | 4.76E−02 | 10.3 |
| Y30W | L | 2.99E+06 | 1.51E−01 | 50.4 | 4.75E+06 | 8.95E−02 | 18.8 |
| N33R | L | 1.92E+07 | 7.99E−02 | 7.9 | 9.98E+06 | 2.89E−02 | 2.9 |
| N33K | L | 2.84E+06 | 4.33E−02 | 15.2 | 6.93E+06 | 4.98E−02 | 7.1 |
| H31R | H | 2.65E+05 | 4.40E−01 | 1658.4 | 5.98E+06 | 3.73E−01 | 62.3 |
| H31K | H | 6.17E+06 | 9.38E−01 | 151.9 | 9.06E+06 | 4.23E−01 | 46.7 |
| H31Q | H | 8.00E+06 | 1.85E−01 | 23.1 | 7.83E+06 | 9.72E−02 | 12.4 |
| S53N | H | 4.56E+04 | 5.17E−02 | 1132.6 | 5.75E+06 | 2.86E−01 | 49.6 |
| S55N | H | 1.39E+07 | 1.91E−02 | 1.9 | 9.20E+06 | 1.30E−02 | 1.4 |
| N99R | H | 1.22E+07 | 1.70E−01 | 16.9 | 1.89E+07 | 1.54E−01 | 15.3 |
| N99K | H | 7.89E+06 | 1.89E−01 | 23.9 | 1.58E+07 | 2.07E−01 | 20.7 |
| N99Q | H | 3.75E+05 | 4.93E−01 | 1314.1 | 1.03E+07 | 4.25E−01 | 42.4 |
| N99H | H | 1.33E+07 | 7.45E−03 | 0.7 | 6.20E+06 | 4.01E−03 | 0.4 |
| N99W | H | 9.22E+06 | 5.66E−01 | 61.3 | 5.27E+06 | 1.34E−01 | 25.3 |

Finally, the newly identified mutations were also tested in the full-length humanized antibodies previously generated (Table 6) and their selectivity for human fibrils was tested (Table 7B). Interaction kinetics were determined by using surface plasmon resonance technology on Biacore T200 instrument as described in Example 3. As shown in Table 7B, the mutations at position 33 in the light chain (with reference to SEQ ID NO: 19) and 56 and 102 in the heavy chain (with reference to SEQ ID NO: 27 and 35) result in increased affinity for human fibrils, which is an advantageous characteristic for antibodies that needs to cross the blood brain barrier to bind their target. When antibodies are administered systemically, a large quantity of the antibody administered may be lost because antibodies have limited systems to cross complex physiological barriers.

TABLE 7B

| Humanized antibodies | human monomer | | | human fibril | | |
|---|---|---|---|---|---|---|
| | ka1 (1/Ms) | kd1 (1/s) | KD1 (nM) | ka1 (1/Ms) | kd1 (1/s) | KD1 (nM) |
| VR6470 gL3; gH23 | 1.20E+06 | 0.02416 | 20.15 | 8.55E+05 | 1.42E−04 | 0.166 |
| VR6470 gL3; gH36 | 1.15E+06 | 0.01742 | 15.10 | 1.07E+06 | 3.17E−04 | 0.298 |
| VR6470 gL3; gH23-S56N-N102H | 9.66E+05 | 0.00445 | 4.62 | 1.04E+06 | 7.08E−05 | 0.068 |
| VR6470 gL3; gH36-S56N-N102H | 1.19E+06 | 0.00488 | 4.10 | 1.25E+06 | 7.44E−05 | 0.059 |
| VR6470 gL3-N33R; gH23-S56N-N102H | 3.48E+06 | 0.00594 | 1.71 | 2.07E+06 | 1.16E−04 | 0.056 |
| VR6470 gL3-N33R; gH36-S56N-N102H | 4.97E+06 | 0.00648 | 1.31 | 2.39E+06 | 1.26E−04 | 0.053 |

The variant humanized antibody chains, and combinations thereof, were expressed and assessed for their potency relative to the parent antibody, their biophysical properties and suitability for downstream processing.

Example 5: Characterization of Humanized Antibodies

Biophysical characterization was performed on six humanized 6470 IgG4P antibodies (Table 8, sequences in Table 1).

TABLE 8

| Descriptor |
|---|
| gL3gH23 |
| gL3gH36 |
| gL3-N33RgH23-S56N-N102H |
| gL3-N33RgH36-S56N-N102H |
| gL3gH23-S56N-N102H |
| gL3gH36-S56N-N102H |

All antibodies were screened based on thermal stability (Tm), experimental pI, hydrophobicity, solubility (PEG precipitation assay) and aggregation stability at an air/liquid interface to determine whether the mutations had any influence in particular with respect to affinity, stability and developability.

The screening process also included assessment of chemical stability (deamidation, Aspartic acid isomerization propensity) since the antibodies possess:
1. Asn(102)S motif (deamidation) in the heavy chain CDR3 for gL3gH23 and gL3gH36 only;
2. Asn(98)Asp(99) motif (deamidation) in the light chain CDR3 for all antibodies;
3. Asn(32)Asn(33) motif (deamidation) in the light chain CDR1 of all but N33 mutants;
4. Asp(99)G motif (Asp isomerization) in the light chain CDR3 for all antibodies Chemical instability at these sites could result in product heterogeneity and immunogenicity.

Thermal Stability ($T_m$) Measurements

The melting temperature (Tm) or temperature at the midpoint of unfolding, was determined using the Thermofluor assay. In this method, the fluorescent dye SYPRO® orange was used to monitor the protein unfolding process by binding to hydrophobic regions that become exposed as the temperature increases.

The reaction mix contained 5 µl of 30×SYPRO® Orange dye (Invitrogen™), diluted with PBS from 5000× stock solution and 45 µl of sample at 0.12 mg/ml, (in PBS pH 7.4).

About 10 µl of the mix was dispensed in quadruplicate into a 384 PCR optical well plate and was run on a 7900HT Fast Real-Time PCR System (Applied Biosystems™). The PCR system heating device was set at 20° C. to 99° C. with an increase rate of 1.1° C./min. A charge-coupled device monitored fluorescence changes in the wells. Intensity increases were plotted, and the inflection point of the slope(s) was used to calculate the Tm as described below.

Two unfolding transitions were observed for all antibodies. The first can be attributed to the Tm of the CH2 domain. The second can be attributed to an average of the Tm of the Fab unfolding domain and CH3 domain in accordance with the literature (Garber E, Demarest S J. Biochem Biophys Res Commun. 2007 Apr. 13; 355(3):751-7). Table 9 summarizes the results.

TABLE 9

| Descriptor | Fab domain $T_m$ | SD | CH$_2$ domain $T_m$ | SD |
|---|---|---|---|---|
| gL3gH23 | 73.1 | 0.6 | 64.8 | 0.2 |
| gL3gH36 | 73.5 | 0.3 | 64.7 | 0.0 |
| gL3gH23-S56N-N102H | 72.8 | 0.2 | 64.8 | 0.3 |
| gL3gH36-S56N-N102H | 73.4 | 0.2 | 65.1 | 0.3 |
| gL3-N33R-gH23-S56N-N102H | 73.9 | 0.5 | 65.2 | 0.1 |
| gL3-N33R-gH36-S56N-N102H | 73.3 | 0.2 | 64.7 | 0.3 |

Thermal stabilities are within the normal expected range (Heads et al "Relative stabilities of IgG1 and IgG4 Fab domains: influence of the light-heavy interchain disulfide bond architecture". Protein Sci. 2012 September; 21(9): 1315-22.) for IgG4 molecules.

Experimental pI

The experimental pI of the 6470 antibodies was obtained using the whole-capillary imaged cIEF iCE3™ system (ProteinSimple).

Samples were prepared by mixing the following: 30 µL sample (from a 1 mg/mL stock in HPLC grade water), 35 µL of 1% methylcellulose solution (Protein Simple), 4 µL pH 3-10 ampholytes (Pharmalyte), 0.5 µL of 4.65 and 0.5 µL 9.77 synthetic pI markers (ProteinSimple), 12.5 µL of 8M urea solution (Sigma-Aldrich®). HPLC grade water was used to make up the final volume to 100 µL. The mixture was vortexed briefly to ensure complete mixing and centrifuged at 10,000 rpm for 3 minutes to remove air bubbles before analysis. Samples were focused for 1 minute at 1.5 kV, followed by 5 minutes at 3 kV, and A280 images of the capillary were taken using the ProteinSimple software. The resulting electropherograms were first analyzed using iCE3 software and pI values were assigned (linear relationship between the pI markers). The calibrated electropherograms were then integrated using Empower® software (Waters).

The experimental pI for all of the 6470 antibodies was in the range of 8.4-9.2. There was a slight difference in the ratio of charged species between the molecules however this is not unexpected for an IgG4P molecule. All pIs were high and hence would aid in the manufacture process of the antibodies.

Hydrophobic Interaction Chromatography (HIC)

Hydrophobic Interaction chromatography (HIC) separates molecules in order of increasing hydrophobicity. Molecules bind to the hydrophobic stationary phase in the presence of high concentrations of polar salts and desorb into the mobile phase as the concentration of salt decreases. A longer retention time equates to a greater hydrophobicity.

Samples at 2 mg/mL were diluted 1:2 with 1.6 M ammonium sulphate and PBS (pH 7.4). 5 μg (5 μL) of sample was injected onto a Dionex ProPac™ HIC-10 column (100 mm×4.6 mm) connected in series to an Agilent 1200 binary HPLC with a fluorescence detector. The separation was monitored by intrinsic fluorescence (excitation and emission wavelengths, 280 nm and 340 nm respectively).

Using Buffer A (0.8 M ammonium sulphate 100 mM Phosphate pH7.4) and Buffer B (100 mM Phosphate pH7.4) the sample was analyzed using gradient elution as follows, (i) 2 minutes hold at 0% B, (ii) linear gradient from 0 to 100% B in 30 minutes (0.8 mL/minute) (iii) the column was washed with 100% B for 2 minutes and re-equilibrated in 0% B for 10 minutes prior to next sample injection. The column temperature was maintained at 20° C.

Standards exhibiting low and high hydrophobicity plus a control were also analyzed in the same run sequence to allow normalization of retention times (Table 11). The retention time (RT) of the sample was normalized against the low and high hydrophobicity standards using the following equation:

[(Sample (RT)−low standard (RT)/High standard (RT)−low standard (RT)]×100

TABLE 10

| Antibody (Major Peak) | Retention Time (min) | Normalised Retention Time (min) |
|---|---|---|
| gL3gH23 | 9 | 3.8 |
| gL3gH36 | 8.8 | 3.1 |
| gL3gH23-S56N-N102H | 8.9 | 3.5 |
| gL3gH36-S56N-N102H | 8.8 | 3.1 |
| gL3-N33RgH23-S56N-N102H | 8.8 | 3.1 |
| gL3-N33RgH36-S56N-N102H | 8.8 | 3.1 |

All 6470 antibodies and mutants showed similar normalized retention times and similar low hydrophobicity. Commercially available therapeutic antibodies tend to exhibit low hydrophobicity (Jain et al "Biophysical properties of the clinical-stage antibody landscape" Proc Natl Acad Sci USA. 2017 Jan. 31; 114(5):944-949.). Low hydrophobicity aids stability (i.e. reduce aggregation) during manufacture.

Solubility Measurement Using a Polyethylene Glycol (PEG) Precipitation Assay.

Colloidal stability was analyzed using a polyethylene glycol (PEG) precipitation assay. PEG was used to reduce protein solubility in a quantitatively definable manner, by increasing the concentrations of PEG (w/v) and measuring the amount of protein remaining in solution. This assay served to mimic the effect of high concentration solubility without using conventional concentration methods. PEG-induced precipitation of the 6470 antibodies was investigated in the presence of 7-18% PEG-3350 in PBS pH 7.4, 50 mM sodium acetate/125 mM sodium chloride pH 5.0 (Acetate pH 5) and 20 mM L-histidine, 140 mM NaCl, pH6.0. The samples were buffer exchanged where required using dialysis and the concentration adjusted to 2 mg/mL. In order to minimize non-equilibrium precipitation, sample preparation consisted of mixing 2× protein and 2× PEG solutions at a 1:1 volume ratio. After mixing, samples were incubated at 37° C. for 30 minutes to re-dissolve non-equilibrium aggregates. Following an overnight incubation at 20° C. the samples were centrifuged for 60 min (4000 g). Aliquots of the supernatant were transferred to half volume 96 well optical plates and the absorbance at 280 nm was measured using a plate-reader BMG Labtech FLUOstar® Omega LVIS A280. The concentration data was plotted versus PEG %, and the calculated midpoint (LogEC50), generated by a nonlinear curve fit, variable slope was obtained as a measure of the relative colloidal solubility of samples. In this assay, the higher LogEC50 equates to a greater colloidal stability.

The results (not shown) indicated that as buffer pH increased, the colloidal stability was reduced for all 6470 antibodies. In addition, the following trend was obtained, from most to less soluble gL3gH23 and gL3gH36>gL3gH23-S56N-N102H and gL3gH36-S56N-N102H>gL3-N33RgH23-S56N-N102H and gL3-N33RgH36-S56N-N102H.

Hence, mutations introduced for affinity maturation reduced the colloidal stability of the antibody molecules. No difference was observed between the gL3gH23 and gL3gH36 grafts.

Effect of Stress at Air-Liquid Interface (Aggregation Assay)

Proteins tend to unfold when exposed to an air-liquid interface, where hydrophobic surfaces are presented to the hydrophobic environment (air) and hydrophilic surfaces to the hydrophilic environment (water). Agitation of protein solutions achieves a large air-liquid interface that can drive aggregation. This assay serves to mimic stresses that the molecule would be subjected to during manufacture (for example ultra-filtration) and to provide stringent conditions in order to try to discriminate between different antibody molecules.

Samples in PBS pH 7.4, 50 mM sodium acetate/125 mM sodium chloride pH 5.0 (Acetate pH 5) and 20 mM L-histidine, 140 mM NaCl, pH6.0 were stressed by vortexing using an Eppendorf Thermomixer Comfort™. The buffers were chosen as common pre-formulation buffers. Prior to vortexing the concentration was adjusted to 1 mg/mL using the appropriate extinction coefficients (1.35 Abs 280 nm, 1 mg/mL, 1 cm path length) and the absorbance at 280 nm, 340 nm and 595 nm obtained using a Varian Cary® 50-Bio spectrophotometer to establish the time zero reading. Each sample was sub-aliquoted into 1.5 mL conical Eppendorf®-style capped tubes (4×250 μL) and subjected to stringent conditions in order to test robustness by vortexing at 1400 rpm at 25° C. for up to 24 hours. Time dependent aggregation (turbidity) was monitored by measurement of the samples at 3 hours and 24 hours post vortexing at 595 nm using a Varian Cary™ 50-Bio spectrophotometer. The mean absorbance values were plotted versus time for each sample.

Figure 11:
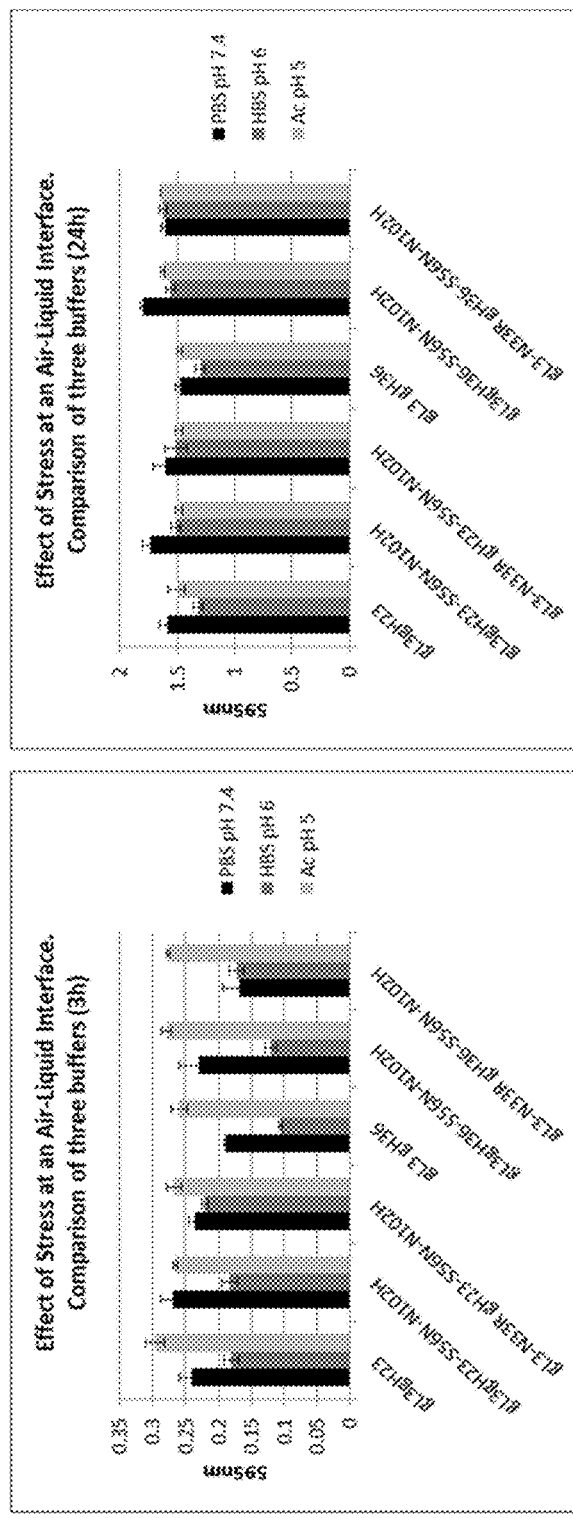
FIG. 11. Stress at an air-liquid interface. 6470 antibodies and mutants in three pre-formulation buffers at 3 and 24 hours post vortexing.

The results are illustrated in FIG. 11. There were no differences between the 6470 antibodies at 24 hours in any of the three buffers, however, small difference were discerned in aggregation propensity after 3 hours post vortexing which appeared to be buffer dependent.

Deamidation/Asp Isomerization Stress Study

A stress study was set up using 6470 antibodies gL3gH23 and gL3gH36 to determine deamidation/Asp-isomerization propensity of four identified potential sequence liabilities: Asn(102)S (deamidation motif) in the heavy chain CDR3; Asn(98)Asp(99) (deamidation motif) in the light chain CDR3; Asn(32)Asn(33) (deamidation motif) in the light chain CDR1 and Asp(99)G (Asp isomerisation motif) in the light chain CDR3. The propensity/rate of deamidation and Asp-isomerization cannot be predicted as it is dependent on primary sequence and 3D structure as well as solution properties (R C Stephenson and S Clarke (1989); K. Diepold et al (2012); Jasmin F. Sydow et al (2014); N. E. Robinson et al (2004)

The basal deamidation levels (non-stressed samples) were also obtained—low levels indicate low susceptibility but levels can change due to different manufacturing batches/conditions.

The two 6470 antibodies were buffer exchanged into buffers (i) known to favor deamidation of Asn(N) residues (Tris pH 8/37° C.) and (ii) known to favor Asp isomerization (acetate, pH 5/37° C.). The final concentration of sample in each of the buffers was adjusted to ~6.5 mg/mL and then split into two aliquots where one was stored at 4° C. and one at 37° C. for up to 4 weeks. An aliquot was removed immediately (T0) and at 2 weeks and 4 weeks and stored at −20° C.

The 2-week samples were thawed and analyzed by tryptic digestion/mass spectroscopy (MS) for chemical modification analysis as follows. Samples of stressed proteins were reduced with TCEP and alkylated with chloroacetic acid in Tris-HCL buffer pH 8.0 containing 0.1% w/v Rapigest detergent. Trypsin was added (1:25 w/w) and samples were digested overnight at room temperature. Proteolysis was stopped by adding formic acid to 1% v/v and samples were diluted to 0.5 mg/ml before centrifuging to remove precipitated Rapigest™. The resulting peptides were separated and analyzed on a Waters BEH C18 column interfaced to a Thermo Fusion™ mass spectrometer running a +ve-ion, data-dependent orbitrap-orbitrap method with collision induced dissociation (CID) fragmentation. LC-MS data was analyzed using Thermo Xcalibur™ and Pepfinder Software™.

Size Exclusion HPLC and SDS PAGE were also performed to monitor aggregation/degradation.

The results of the peptide mapping/mass spectrometry showed that the basal Asn deamidation level in all three CDR sites was <1.5% and that deamidation maximally increased by up to ~6% after 2 weeks at pH 8.0 and 37° C. for Asn(102)S site in the heavy chain CDR3.

Asp(99) modification (succinimide formation) in the light chain CDR3 was ~25% after 2 weeks at pH 5.0 and 37° C.

The effect of chemical modification (deamidation at Asn (102) on heavy chain CDR3 and formation of succinimide intermediate at Asp(99) on light chain CDR3) on affinity/avidity for recombinant full-length human alpha synuclein monomer and purified recombinant human alpha synuclein fibrils was assessed. A fully deamidated product (Asn(102) Asp) and stressed material (pH5/2 week/37° C.) were used in the study.

Example 6: Immunohistochemistry

Figure 12:
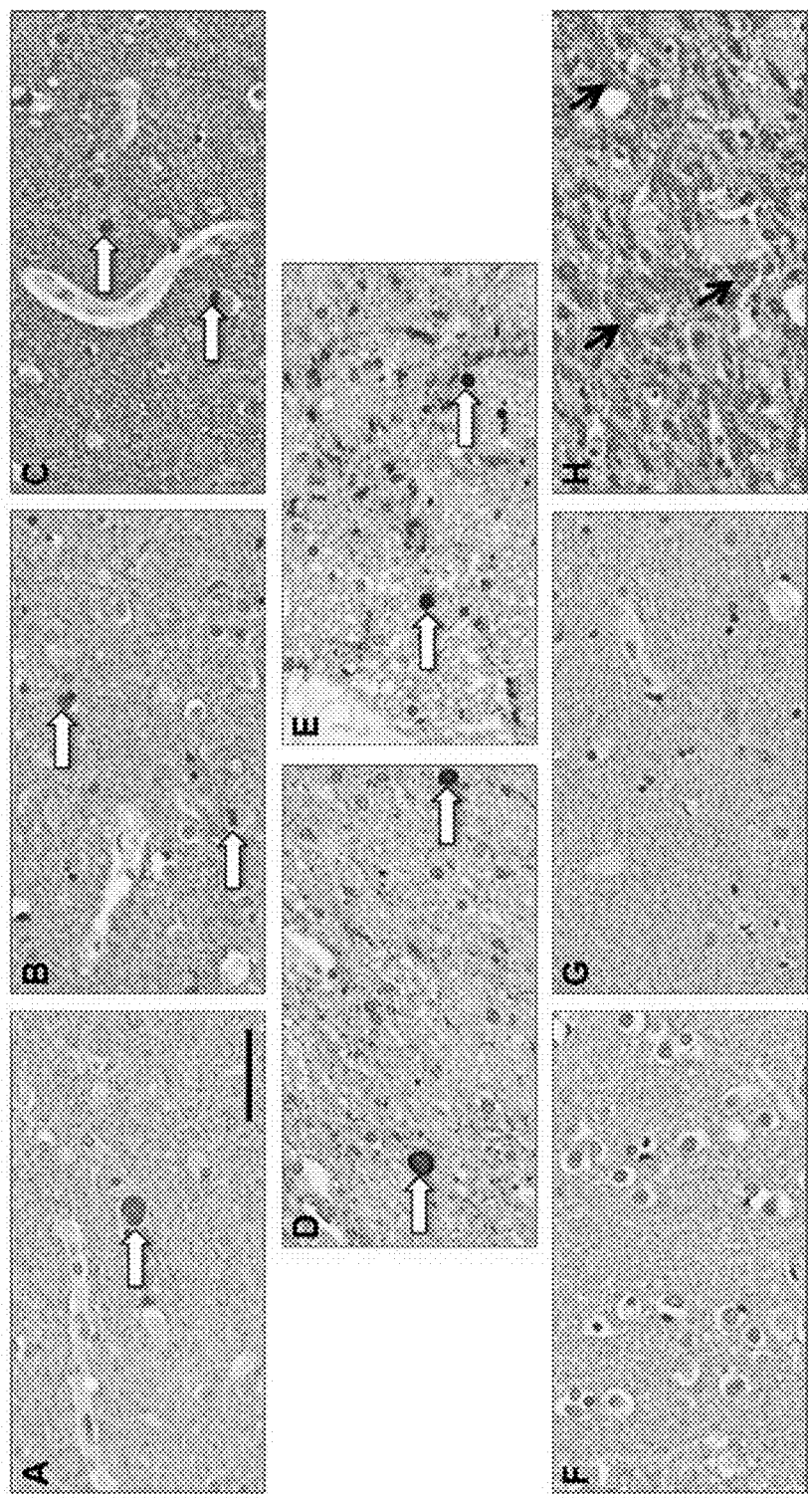
FIG. 12. Immunohistochemistry. Immunoreactivity in brain sections from (A-E) PD and (F-H) non-PD patients. (A-C) In the temporal cortex of PD patients, antibody 6470 labelled the neuropil and Lewy Body-like structures (white arrows) in the grey matter. (D, E) antibody 6470 labelled Lewy body-like features (white arrows) in the substantia nigra of PD patients. (F, G). In the non-PD temporal cortical tissues, 6470 labelled the neuropil as well, but no Lewy body-like structures were observed. (H) No Lewy body-like structures were observed in the substantia nigra of a non-PD individual; black arrows point to non-specific labelling. Scale bar=50 μm.

Immunohistochemistry was performed by Asterand Bioscience (Royston, United Kingdoms). Cryosections (10 μm) were first submitted to antigen retrieval procedure using Dako PT Link and EnVision FLEX Target Retrieval Solutions (pH 6) at 97° C. for 20 min with automatic heating and cooling. All following incubation steps were carried out at room temperature. Cryosections were air dried for 30 minutes, fixed in 4% paraformaldehyde prepared in 1×PBS for 10 minutes, washed in Dako EnVision™ FLEX Wash Buffer (Dako) and then loaded into a Dako Autostainer Plus. Endogenous peroxidase activity was blocked by incubating the sections with Dako peroxidase block (Dako) for 5 minutes. The sections were then washed twice with 1×PBS before incubating with Dako CSA II protein block (Dako) for 10 minutes. The protein block solution was removed by air jet and the sections incubated for 30 minutes with 6470 rabbit IgG1 (comprising SEQ ID NOs: 47 and 48) diluted (0.05 μg/ml) in Dako antibody diluent (Dako). Following incubation, the sections were washed twice with 1×PBS, then incubated with anti-rabbit Dako Flex polymer-HRP substrate (Dako) for 20 minutes, washed twice and then incubated with diaminobenzidine substrate (Dako) for 10 minutes. The chromogenic reaction was stopped by rinsing the slides with distilled water. Following chromogenesis, the sections were removed from the Dako Autostainer Plus and manually counterstained with haematoxylin, dehydrated in an ascending series of ethanol, cleared in three changes of xylene and cover slipped under DPX mounting medium (Sigma-Aldrich). Digital images of stained sections were obtained using an Aperio ScanScope AT Turbo system (Leica Biosystems). Antibody 6470 was tested on brain sections derived from five different pS129-α-synuclein-positive and three different pS129-α-synuclein-negative donors (1 section/donor). Antibody 6470 labeled the neuropil and Lewy body-like features in the temporal cortex and substantia nigra of PD patients (FIG. 12A-E). In the non-PD brain tissues, antibody 6470 labeled the neuropil in the temporal cortex, but no Lewy body-like structures were observed in the cortex or substantia nigra (FIG. 12F-H). These observations suggest that antibody 6470 binds to normal a-synuclein in the neuropil of brain tissues from PD and non-PD patients, while it binds to pathological a-synuclein present in Lewy bodies in PD-patients only.

Example 7: Cell-Based Aggregation Assay

HEK Freestyle 293F cells (suspension cells) were prepared at $0.7 \times 10^6$ cell/ml in Freestyle 293 Expression Medium (Invitrogen™) and cultured to $300 \times 10^6$ cell/ml. Transfection was performed according to manufacturer instructions and briefly 600 μg pcDNA3.1(+) incorporating the alpha-synuclein gene were mixed in 20 ml OptiMEM medium whilst 293Fectin was diluted in OptiMEM medium (Invitrogen™) and incubated for 5 minutes at room temperature. The diluted DNA was added and incubated at room temperature for 20 minutes before to be added drop by drop on the cells (20 ml per flask). The cells were incubated for 24 hours at 37° C., 125 rpm, 8% $CO_2$. Cells were either used immediately or frozen at concentration of 5 million cells/ml in FBS+10% DMSO.

If the cells had been previously frozen cryovials were thawed and cells resuspended in Freestyle 293 medium, centrifuged at 500 g for 5 minutes, the supernatant was discharged and the pellet was resuspended in Freestyle 293 medium (Life Technologies™) comprising Pen/Strep (Invitrogen™) at $2 \times 10^6$ cells/ml. In a 384-well plate (Grainer™), 20 μl of cell suspension was added (to a total of ca. 40,000 cells/well). To each well, 150 nM of human alpha-synuclein fibrils (prepared as described herein in Example 1) were added followed by the antibodies (6470 gL3gH23; 6470 gL3gH36; 6470 gL3N33gH23 S56N N102; 6470 gL3N33gH36 S56N N102; 6470 gL3gH23 S56N N102; 6470 gL3gH36 S56N N102; all as full-length IgG4P, sequences in Table 1) in PBS to be tested (at various concentrations). The plates were incubated at 37° C., 5% $CO_2$, 95% humidity in a cell culture incubator for 2 days.

At the end of the second day, the medium was aspirated from all wells and the plate washed leaving 20 µl per well. About 50 µl of PBS was added to each well and the plates were centrifuged at 500 g for 5 minutes. The supernatant was aspirated from all wells with a plate washer, leaving 20 µl of medium in each well. Versene (Lonza™) was added (50 µl/well) and the plates were centrifuged at 500 g for 5 minutes, the supernatant was aspirated leaving only 20 µl of medium per well. Each well was supplemented with 20 µl 8% formaldehyde (16% solution in water, Life Technologies™)+2% Triton X-100 (VWR™) in PBS. The plates were incubated at room temperature for 15 minutes and thereafter 50 µl of FACS buffer consisting of HBSS (calcium-magnesium free VWR™)+2% FBS+2 mM EDTA, (Life Technologies™) were added. The plates were centrifuged at 2000 g for 1 minute and the supernatant was aspirated only leaving 20 µl of medium in each well. Each well was further supplemented with 20 µl of FACS buffer with anti-pSer129 alpha-synuclein antibody (AbCam™) diluted 1:300. The plates were incubated for 1 hour at room temperature and then each well was supplemented with 50 µl of FACS buffer before centrifuging again at 2000 g for 1 minute. The supernatant was removed before each well was supplemented with 1:500 diluted Alexafluor647-conjugated anti-rabbit-secondary antibody (Life Technologies™) and DAPI (Life Technologies™). Plates were incubated 1 hour at room temperature in the dark, and then 50 µl of FACS buffer was added and the plates centrifuged at 2000 g for 1 minute. Upon washing, more FACS buffer was added and the plates were ready to be placed in the flow cytometer (BD FACS Canto II) for reading.

FACS data were analyzed using the FlowJo software. Firstly, live single cells were gated using forward and side scatter. Secondly, DAPI+ events were gated and their number was used as a measure of the number of live, nucleated single cells. Finally, phospho-serine 129-alpha-synuclein-positive (pSer129+) cells were gated. The percentage of pSer129+ cells relative to all DAPI+ cells was used as a measure of aggregation. Data were normalized relative to the wells treated with only fibrils and no antibody, and expressed as a percentage.

Figure 13:
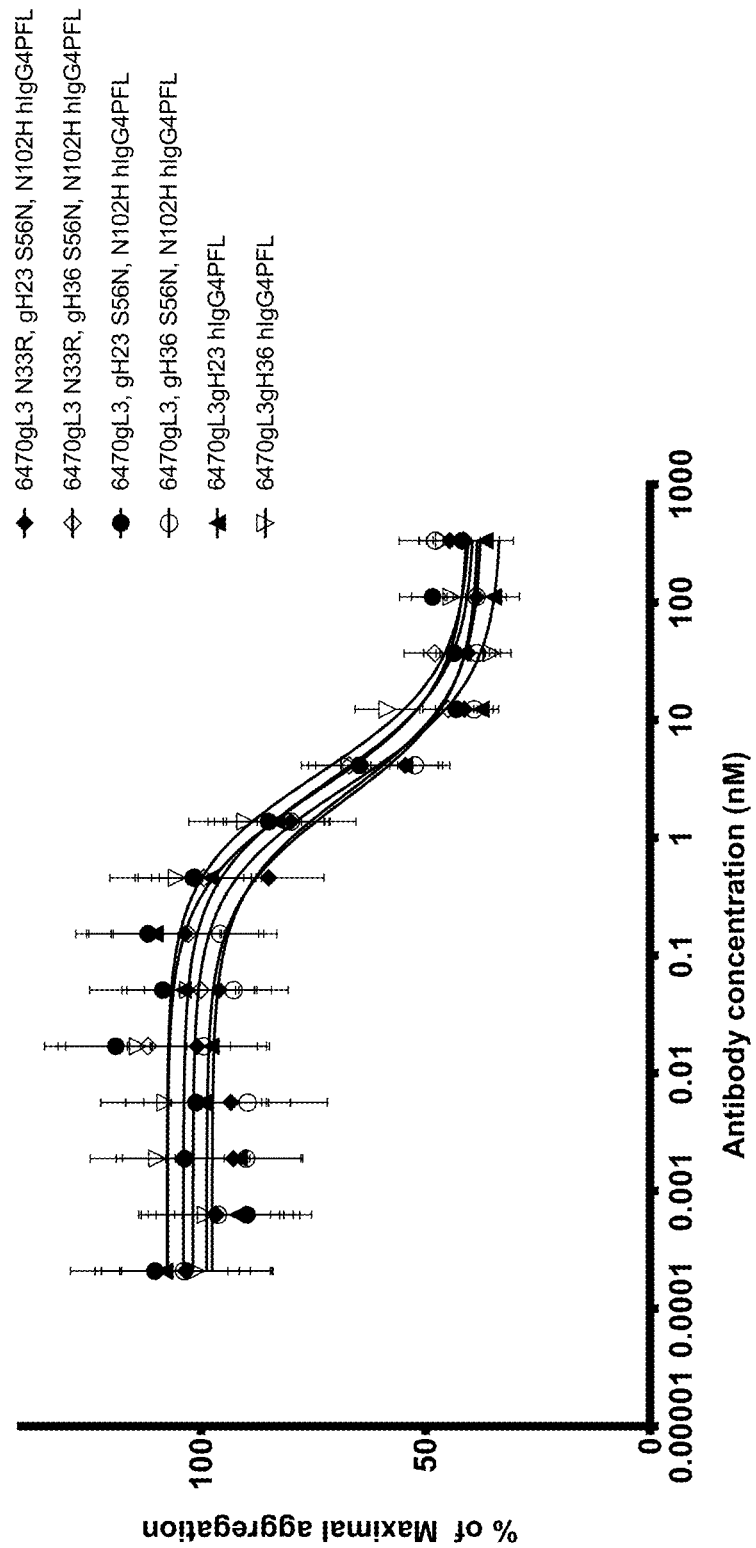
FIG. 13. Cell-based aggregation assay (HEK cells). Antibodies of the present invention were able to inhibit alpha synuclein aggregation induced by alpha-synuclein fibrils, with IC$_{50}$ below 5 nM. Error bars represent standard error of measurement (SEM, N=3, n=9). In the legend, FL at the end of each antibody names means "full length".

The results are summarized in FIG. 13 which shows the ability of the antibodies tested to inhibit aggregation induced by alpha synuclein fibrils on cell expressing alpha synuclein. These data confirm that the antibodies of the present invention were able to block the aggregation induced by alpha-synuclein fibrils, with $IC_{50}$ below 5 nM.

Error bars represent standard error of measurement (SEM, N=3, n=9).

Example 8: Primary Neurons Appreciation Assay

Hippocampi from E17 mouse embryos were dissected in dissection buffer (HBSS with no calcium and no magnesium, 0.6% D-(+)-Glucose, 20 mM Hepes). The dissection buffer was then removed and replaced by a dissociation solution (HBSS with no calcium and no magnesium, 0.6% D-(+)-Glucose, 20 mM HEPES, 40U/m Papain, 1 mg/ml DNase, 1 mM L-cysteine, 0.5 mM EDTA). After 30 minutes incubation at 37° C., the dissociation buffer was removed and hippocampi were washed 3× with plating medium (Neurobasal™ Medium, 2% B27 supplement, 1 mM GlutaMAX, 2.5% FBS, 50 units/ml Penicillin-Streptomycin). Tissue clumps were triturated with a 1 ml pipette to obtain a single cell suspension. Cells were diluted to the appropriate concentration in plating medium. About 15000 cells were plated in each well of a PDL-coated 384-well plate. Cells were then kept in a cell culture incubator, at 37° C., 5% $CO_2$, 95% humidity.

The next day, 80% of the medium was replaced with plating medium without FBS [Neurobasal™ Medium, 2% B27 supplement, 1 mM GlutaMAX, 50 units/ml Penicillin-Streptomycin). Seven days after plating, the medium was removed leaving 20 µl in each well. To each well, 100 nM of human alpha-synuclein fibrils (prepared as described herein in Example 1) were added followed by antibody 6470 (6470gL3gH36 hIgG4P; VR6470 in FIG. 14 comprising SEQ ID NO: 17 and SEQ ID NO: 33) in PBS to be tested (at various concentrations). The plate was incubated at 37° C., 5% $CO_2$, 95% humidity in a cell culture incubator for an additional 7 days. Fourteen days after plating, the medium was aspirated from all wells leaving 20 µl per well. Each well was washed with 80 µl of Dulbecco's Phosphate Buffered Saline (DPBS). The DPBS was removed, and cells were incubated in 40 µl of fixation buffer (DPBS with 4% paraformaldehyde) per well for 15 minutes. The fixation buffer was then removed and cells were washed again with 80 µl of DPBS. The DPBS was removed and replaced by 40 µl of permeabilization buffer (DPBS with 0.1% Triton X-100) per well. After 10 minutes, the permeabilization buffer was removed, and cells were incubated for 1 hour in 40 µl of blocking buffer (PBS with 1% BSA and 0.1% Triton X-100) per well. The blocking buffer was then removed and replaced by 40 µl/well of primary antibody solution (blocking buffer with 0.3% rabbit anti-phospho-serine 129 alpha-synuclein antibody (AbCam™ ab51253). The antibody solution was incubated on the cells for 1h, followed by three washes (90 µl/each, PBS). After the last wash, the PBS was removed and replaced by 40 µl of secondary antibody solution (0.1% AlexaFluor647-conjugated anti-rabbit antibody in PBS with 0.2% AlexaFluor488-conjugated anti-beta-III-tubulin antibody). The secondary antibody solution was incubated on the cells for 1h, then removed and replaced by 40 µl of PBS comprising 0.3% CellMask Blue™. After 5 min of incubation, the wells were washed 3 times with 80 µl of PBS, then filled with 50 µl of PBS per well before the plate was sealed with clear plastic film.

Plates were imaged in an Arrayscan plate imager (ThermoFisher Scientific™). Images were analyzed using the HCS Scan™ software from the same manufacturer. Neuronal density was monitored using the beta-III-tubulin signal. Sparse fields or fields showing a damaged neuronal cell layer, reflected by a significant decrease in the surface of beta-III-tubulin signal, were excluded. Finally, the surface of pSer129 alpha synuclein signal per field was used to quantify pathological alpha-synuclein aggregation.

Phosphorylation at S129 of alpha synuclein is believed to play an important role in the control of alpha synuclein normal functions, as well as the regulation of its aggregation, LBs formation and neurotoxicity. Under normal conditions, only a small fraction of alpha synuclein is constitutively phosphorylated at S129 in the brain (Fujiwara H, et al. (2002) Nat Cell Biol, 4, 160-164), whereas a dramatic accumulation of pS129 has been observed in the brains of patients suffering from synucleinopathies (Kahle P J, et al. (2000) Ann NY Acad Sci, 920, 33-41); Okochi M, et al. (2000) J Biol Chem, 275, 390-397); Anderson J P, et al. (2006) J Biol Chem, 281, 29739-29752).

Figure 14:
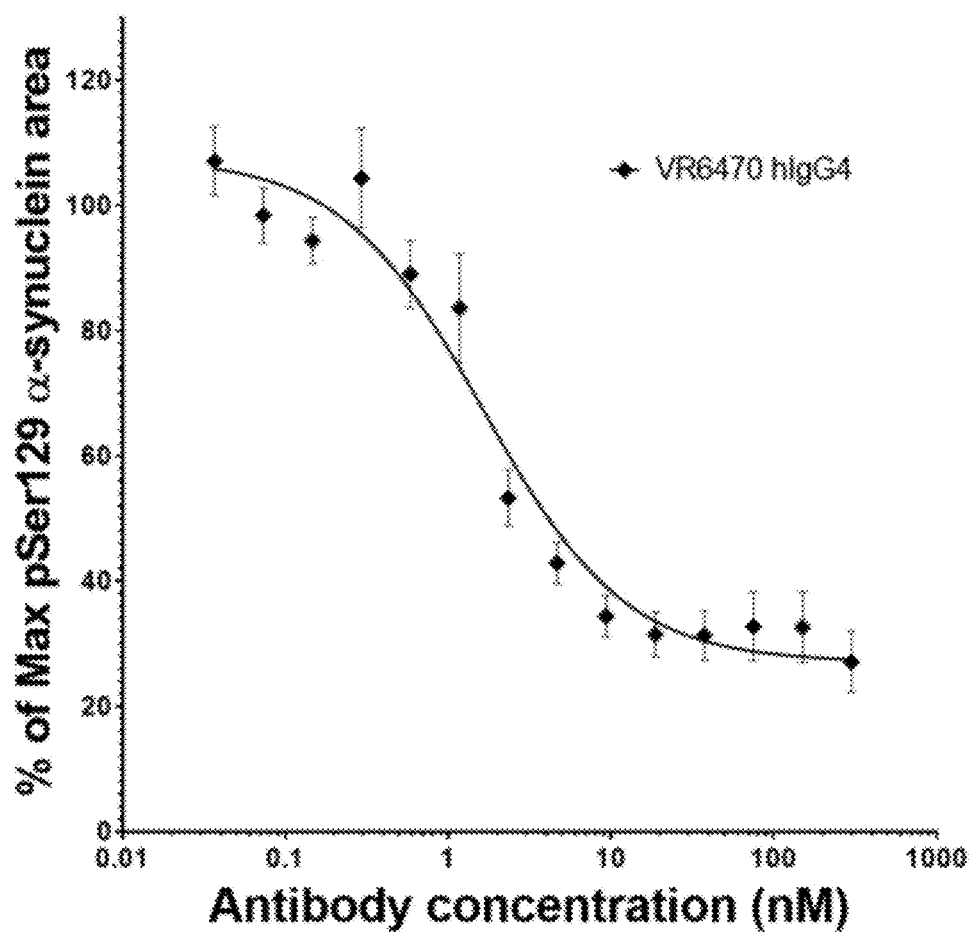
FIG. 14. Cell-based aggregation assay (primary neurons). A representative antibody according to the present invention was able to inhibit alpha synuclein aggregation induced by alpha synuclein fibrils on mouse primary neurons expressing endogenous levels of alpha synuclein, with an IC$_{50}$ below 4 nM. Error bars represent standard error of measurement (SEM, N=4, n=18).

Data were normalized relative to the wells treated with only fibrils and no antibody, and expressed as a percentage. As shown in FIG. 14, 6470gL3gH36 (indicated as VR6470) inhibits alpha synuclein aggregation induced by alpha synuclein fibrils on mouse primary neurons expressing endogenous levels of alpha synuclein. Error bars represent standard error of mean (SEM, N=4, n=18). These data confirm that 6470gL3gH36 was able to block the aggregation induced by alpha synuclein fibrils on mouse primary neurons, with $IC_{50}$ lower than 4 nM.

Example 9: Assessment of VR6470 Efficacy In Vivo

Antibody 6470gL3gH36 IgG4P (named in this example VR6470 and comprising SEQ ID NO: 17 and SEQ ID NO: 33) is tested in wild type male mice C57Bl/6J (Janvier, France) and in a transgenic model of a-synuclein knockout mouse expressing human alpha synuclein (thereafter named SNCA-OVX; Charles River, France).

C57Bl/6J and SNCA-OVX mice are injected with 6470gL3gH36 IgG4P and murine pre-formed fibrils (PFF) (prepare as described herein in Example 1). A negative control antibody (101.4) and vehicle are also injected along with a comparator anti-alpha synuclein antibody (comparator C-term Ab) which binds alpha synuclein at the last nine C-terminal residues. Such comparator antibody (which has different CDRs from the antibodies according to the present invention) shows comparable binding characteristics to the antibodies of the present invention. The comparator antibody possesses higher affinity for alpha synuclein than antibodies of the present invention and similar biophysical properties. It is also equally effective in preventing alpha synuclein aggregation on HEK cell-based assays according to example 8.

The antibodies are preincubated with the PFFs for 30 minutes, on a shaker at room temperature, before direct administration in the brain of the animals. The antibodies/PFFs mixtures are prepared in PBS at a ratio of 1 µg PFFs/10 µg antibodies. PBS at pH 7.4 is used as the vehicle solution. One injection is done 24 hours before the combined intracerebral administration The antibodies are then administered intraperitoneally to mice at a dose of 30 mg/kg. The second intraperitoneal injection is given 7 days after the first one, and then is pursued with the same regimen (one intraperitoneal injection/week at a dose of 30 mg/kg for a volume of administration of 10 ml/kg) for 4 weeks for a total of 4 injections for wild type male mice C57Bl/6J and for 11 weeks for a total of 12 injections for SNCA-OVX mice. For both experiments, the mice are randomly assigned to the drug treatment groups and the experimenters are blind to the treatment.

Animal experiments are performed according to the guidelines of the European Directive 2010/63/EU and Belgian legislation. The ethical committee for animal experimentation from UCB Biopharma SPRL (LA1220040 and LA2220363) approves the experimental protocol (ASYN—IC-PARKINSON-MO). The mice weigh between 25 and 30 g and are 17-week old at the time of surgery. The mice are housed in cages (4 mice per cage, Macrolon type 2). They are kept on a 12:12 light/dark cycle with light on at 06:00h. The temperature is maintained at 20-21° C. and humidity is of approximately 40%. All animals have free access to standard pellet food and water before assignment to experimental groups. Additional enrichment and welfare are provided (Enviro-dri, Pharma Serv) before and after surgery. Animal health is monitored daily by the animal care staff. All efforts are made to minimize suffering. Sacrifice are done under anesthesia.

Surgery is performed under general anesthesia using a mixture of 50 mg/kg of ketamine (Nimatek, Eurovet Animal Health B.V.) and 0.5 mg/kg of medetomidine (Domitor, Orion Corporation) is injected intraperitoneally. In addition, 2.5 mg/kg atipamezole (Antisedan, Orion Corporation) is given to support awakening. The recombinant purified PFFs are thawed and sonicated at room temperature (Qsonica 500-20 kHz; 65% power, for 30 pulses of 1 s ON, 1 s OFF for one minute). The PFFs are then premixed with the antibodies for 30 minutes and shaken at room temperature for 30 minutes before brain injection. The solution (2 µl) is infused at a rate of 0.2 µl/min and the needle is left in place for an additional 2.5 minutes before its slow retraction. Injections are carried out unilaterally in the right striatum at the following coordinates: AP=+0.20 mm, ML=−2.00 mm, DV=−3.20 mm.

Following anesthesia, the mice are perfused by transcardiac perfusion with ice-cold 0.9% PBS containing 10 U/ml heparin for 9 minutes at a flow rate of 6 ml/min via the left ventricle. The right atrium is cut as an outflow route. Subsequently, the animals are perfused with ice-cold 4% paraformaldehyde in PBS for 15 minutes at a flow rate of 6 ml/min. The brains are post-fixed overnight in PBS containing 4% paraformaldehyde at 4° C. (day 0). The next morning (day+1), the 4% paraformaldehyde is discarded and the brains are washed in cold PBS and incubated overnight. The next day (day+2) the brains are washed in PBS for a minimum of 1 hour and transferred to PBS containing 15% sucrose and stored at 4° C. until shipment.

Brain sectioning is performed at Neuroscience Associates (TN, USA). First, brains are treated overnight with 20% glycerol and 2% dimethyl sulfoxide to prevent freeze-artifacts, and embedded in a gelatin matrix using Multi-Brain® Technology. After curing, the blocks are rapidly frozen by immersion in isopentane chilled to −70° C. with crushed dry ice, and mounted on the freezing stage of an AO860 sliding microtome. The MultiBrain® blocks are sectioned in the coronal plane at 40 µm. All sections are collected sequentially into 24 containers per block that are filled with Antigen Preserve solution (49% PBS pH 7.0, 50% Ethylene glycol, 1% Polyvinyl Pyrrolidone). Sections not stained immediately are stored at −20° C.

Free-floating sections are stained by immunochemistry with pSer129 alpha synuclein antibody (mouse anti alpha synuclein (pSer129) Biotin—(Wako—010-26481)), diluted at 1:30.000. All incubation solutions from the blocking serum onward use Tris buffered saline (TBS) with Triton X-100 as the vehicle; all rinses are with TBS. Endogenous peroxidase activity is blocked by 0.9% hydrogen peroxide treatment and non-specific binding is blocked with 1.26% whole normal serum. Following rinses, the sections are stained with a primary antibody overnight at room temperature. Vehicle solution contains 0.3% Triton X-100 for permeabilization. Following rinses, sections are incubated with an avidin-biotin-HRP complex (Vectastain Elite ABC kit, Vector Laboratories, Burlingame, Calif.) for one hour at room temperature. Following rinses, the sections are treated with diaminobenzidine tetrahydrochloride (DAB) and 0.0015% hydrogen peroxide to create a visible reaction product, mount on gelatinized (subbed) glass slides, air-dry, lightly stain with thionine, dehydrate in alcohols, clear in xylene, and cover-slip with Permount.

Fluorescent immunohistochemistry for p62/SQSTM1 (p62 is known to co-aggregate in Lewy bodies in human) and Amytracker (for protein aggregates in general) stainings are performed on floating brain sections.

Quantification of pSer129 alpha synuclein signal per field pSer129 alpha synuclein signal is used to quantify pathological alpha synuclein aggregation in the ipsilateral side of the striatum, cortex, basolateral amygdala, and substantia nigra. Regions of interest (ROI) are delineated manually and automatic quantification of pSer129 alpha synuclein signal in the different brain regions is performed with VisioPharm 6 software (VisioPharm). To quantify pSer129 alpha synuclein signal, the linear Bayesian algorithm, which provides a value of signal area (marker area in µm2), is used.

Marker area reflects the amount of pSer129 alpha synuclein pathology that covers the different brain regions. All quantifications are done blindly until the end of statistical analysis.

The data analyses are done on the % marker area (i.e. ratio between the pSer129 signal area in $\mu m^2$ and the Region of Interest area in $\mu m^2$). The % marker area is assessed repetitively for multiple brain sections positioned rostro-caudally (striatum: 13-14 sections from Bregma+1.1 to −0.94; cortex: 13-14 sections from +1.1 to −0.94; basolateral amygdala: 6-10 sections between −0.58 to −2.06; substantia nigra: 6-8 sections from −2.54 to −3.88), and an AUC is calculated separately for every tested subject.

One-way ANOVA are considered for statistical analysis. The ANOVA are followed by multiple pairwise comparisons among means without any multiplicity adjustment. (with **, for p<0.01 and *, for p<0.05). The data are log-transformed to meet the normality and homoscedasticity criteria. The graphs represent the geometric means of the untransformed data.

The antibody of the present invention can be used for treating alpha synucleinopathies for example when characterized by an increase of Ser129 phosphorylation, including Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1).

Example 10: Pharmacokinetics of Antibody 6470 in Mouse

Figure 15A:
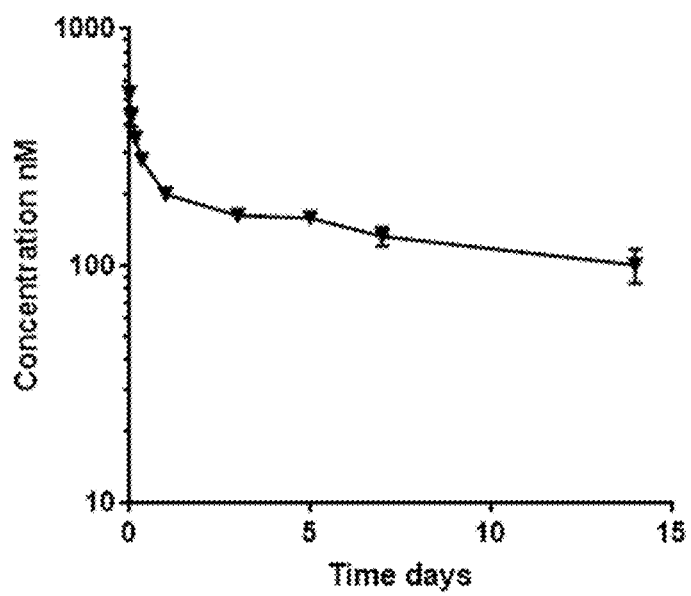
FIGS. 15A and 15B. Pharmacokinetic profiles of alpha synuclein antibodies: A. 6470 antibody in wild type mouse; B. 6470 and comparator antibodies in cynomolgus monkey.

Male C57/Bl6 mice (n=3 per drug) were injected intravenously as a single dose of 2 mg/kg with antibody 6470gL3gH36 IgG4P (comprising SEQ ID NOs: 17 and 33; in FIG. 15 and hereinafter simply referred as 6470).

Blood samples were taken (0.083, 1, 4, 8, 24, 72, 120, 168 & 336 hours from injections) from the tail vein and allowed to clot at room temperature. Serum was isolated after centrifugation, which was then frozen until analysis. Quantification of 6470 was carried out by LC-MS/MS. Serum samples from the study were defrosted and quantified against a calibration line prepared using 6470 or the comparator antibody spiked at different concentrations into control mouse serum. Before injecting the samples onto the LC-MS/MS system, the serum was denatured, reduced and alkylated using acetonitrile (VWR, UK), TCEP-Tris(2-carboxyethyl) phosphine hydrochloride (Sigma, UK) and Iodoacetamide (Sigma, UK) respectively. The alkylated samples were then reconstituted in 100 mM ammonium bi-carbonate buffer (Sigma, UK) and digested overnight using trypsin (Promega, UK) enzyme at 37° C. The digestion was stopped by adding formic acid to the samples to lower the pH and then desalted using Waters HLB SPE plate. The resulting eluent was evaporated using vacuum evaporator. After the samples were completely dried they were reconstituted with 95/5: Water/Acetonitrile containing 0.1% formic acid and injected onto the LC-MS/MS system. LC-MS/MS analysis was carried out by Schimadzu prominence HPLC system coupled to AB Sciex QTrap 6500 triple quadruple mass spectrometer. The digested sample was injected by the autosampler onto a reversed-phase high-performance liquid chromatography column (Phenomenex Aeris C18 peptide column 100×2.1 mm, 2.6 μm) which was maintained at 50° C. A linear gradient of 5-70% acetonitrile in 0.1% formic acid was applied for 6 minutes and then ramped to 95% acetonitrile in 0.1% formic acid over 0.8 minutes at a flow rate of 0.6 ml/min. The mass spectrometer was set up to run multiple reaction monitoring analysis to detect multiple transitions of peptides of 6470 or 5811 at a dwell time of 50 milliseconds per transition. Data analysis was carried using Analyst 1.6 software version.

These data demonstrate that antibody 6470 possesses very good pharmacokinetic properties (Table 11 and FIG. 15A) in mouse, based on the low clearance values measured. These appear to be superior to the typical ranges quoted for human IgG drugs dosed to mice (3-16 ml/day/kg; Deng et al 2011 mabs 3:1 61-66).

The pharmacokinetic property of antibody 6470 were also investigated in cynomolgus monkeys and compared to a prior art antibody. Male cynomolgus monkeys (n=3 or n=6 per drug) were injected intravenously as a single dose of either 2 or 3 mg/kg of antibody 6470gL3gH36 IgG4P (6470) and another comparator anti-alpha synuclein antibody (anti alpha synuclein IgG1 antibody binding alpha synuclein within amino acid 118-126; WO2013/063516).

Blood samples were taken at multiple timepoints (0.083, 1, 3, 6, 24, 48, 96, 168, 240, 336, 504, 576, 672 hours from injections) and allowed to clot at room temperature. Serum was isolated after centrifugation, which was then frozen until analysis. Samples were defrosted and analyzed using LC/ESI MS/MS. For 6470, the method described herein before in this Example was used, with quantification done by setting up a standard curve in cynomolgus serum. For the comparator antibody, horse myoglobin was used as an internal standard and quantification done by comparing signals to the internal standard signal. For preparation, samples were mixed with internal standard. Samples were then denatured, alkylated and consequently submitted to overnight enzymatic digestion (trypsin). After digestion, samples are diluted and the signature peptides for all analytes are submitted to LC-MS/MS analysis. Samples were only prepared once and injected twice (once for each method).

Concentration-time profiles were analyzed using Pharsight Phoenix 6 using non-compartmental analysis to derive clearance and half-life pharmacokinetic parameters for each individual animal. Mean and standard deviation parameters were reported for each molecule.

Figure 15B:
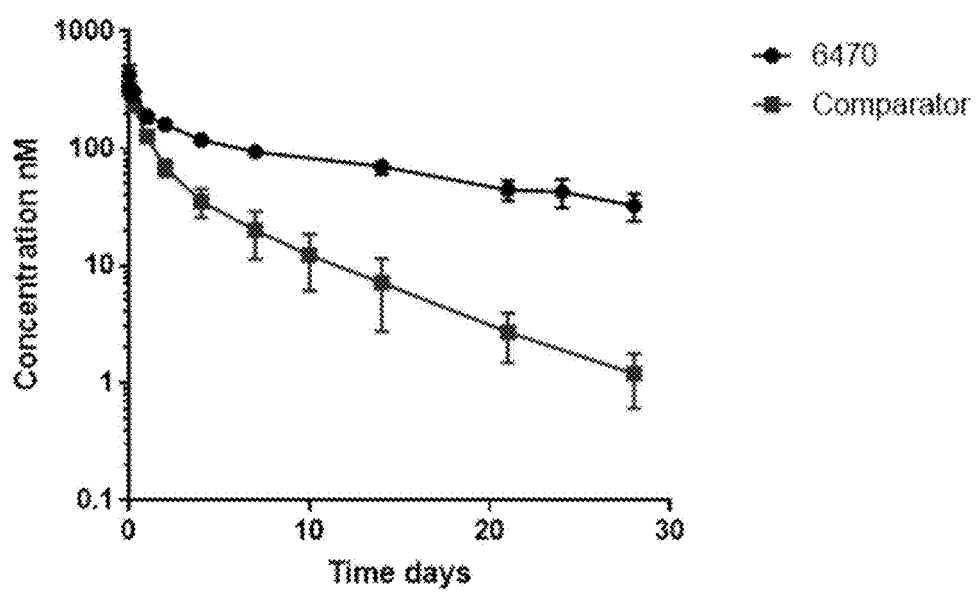

As shown in FIG. 15B and in Table 11 antibody 6470 exhibits also excellent pharmacokinetic properties in cynomolgus monkey exhibiting low clearance. As in mouse, its pharmacokinetic behavior appears to be superior to the typical range quoted for human IgG drugs dosed to cynomolgus monkeys (5-12 ml/day/kg; Deng et al 2011 mabs 3:1 61-66).

The fast clearance in cynomolgus observed for the comparator antibody is consistent with the published human data (JAMA Neurology 2018, 75, 10:1206-14). Antibody 6470 is superior to the comparator antibody in both exposure and clearance compared to the comparator antibody which exhibits poor, atypical pharmacokinetic features and parameters.

TABLE 11

| Antibody | Clearance (SD) ml/day/kg | |
| --- | --- | --- |
|  | Mouse | Cynomolgus |
| 6470 | 3.1 (0.7) | 4.7 (0.8) |
| Comparator |  | 23.4 (9.8) |

The invention claimed is:

1. An antibody that binds to alpha synuclein or an antigen binding fragment of the antibody, wherein the antibody or the antigen binding fragment of the antibody comprises:
   a) a light chain variable region comprising:
      i) a CDR-L1 comprising SEQ ID NO: 1;
      ii) a CDR-L2 comprising SEQ ID NO: 2; and
      iii) a CDR-L3 comprising SEQ ID NO: 3; and
   b) a heavy chain variable region comprising:
      i) a CDR-H1 comprising SEQ ID NO: 4;
      ii) a CDR-H2 comprising SEQ ID NO: 5; and
      iii) a CDR-H3 comprising SEQ ID NO: 6.

2. The antibody or antigen-binding fragment of claim 1, wherein the antibody comprises a light chain variable region comprising SEQ ID NO: 15 and a heavy chain variable region comprising SEQ ID NO: 31.

3. The antibody or antigen-binding fragment of claim 1, wherein the antibody comprises a light chain comprising SEQ ID NO: 17 and a heavy chain comprising SEQ ID SEQ ID NO: 33.

4. The antibody or the antigen-binding fragment of claim 1, wherein the antibody binds an alpha synuclein epitope comprising, with reference to SEQ ID NO: 10, residues E123, Y125, E126, M127, P128, S129, E130 and E131, wherein the epitope optionally comprises A124 and G132.

5. The antibody or antigen-binding fragment according to claim 1, wherein the antibody or antigen-binding fragment prevents aggregation of alpha synuclein induced by alpha synuclein fibrils.

6. The antibody or the antigen-binding fragment of claim 1, wherein the antibody or antigen-binding fragment is capable of binding alpha synuclein as a monomer and in fibrils.

7. The antibody or the antigen-binding fragment of claim 1, wherein the antibody or the antigen-binding fragment has a higher binding affinity for alpha synuclein in fibrils compared to monomeric alpha synuclein characterized by a constant of dissociation (KD) at least 10-fold higher for monomeric alpha synuclein than for alpha synuclein in fibrils.

8. The antibody or the antigen-binding fragment of claim 1, wherein the antibody or the antigen-binding fragment has a (KD) for alpha synuclein in fibrils of 300 pM or less.

9. The antibody or the antigen-binding fragment of claim 1, wherein the antibody or the antigen-binding fragment does not bind beta synuclein and/or gamma synuclein.

10. The antibody or the antigen-binding fragment of claim 1, wherein the antibody is a chimeric or humanized antibody.

11. The antibody or antigen-binding fragment of claim 1, wherein the antibody is a full length antibody.

12. The antibody or antigen-binding fragment of claim 11, wherein the full-length antibody is an IgG1, IgG4 or IgG4P.

13. The antibody or antigen-binding fragment of claim 1, wherein the antigen-binding fragment is a Fab, a Fab', a F(ab')2, or a scFv.

14. An isolated polynucleotide encoding the antibody or the antigen-binding fragment of claim 1.

15. The isolated polynucleotide according to claim 14, wherein the polynucleotide encodes:
   a. a light chain variable region, wherein the polynucleotide:
      i) comprises a sequence that is at least 90% identical to SEQ ID NO: 16; or
      ii) comprises SEQ ID NO: 16; or
   b. a heavy chain variable region, wherein the polynucleotide:
      i) comprises a sequence that is at least 90% identical to SEQ ID NO: 32; or
      ii) comprises SEQ ID NO: 32.

16. A host cell comprising the polynucleotide of claim 14.

17. A cloning or expression vector comprising the polynucleotide of claim 14.

18. A host cell comprising the expression vector of claim 17.

19. A process for producing the antibody or antigen-binding fragment of claim 1, comprising culturing a host cell comprising a polynucleotide encoding the antibody or antigen-binding fragment under suitable conditions for producing the antibody or antigen-binding fragment and isolating the antibody or antigen-binding fragment.

20. A pharmaceutical composition comprising the antibody or antigen-binding fragment of claim 1 and one or more pharmaceutically acceptable carriers, excipients or diluents.

21. An antibody that binds to alpha-synuclein or an antigen-binding fragment of the antibody, wherein the antibody comprises a light chain variable region that is at least 80% identical to SEQ ID NO: 15 and a heavy chain variable region that is at least 80% identical to SEQ ID NO: 31, wherein the antibody or the antigen-binding fragment of the antibody comprises:
   i) a CDR-L1 comprising SEQ ID NO: 1;
   ii) a CDR-L2 comprising SEQ ID NO: 2;
   iii) a CDR-L3 comprising SEQ ID NO: 3;
   iv) a CDR-H1 comprising SEQ ID NO: 4;
   v) a CDR-H2 comprising SEQ ID NO: 5; and
   vi) a CDR-H3 comprising SEQ ID NO: 6.

* * * * *

SEQUENCE LISTING

<160> NUMBER OF SEQ ID NOS: 49

<210> SEQ ID NO 1
<211> LENGTH: 13
<212> TYPE: PRT
<213> ORGANISM: Oryctolagus cuniculus

<400> SEQUENCE: 1

Gln Ala Ser Gln Ser Val Tyr Lys Asn Asn Tyr Leu Ala
1               5                   10

<210> SEQ ID NO 2
<211> LENGTH: 7
<212> TYPE: PRT
<213> ORGANISM: Oryctolagus cuniculus

<400> SEQUENCE: 2

Gly Ala Ser Thr Leu Ala Ser
1               5

<210> SEQ ID NO 3
<211> LENGTH: 12
<212> TYPE: PRT
<213> ORGANISM: Oryctolagus cuniculus

<400> SEQUENCE: 3

Ala Gly Tyr Lys Gly Gly Arg Asn Asp Gly Phe Ala
1               5                   10

<210> SEQ ID NO 4
<211> LENGTH: 10
<212> TYPE: PRT
<213> ORGANISM: Oryctolagus cuniculus

<400> SEQUENCE: 4

Gly Ile Asp Leu Ser Ser His Asp Met Tyr
1               5                   10

<210> SEQ ID NO 5
<211> LENGTH: 16
<212> TYPE: PRT
<213> ORGANISM: Oryctolagus cuniculus

<400> SEQUENCE: 5

Ala Ile Tyr Ala Ser Gly Ser Thr Tyr Tyr Ala Ser Trp Ala Lys Gly
1               5                   10                  15

<210> SEQ ID NO 6
<211> LENGTH: 9
<212> TYPE: PRT
<213> ORGANISM: Oryctolagus cuniculus

<400> SEQUENCE: 6

Ile His Tyr Gly Asn Ser Gly Gly Leu
1               5

<210> SEQ ID NO 7
<211> LENGTH: 13
<212> TYPE: PRT
<213> ORGANISM: Artificial Sequence
<220> FEATURE:
<223> OTHER INFORMATION: CDR-L1 N33R

<400> SEQUENCE: 7

Gln Ala Ser Gln Ser Val Tyr Lys Asn Arg Tyr Leu Ala

```
<210> SEQ ID NO 8
<211> LENGTH: 16
<212> TYPE: PRT
<213> ORGANISM: Artificial Sequence
<220> FEATURE:
<223> OTHER INFORMATION: CDR-H2 S56N

<400> SEQUENCE: 8

Ala Ile Tyr Ala Ser Gly Asn Thr Tyr Tyr Ala Ser Trp Ala Lys Gly
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: CDR-H3 N102H

<400> SEQUENCE: 9

Ile His Tyr Gly His Ser Gly Gly Leu
1               5

<210> SEQ ID NO 10
<211> LENGTH: 140
<212> TYPE: PRT
<213> ORGANISM: Homo sapiens

<400> SEQUENCE: 10

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 11
<211> LENGTH: 112
<212> TYPE: PRT
<213> ORGANISM: Oryctolagus cuniculus

<400> SEQUENCE: 11

Ala Ile Val Met Thr Gln Thr Pro Ser Ser Lys Ser Val Ala Val Gly
1               5                   10                  15

Asp Thr Val Thr Ile Asn Cys Gln Ala Ser Gln Ser Val Tyr Lys Asn
            20                  25                  30

Asn Tyr Leu Ala Trp Phe Gln Gln Lys Pro Gly Gln Pro Pro Lys Gln
        35                  40                  45
```

Leu Ile Tyr Gly Ala Ser Thr Leu Ala Ser Gly Val Pro Ser Arg Phe
         50                  55                  60

Lys Gly Ser Gly Ser Gly Thr Gln Phe Thr Leu Thr Ile Ser Asp Val
 65                  70                  75                  80

Val Cys Asp Asp Ala Ala Thr Tyr Tyr Cys Ala Gly Tyr Lys Gly Gly
                 85                  90                  95

Arg Asn Asp Gly Phe Ala Phe Gly Gly Gly Thr Glu Val Val Val Lys
            100                 105                 110

<210> SEQ ID NO 12
<211> LENGTH: 336
<212> TYPE: DNA
<213> ORGANISM: Oryctolagus cuniculus

<400> SEQUENCE: 12
gccatcgtga tgacccagac tccatcttcc aagtctgtcg ctgtgggaga cacagtcacc      60
atcaattgcc aggccagtca gagtgtttat aagaacaact acttagcctg gtttcaacag     120
aaaccagggc agcctcccaa acaactgatc tatggtgcgt ccactctggc atctggggtc     180
ccatcgcggt tcaaaggcag tggatctggg acacagttca ctctcaccat cagcgatgtg     240
gtgtgtgacg atgctgccac ttactactgt gcaggatata aggtggtcg taatgatggt      300 tttgctttcg gcggagggac cgaggtggtg gtcaaa                               336

<210> SEQ ID NO 13
<211> LENGTH: 114
<212> TYPE: PRT
<213> ORGANISM: Oryctolagus cuniculus

<400> SEQUENCE: 13

Gln Ser Val Glu Glu Ser Gly Gly Arg Leu Val Thr Pro Gly Thr Pro
  1               5                  10                  15

Leu Thr Leu Thr Cys Thr Val Ser Gly Ile Asp Leu Ser Ser His Asp
             20                  25                  30

Met Tyr Trp Val Arg Gln Ala Pro Gly Lys Gly Leu Glu Tyr Ile Gly
         35                  40                  45

Ala Ile Tyr Ala Ser Gly Ser Thr Tyr Tyr Ala Ser Trp Ala Lys Gly
     50                  55                  60

Arg Phe Thr Ile Ser Lys Thr Ser Thr Thr Val Asp Leu Lys Met Thr
 65                  70                  75                  80

Ser Leu Thr Thr Glu Asp Thr Ala Thr Tyr Phe Cys Ala Arg Ile His
                 85                  90                  95

Tyr Gly Asn Ser Gly Gly Leu Trp Gly Gln Gly Thr Leu Val Thr Val
            100                 105                 110

Ser Ser

<210> SEQ ID NO 14
<211> LENGTH: 342
<212> TYPE: DNA
<213> ORGANISM: Oryctolagus cuniculus

<400> SEQUENCE: 14
cagtcggtgg aggagtccgg gggtcgcctg gtcacgcctg gacacccct gacactcacc       60 tgcacagtct ctggaatcga cctcagtagc cacgacatgt attgggtccg ccaggctcca     120
gggaaggggc tggaatacat tggagccatt tatgctagtg gtagcacata ctacgcgagc     180
tgggcgaaag gccgattcac catctccaag acctcgacca cggtggatct gaaaatgacc     240

```
agtctgacaa ccgaggacac ggccacctat ttctgtgcca gaattcatta tggtaatagt    300
ggtgggttgt ggggccaagg caccctggtc accgtctcga gt                       342
```

<210> SEQ ID NO 15
<211> LENGTH: 112
<212> TYPE: PRT
<213> ORGANISM: Artificial Sequence
<220> FEATURE:
<223> OTHER INFORMATION: 6470 gL3 VL

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Tyr Lys Asn
            20                  25                  30

Asn Tyr Leu Ala Trp Phe Gln Gln Lys Pro Gly Lys Ala Pro Lys Gln
        35                  40                  45

Leu Ile Tyr Gly Ala Ser Thr Leu Ala Ser Gly Val Pro Ser Arg Phe
    50                  55                  60

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Ala Gly Tyr Lys Gly Gly
                85                  90                  95

Arg Asn Asp Gly Phe Ala Phe Gly Gly Gly Thr Lys Val Glu Ile Lys
            100                 105                 110
```

<210> SEQ ID NO 16
<211> LENGTH: 336
<212> TYPE: DNA
<213> ORGANISM: Artificial Sequence
<220> FEATURE:
<223> OTHER INFORMATION: 6470 gL3 VL nucl.

<400> SEQUENCE: 16

```
gacattcaga tgacccagtc cccttcatca ctgtccgcga gcgtgggcga cagagtgacc    60
attacgtgcc aagccagcca gtccgtgtac aagaacaact acctggcctg gttccagcaa   120
aagcccggga aggcgccaaa acagcttatc tacggtgcat ccactctcgc ctcgggagtg   180
ccgagccgct tctcgggatc tgggtccgga actcagttca ccctgactat ctcgtccctg   240
caacccgagg atttcgccac ctactactgc gccggctata agggaggacg gaacgacggc   300
ttcgcttttg gtggaggcac caaggtcgaa atcaag                             336
```

<210> SEQ ID NO 17
<211> LENGTH: 219
<212> TYPE: PRT
<213> ORGANISM: Artificial Sequence
<220> FEATURE:
<223> OTHER INFORMATION: 6470 gL3 Light chain

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Tyr Lys Asn
            20                  25                  30

Asn Tyr Leu Ala Trp Phe Gln Gln Lys Pro Gly Lys Ala Pro Lys Gln
        35                  40                  45

Leu Ile Tyr Gly Ala Ser Thr Leu Ala Ser Gly Val Pro Ser Arg Phe
    50                  55                  60
```

Ser Gly Ser Gly Ser Gly Thr Gln Phe Thr Leu Thr Ile Ser Ser Leu
65                  70                  75                  80

Gln Pro Glu Asp Phe Ala Thr Tyr Tyr Cys Ala Gly Tyr Lys Gly Gly
                85                  90                  95

Arg Asn Asp Gly Phe Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 18
<211> LENGTH: 657
<212> TYPE: DNA
<213> ORGANISM: Artificial Sequence
<220> FEATURE:
<223> OTHER INFORMATION: 6470 gL3 Light chain nucl.

<400> SEQUENCE: 18
gacattcaga tgacccagtc cccttcatca ctgtccgcga gcgtgggcga cagagtgacc      60
attacgtgcc aagccagcca gtccgtgtac aagaacaact acctggcctg gttccagcaa    120
aagcccggga aggcgccaaa acagcttatc tacggtgcat ccactctcgc ctcgggagtg    180
ccgagccgct tctcgggatc tgggtccgga actcagttca ccctgactat ctcgtccctg    240
caacccgagg atttcgccac ctactactgc gccggctata aggaggacg gaacgacggc     300
ttcgcttttg gtggaggcac caaggtcgaa atcaagcgta cggtggccgc tcccctccgtg   360
ttcatcttcc caccctccga cgagcagctg aagtccggca ccgcctccgt cgtgtgcctg    420
ctgaacaact ctaccccccg cgaggccaag gtgcagtgga aggtggacaa cgccctgcag    480
tccggcaact cccaggaatc cgtcaccgag caggactcca aggacagcac ctactccctg    540
tcctccaccc tgaccctgtc caaggccgac tacgagaagc acaaggtgta cgcctgcgaa    600
gtgacccacc agggcctgtc cagccccgtg accaagtcct tcaaccgggg cgagtgc       657

<210> SEQ ID NO 19
<211> LENGTH: 112
<212> TYPE: PRT
<213> ORGANISM: Artificial Sequence
<220> FEATURE:
<223> OTHER INFORMATION: 6470 gL3 VL N33R

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Tyr Lys Asn
            20                  25                  30

```
Arg Tyr Leu Ala Trp Phe Gln Gln Lys Pro Gly Lys Ala Pro Lys Gln
             35                  40                  45

Leu Ile Tyr Gly Ala Ser Thr Leu Ala Ser Gly Val Pro Ser Arg Phe
 50                  55                  60

Ser Gly Ser Gly Ser Gly Thr Gln Phe Thr Leu Thr Ile Ser Ser Leu
 65                  70                  75                  80

Gln Pro Glu Asp Phe Ala Thr Tyr Tyr Cys Ala Gly Tyr Lys Gly Gly
                 85                  90                  95

Arg Asn Asp Gly Phe Ala Phe Gly Gly Gly Thr Lys Val Glu Ile Lys
            100                 105                 110
```

<210> SEQ ID NO 20
<211> LENGTH: 336
<212> TYPE: DNA
<213> ORGANISM: Artificial Sequence
<220> FEATURE:
<223> OTHER INFORMATION: 6470 gL3 VL N33R nucl.

<400> SEQUENCE: 20

```
gacattcaga tgacccagtc cccttcatca ctgtccgcga gcgtgggcga cagagtgacc      60
attacgtgcc aagccagcca gtccgtgtac aagaaccgtt acctggcctg gttccagcaa     120
aagcccggga aggcgccaaa acagcttatc tacggtgcat ccactctcgc ctcgggagtg     180
ccgagccgct tctcgggatc tgggtccgga actcagttca ccctgactat ctcgtccctg     240
caacccgagg atttcgccac ctactactgc gccggctata agggaggacg gaacgacggc     300
ttcgcttttg gtggaggcac caaggtcgaa atcaag                              336
```

<210> SEQ ID NO 21
<211> LENGTH: 219
<212> TYPE: PRT
<213> ORGANISM: Artificial Sequence
<220> FEATURE:
<223> OTHER INFORMATION: 6470 gL3 Light chain N33R

<400> SEQUENCE: 21

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Val Tyr Lys Asn
             20                  25                  30

Arg Tyr Leu Ala Trp Phe Gln Gln Lys Pro Gly Lys Ala Pro Lys Gln
             35                  40                  45

Leu Ile Tyr Gly Ala Ser Thr Leu Ala Ser Gly Val Pro Ser Arg Phe
 50                  55                  60

Ser Gly Ser Gly Ser Gly Thr Gln Phe Thr Leu Thr Ile Ser Ser Leu
 65                  70                  75                  80

Gln Pro Glu Asp Phe Ala Thr Tyr Tyr Cys Ala Gly Tyr Lys Gly Gly
                 85                  90                  95

Arg Asn Asp Gly Phe Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 22
<211> LENGTH: 657
<212> TYPE: DNA
<213> ORGANISM: Artificial Sequence
<220> FEATURE:
<223> OTHER INFORMATION: 6470 gL3 Light chain N33R nucl.

<400> SEQUENCE: 22

```
gacattcaga tgacccagtc cccttcatca ctgtccgcga gcgtgggcga cagagtgacc      60
attacgtgcc aagccagcca gtccgtgtac aagaaccgtt acctggcctg gttccagcaa     120
aagcccggga aggcgccaaa acagcttatc tacggtgcat ccactctcgc ctcgggagtg     180
ccgagccgct ctcgggatc tgggtccgga actcagttca ccctgactat ctcgtccctg      240
caacccgagg atttcgccac ctactactgc gccggctata aggaggacg gaacgacggc     300
ttcgcttttg gtggaggcac caaggtcgaa atcaagcgta cggtggccgc tccctccgtg     360
ttcatcttcc caccctccga cgagcagctg aagtccggca ccgcctccgt cgtgtgcctg     420
ctgaacaact ctacccccg cgaggccaag gtgcagtgga aggtggacaa cgccctgcag     480
tccggcaact cccaggaatc cgtcaccgag caggactcca aggacagcac ctactccctg     540
tcctccaccc tgaccctgtc aaggccgac tacgagaagc acaaggtgta cgcctgcgaa     600
gtgacccacc agggcctgtc cagccccgtg accaagtcct tcaaccgggg cgagtgc       657
```

<210> SEQ ID NO 23
<211> LENGTH: 117
<212> TYPE: PRT
<213> ORGANISM: Artificial Sequence
<220> FEATURE:
<223> OTHER INFORMATION: 6470 gH23 VH

<400> SEQUENCE: 23

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Ser His
            20                  25                  30

Asp Met Tyr Trp Val Arg Gln Ala Pro Gly Lys Gly Leu Glu Tyr Ile
        35                  40                  45

Gly Ala Ile Tyr Ala Ser Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ile His Tyr Gly Asn Ser Gly Gly Leu Trp Gly Gln Gly Thr Leu
            100                 105                 110

Val Thr Val Ser Ser
        115
```

<210> SEQ ID NO 24
<211> LENGTH: 351

<212> TYPE: DNA
<213> ORGANISM: Artificial Sequence
<220> FEATURE:
<223> OTHER INFORMATION: 6479gH23 VH nucl.

<400> SEQUENCE: 24

```
gaggttcagc tgctggagtc tggaggcggg cttgtccagc ctggagggag cctgcgtctc    60
tcttgtgcag taagcggcat cgacctgtcc agccacgaca tgtattgggt acgtcaggca   120
ccgggtaaag gtctggaata catcggcgcc atttatgcta gtggtagcac atactacgcg   180
agctgggcga aaggccgttt caccatctcc cgtgacaact ctaaaaacac cgtgtacctg   240
cagatgaact ctctgcgtgc ggaagacact gcggtttact attgcgcgcg tattcattat   300
ggtaatagtg gtgggttgtg gggtcagggt actctggtta ccgtctcgag c            351
```

<210> SEQ ID NO 25
<211> LENGTH: 444
<212> TYPE: PRT
<213> ORGANISM: Artificial Sequence
<220> FEATURE:
<223> OTHER INFORMATION: 6470 gH23 Heavy chain

<400> SEQUENCE: 25

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Ser His
            20                  25                  30

Asp Met Tyr Trp Val Arg Gln Ala Pro Gly Lys Gly Leu Glu Tyr Ile
        35                  40                  45

Gly Ala Ile Tyr Ala Ser Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ile His Tyr Gly Asn Ser Gly Gly Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270
```

```
Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 26
<211> LENGTH: 1332
<212> TYPE: DNA
<213> ORGANISM: Artificial Sequence
<220> FEATURE:
<223> OTHER INFORMATION: 6470gH23 Heavy chain nucl.

<400> SEQUENCE: 26

```
gaggttcagc tgctggagtc tggaggcggg cttgtccagc ctggagggag cctgcgtctc      60
tcttgtgcag taagcggcat cgacctgtcc agccacgaca tgtattgggt acgtcaggca     120
ccgggtaaag gtctggaata catcggcgcc atttatgcta gtggtagcac atactacgcg     180
agctgggcga aaggccgttt caccatctcc cgtgacaact ctaaaaacac cgtgtacctg     240
cagatgaact ctctgcgtgc ggaagacact gcggtttact attgcgcgcg tattcattat     300
ggtaatagtg gtgggttgtg gggtcagggt actctggtta ccgtctcgag cgcttctaca     360
aagggcccct ccgtgttccc tctggccccc tgctcccggt ccacctccga gtctaccgcc     420
gctctgggct gcctggtcaa ggactacttc cccgagcccg tgacagtgtc ctggaactct     480
ggcgccctga cctccggcgt gcacaccttc cctgccgtgc tgcagtcctc cggcctgtac     540
tccctgtcct ccgtcgtgac cgtgccctcc tccagcctgg caccaagac ctacacctgt     600
aacgtggacc acaagccctc caacaccaag gtggacaagc gggtggaatc taagtacggc     660
cctccctgcc ccccctgccc tgcccctgaa tttctgggcg accttccgt gttcctgttc     720
cccccaaagc ccaaggacac cctgatgatc tcccggaccc ccgaagtgac ctgcgtggtg     780
gtggacgtgt cccaggaaga tcccgaggtc cagttcaatt ggtacgtgga cggcgtggaa     840
gtgcacaatg ccaagaccaa gccagagag gaacagttca actccaccta ccgggtggtg     900
tccgtgctga ccgtgctgca ccaggactgg ctgaacggca agagtacaa gtgcaaggtg     960
tccaacaagg gcctgccctc cagcatcgaa aagaccatct ccaaggccaa ggccagccc     1020
cgcgagcccc aggtgtacac cctgcccct agccaggaag agatgaccaa gaaccaggtg    1080
```

```
tccctgacct gtctggtcaa gggcttctac ccctccgaca ttgccgtgga atgggagtcc   1140
aacggccagc ccgagaacaa ctacaagacc accccccctg tgctggacag cgacggctcc   1200
ttcttcctgt actctcggct gaccgtggac aagtcccggt ggcaggaagg caacgtcttc   1260
tcctgctccg tgatgcacga ggccctgcac aaccactaca cccagaagtc cctgtccctg   1320
agcctgggca ag                                                       1332
```

```
<210> SEQ ID NO 27
<211> LENGTH: 117
<212> TYPE: PRT
<213> ORGANISM: Artificial Sequence
<220> FEATURE:
<223> OTHER INFORMATION: 6470 gH23 VH S56N N102H

<400> SEQUENCE: 27
```

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Ser His
            20                  25                  30

Asp Met Tyr Trp Val Arg Gln Ala Pro Gly Lys Gly Leu Glu Tyr Ile
        35                  40                  45

Gly Ala Ile Tyr Ala Ser Gly Asn Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ile His Tyr Gly His Ser Gly Gly Leu Trp Gly Gln Gly Thr Leu
            100                 105                 110

Val Thr Val Ser Ser
        115
```

```
<210> SEQ ID NO 28
<211> LENGTH: 351
<212> TYPE: DNA
<213> ORGANISM: Artificial Sequence
<220> FEATURE:
<223> OTHER INFORMATION: 6470 gH23 VH S56N N102H nucl.

<400> SEQUENCE: 28
```

```
gaggttcagc tgctggagtc tggaggcggg cttgtccagc ctggaggag cctgcgtctc    60 tcttgtgcag taagcggcat cgacctgtcc agccacgaca tgtattgggt acgtcaggca   120
ccgggtaaag gtctggaata catcggcgcc atttatgcta gtggtaatac atactacgcg   180
agctgggcga aaggccgttt caccatctcc cgtgacaact ctaaaaacac cgtgtacctg   240
cagatgaact ctctgcgtgc ggaagacact gcggtttact attgcgcgcg tattcattat   300
ggtcacagtg gtgggttgtg ggtcagggt actctggtta ccgtctcgag c             351
```

```
<210> SEQ ID NO 29
<211> LENGTH: 444
<212> TYPE: PRT
<213> ORGANISM: Artificial Sequence
<220> FEATURE:
<223> OTHER INFORMATION: 6470 gH23 Heavy chain S56N N102H

<400> SEQUENCE: 29
```

```
Glu Val Gln Leu Leu Glu Ser Gly Gly Gly Leu Val Gln Pro Gly Gly
1               5                   10                  15
```

```
Ser Leu Arg Leu Ser Cys Ala Val Ser Gly Ile Asp Leu Ser Ser His
            20                  25                  30

Asp Met Tyr Trp Val Arg Gln Ala Pro Gly Lys Gly Leu Glu Tyr Ile
            35                  40                  45

Gly Ala Ile Tyr Ala Ser Gly Asn Thr Tyr Tyr Ala Ser Trp Ala Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                85                  90                  95

Arg Ile His Tyr Gly His Ser Gly Gly Leu Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430
```

Tyr Thr Gln Lys Ser Leu Ser Leu Ser Leu Gly Lys
            435                 440

<210> SEQ ID NO 30
<211> LENGTH: 1332
<212> TYPE: DNA
<213> ORGANISM: Artificial Sequence
<220> FEATURE:
<223> OTHER INFORMATION: 6470 gH23 heavy chain S56N N102H nucl.

<400> SEQUENCE: 30

```
gaggttcagc tgctggagtc tggaggcggg cttgtccagc ctggagggag cctgcgtctc     60
tcttgtgcag taagcggcat cgacctgtcc agccacgaca tgtattgggt acgtcaggca    120
ccgggtaaag gtctggaata catcggcgcc atttatgcta gtggtaatac atactacgcg    180
agctgggcga aaggccgttt caccatctcc cgtgacaact ctaaaaacac cgtgtacctg    240
cagatgaact ctctgcgtgc ggaagacact gcggtttact attgcgcgcg tattcattat    300
ggtcacagtg gtgggttgtg ggtcagggt actctggtta ccgtctcgag cgcttctaca    360
aagggcccct ccgtgttccc tctggcccct gctcccggt ccacctccga gtctaccgcc    420
gctctgggct gcctggtcaa ggactacttc cccgagcccg tgacagtgtc ctggaactct    480
ggcgccctga cctccggcgt gcacaccttc cctgccgtgc tgcagtcctc cggcctgtac    540
tccctgtcct ccgtcgtgac cgtgccctcc tccagcctgg gcaccaagac ctacacctgt    600
aacgtggacc acaagccctc caacaccaag gtggacaagc gggtggaatc taagtacggc    660
cctccctgcc cccctgccc tgcccctgaa tttctgggcg accttccgt gttcctgttc    720
cccccaaagc ccaaggacac cctgatgatc tcccggaccc ccgaagtgac ctgcgtggtg    780
gtggacgtgt cccaggaaga tcccgaggtc cagttcaatt ggtacgtgga cggcgtggaa    840
gtgcacaatg ccaagaccaa gcccagagag gaacagttca actccaccta ccgggtggtg    900
tccgtgctga ccgtgctgca ccaggactgg ctgaacggca agagtacaa gtgcaaggtg    960
tccaacaagg cctgccctc cagcatcgaa aagaccatct ccaaggccaa gggccagccc   1020
cgcgagcccc aggtgtacac cctgccccct agccaggaag atgaccaa gaaccaggtg   1080
tccctgacct gtctggtcaa gggcttctac ccctccgaca ttgccgtgga atgggagtcc   1140
aacggccagc ccgagaacaa ctacaagacc accccccctg tgctggacag cgacggctcc   1200
ttcttcctgt actctcggct gaccgtggac aagtcccggt ggcaggaagg caacgtcttc   1260
tcctgctccg tgatgcacga ggccctgcac aaccactaca cccagaagtc cctgtccctg   1320
agcctgggca ag                                                      1332
```

<210> SEQ ID NO 31
<211> LENGTH: 117
<212> TYPE: PRT
<213> ORGANISM: Artificial Sequence
<220> FEATURE:
<223> OTHER INFORMATION: 6470 gH36 VH

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Ser His
            20                  25                  30

Asp Met Tyr Trp Val Arg Gln Ala Pro Gly Lys Gly Leu Glu Tyr Ile
        35                  40                  45

Gly Ala Ile Tyr Ala Ser Gly Ser Thr Tyr Tyr Ala Ser Trp Ala Lys

```
                    50                  55                  60
Gly Arg Phe Thr Ile Ser Arg Asp Ser Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ile His Tyr Gly Asn Ser Gly Gly Leu Trp Gly Gln Gly Thr Leu
                100                 105                 110

Val Thr Val Ser Ser
            115

<210> SEQ ID NO 32
<211> LENGTH: 351
<212> TYPE: DNA
<213> ORGANISM: Artificial Sequence
<220> FEATURE:
<223> OTHER INFORMATION: 6470 gH36 VH nucl.

<400> SEQUENCE: 32
gaggttcagc tgctggagtc tggaggcggg cttgtccagc ctggaggag cctgcgtctc     60 tcttgtgcag taagcggcat cgacctgtcc agccacgaca tgtattgggt acgtcaggca   120
ccgggtaaag gtctggaata catcggcgcc atttatgcta gtggtagcac atactacgcg   180
agctgggcga aaggccgttt caccatctcc cgtgactcca gcaaaaacac cctgtacctg   240
cagatgaact ctctgcgtgc ggaagacact gcggtttact attgcgcgcg tattcattat   300
ggtaatagtg gtgggttgtg gggtcagggt actctggtta ccgtctcgag c            351

<210> SEQ ID NO 33
<211> LENGTH: 444
<212> TYPE: PRT
<213> ORGANISM: Artificial Sequence
<220> FEATURE:
<223> OTHER INFORMATION: 6470 gH36 Heavy chain

<400> SEQUENCE: 33

Glu Val Gln Leu Leu Glu Ser Gly Gly Gly Leu Val Gln Pro Gly Gly
 1               5                  10                  15

Ser Leu Arg Leu Ser Cys Ala Val Ser Gly Ile Asp Leu Ser Ser His
             20                  25                  30

Asp Met Tyr Trp Val Arg Gln Ala Pro Gly Lys Gly Leu Glu Tyr Ile
             35                  40                  45

Gly Ala Ile Tyr Ala Ser Gly Ser Thr Tyr Tyr Ala Ser Trp Ala Lys
         50                  55                  60

Gly Arg Phe Thr Ile Ser Arg Asp Ser Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ile His Tyr Gly Asn Ser Gly Gly Leu Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 34
<211> LENGTH: 1332
<212> TYPE: DNA
<213> ORGANISM: Artificial Sequence
<220> FEATURE:
<223> OTHER INFORMATION: 6470 gH36 Heavy chain nucl.

<400> SEQUENCE: 34

```
gaggttcagc tgctggagtc tggaggcggg cttgtccagc ctggagggag cctgcgtctc      60
tcttgtgcag taagcggcat cgacctgtcc agccacgaca tgtattgggt acgtcaggca     120
ccgggtaaag gtctggaata catcggcgcc atttatgcta gtggtagcac atactacgcg     180
agctgggcga aaggccgttt caccatctcc cgtgactcca gcaaaaacac cctgtacctg     240
cagatgaact ctctgcgtgc ggaagacact gcggtttact attgcgcgcg tattcattat     300
ggtaatagtg gtgggttgtg gggtcagggt actctggtta ccgtctcgag cgcttctaca     360
aagggcccct ccgtgttccc tctggcccct gctcccggt ccacctccga gtctaccgcc     420
gctctgggct gcctggtcaa ggactacttc cccgagcccg tgacagtgtc ctggaactct     480
ggcgccctga cctccggcgt gcacaccttc cctgccgtgc tgcagtcctc cggcctgtac     540
```

```
tccctgtcct ccgtcgtgac cgtgccctcc tccagcctgg gcaccaagac ctacacctgt      600
aacgtggacc acaagccctc caacaccaag gtggacaagc gggtggaatc taagtacggc      660
cctccctgcc ccccctgccc tgcccctgaa tttctgggcg accttccgt gttcctgttc       720 cccccaaagc ccaaggacac cctgatgatc tcccggaccc ccgaagtgac ctgcgtggtg      780
gtggacgtgt cccaggaaga tcccgaggtc cagttcaatt ggtacgtgga cggcgtggaa      840
gtgcacaatg ccaagaccaa gcccagagag aacagttca actccaccta ccgggtggtg      900
tccgtgctga ccgtgctgca ccaggactgg ctgaacggca agagtacaa gtgcaaggtg       960 tccaacaagg gcctgccctc cagcatcgaa aagaccatct ccaaggccaa gggccagccc     1020
cgcgagcccc aggtgtacac cctgccccct agccaggaag agatgaccaa gaaccaggtg     1080
tccctgacct gtctggtcaa ggcttctac ccctccgaca ttgccgtgga atgggagtcc      1140
aacggccagc ccgagaacaa ctacaagacc accccccctg tgctggacag cgacggctcc     1200
ttcttcctgt actctcggct gaccgtggac aagtcccggt ggcaggaagg caacgtcttc     1260
tcctgctccg tgatgcacga ggccctgcac aaccactaca cccagaagtc cctgtccctg     1320
agcctgggca ag                                                         1332
```

```
<210> SEQ ID NO 35
<211> LENGTH: 117
<212> TYPE: PRT
<213> ORGANISM: Artificial Sequence
<220> FEATURE:
<223> OTHER INFORMATION: 6470 gH36 VH S56N N102H

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Ser His
            20                  25                  30

Asp Met Tyr Trp Val Arg Gln Ala Pro Gly Lys Gly Leu Glu Tyr Ile
        35                  40                  45

Gly Ala Ile Tyr Ala Ser Gly Asn Thr Tyr Tyr Ala Ser Trp Ala Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ile His Tyr Gly His Ser Gly Gly Leu Trp Gly Gln Gly Thr Leu
            100                 105                 110

Val Thr Val Ser Ser
        115
```

```
<210> SEQ ID NO 36
<211> LENGTH: 351
<212> TYPE: DNA
<213> ORGANISM: Artificial Sequence
<220> FEATURE:
<223> OTHER INFORMATION: 6470 gH36 VH S56N N102H nucl.

<400> SEQUENCE: 36
gaggttcagc tgctggagtc tggaggcggg cttgtccagc ctggagggag cctgcgtctc       60
tcttgtgcag taagcggcat cgacctgtca agccacgaca tgtattgggt acgtcaggca     120
ccgggtaaag gtctggaata catcggcgcc atttatgcta gtggtaatac atactacgcg     180
agctgggcga aaggccgttt caccatctcc cgtgactcca gcaaaaacac cctgtacctg     240
```
cagatgaact ctctgcgtgc ggaagacact gcggtttact attgcgcgcg tattcattat    300
ggtcacagtg gtgggttgtg gggtcagggt actctggtta ccgtctcgag c              351

<210> SEQ ID NO 37
<211> LENGTH: 444
<212> TYPE: PRT
<213> ORGANISM: Artificial Sequence
<220> FEATURE:
<223> OTHER INFORMATION: 6470 gH36 Heavy chain S56N N102H

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Ser His
            20                  25                  30

Asp Met Tyr Trp Val Arg Gln Ala Pro Gly Lys Gly Leu Glu Tyr Ile
        35                  40                  45

Gly Ala Ile Tyr Ala Ser Gly Asn Thr Tyr Tyr Ala Ser Trp Ala Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ile His Tyr Gly His Ser Gly Gly Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln

|      | 340 |     |     |     | 345 |     |     |     | 350 |     |     |
|------|-----|-----|-----|-----|-----|-----|-----|-----|-----|-----|-----|

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
        435                 440

```
<210> SEQ ID NO 38
<211> LENGTH: 1332
<212> TYPE: DNA
<213> ORGANISM: Artificial Sequence
<220> FEATURE:
<223> OTHER INFORMATION: 6470 gH36 Heavy chain S56N N102H nucl.

<400> SEQUENCE: 38
gaggttcagc tgctggagtc tggaggcggg cttgtccagc ctggagggag cctgcgtctc     60
tcttgtgcag taagcggcat cgacctgtcc agccacgaca tgtattgggt acgtcaggca    120
ccgggtaaag gtctggaata catcggcgcc atttatgcta gtggtaatac atactacgcg    180
agctgggcga aaggccgttt caccatctcc cgtgactcca gcaaaaacac cctgtacctg    240
cagatgaact ctctgcgtgc ggaagacact gcggtttact attgcgcgcg tattcattat    300
ggtcacagtg gtgggttgtg gggtcagggt actctggtta ccgtctcgag cgcttctaca    360
aagggcccct ccgtgttccc tctggcccct gctcccggt ccacctccga gtctaccgcc    420
gctctgggct gcctggtcaa ggactacttc cccgagcccg tgacagtgtc ctggaactct    480
ggcgccctga cctccggcgt gcacaccttc cctgccgtgc tgcagtcctc cggcctgtac    540
tccctgtcct ccgtcgtgac cgtgccctcc tccagcctgg caccaagac ctacacctgt    600 aacgtggacc acaagccctc caacaccaag gtggacaagc gggtggaatc taagtacggc    660
cctccctgcc ccctgcc tgccctgaa tttctgggcg gaccttccgt gttcctgttc    720
cccccaaagc caaggacac cctgatgatc tcccggaccc cgaagtgac ctgcgtggtg    780 gtggacgtgt cccaggaaga tcccgaggtc cagttcaatt ggtacgtgga cggcgtggaa    840
gtgcacaatg ccaagaccaa gccagagag gaacagttca ctccaccta ccgggtggtg    900 tccgtgctga ccgtgctgca ccaggactgg ctgaacggca agagtacaa gtgcaaggtg    960 tccaacaagg gcctgccctc cagcatcgaa aagaccatct ccaaggccaa gggccagccc   1020
cgcgagcccc aggtgtacac cctgccccct agccaggaag atgaccaa gaaccaggtg   1080 tccctgacct gtctggtcaa gggcttctac ccctccgaca ttgccgtgga atgggagtcc   1140
aacggccagc ccgagaacaa ctacaagacc accccccctg tgctggacag cgacggctcc   1200
ttcttcctgt actctcggct gaccgtggac aagtccggt ggcaggaagg caacgtcttc   1260
tcctgctccg tgatgcacga ggccctgcac aaccactaca cccagaagtc cctgtccctg   1320
agcctgggca ag                                                       1332

<210> SEQ ID NO 39
<211> LENGTH: 107
```

<212> TYPE: PRT
<213> ORGANISM: Artificial Sequence
<220> FEATURE:
<223> OTHER INFORMATION: Human IGKV1-16 JK4 acceptor framework

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 40
<211> LENGTH: 321
<212> TYPE: DNA
<213> ORGANISM: Artificial Sequence
<220> FEATURE:
<223> OTHER INFORMATION: Human IGKV1-16 JK4 acceptor framework nucl.

<400> SEQUENCE: 40

```
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt accctctcac tttcggcgga   300
gggaccaagg tggagatcaa a                                             321
```

<210> SEQ ID NO 41
<211> LENGTH: 113
<212> TYPE: PRT
<213> ORGANISM: Artificial Sequence
<220> FEATURE:
<223> OTHER INFORMATION: Human IGHV3-23 JH4 acceptor framework

<400> SEQUENCE: 41

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Phe Asp Tyr Trp Gly Gln Gly Thr Leu Val Thr Val Ser
```

Ser

<210> SEQ ID NO 42
<211> LENGTH: 339
<212> TYPE: DNA
<213> ORGANISM: Artificial Sequence
<220> FEATURE:
<223> OTHER INFORMATION: Human IGHV3-23 JH4 acceptor framework nucl.

<400> SEQUENCE: 42

```
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaatacttt    300
gactactggg gccaaggaac cctggtcacc gtctcctca                            339
```

<210> SEQ ID NO 43
<211> LENGTH: 306
<212> TYPE: PRT
<213> ORGANISM: Artificial Sequence
<220> FEATURE:
<223> OTHER INFORMATION: Rabbit Fc - human 68-140 a-syn

<400> SEQUENCE: 43

Gly Ala Val Val Thr Gly Val Thr Ala Val Ala Gln Lys Thr Val Glu
1               5                   10                  15

Gly Ala Gly Ser Ile Ala Ala Ala Thr Gly Phe Val Lys Lys Asp Gln
                20                  25                  30

Leu Gly Lys Asn Glu Glu Gly Ala Pro Gln Glu Gly Ile Leu Glu Asp
            35                  40                  45

Met Pro Val Asp Pro Asp Asn Glu Ala Tyr Glu Met Pro Ser Glu Glu
        50                  55                  60

Gly Tyr Gln Asp Tyr Glu Pro Glu Ala Val Glu Lys Thr Val Ala Pro
65                  70                  75                  80

Ser Thr Cys Ser Lys Pro Thr Cys Pro Pro Glu Leu Leu Gly Gly
                85                  90                  95

Pro Ser Val Phe Ile Phe Pro Pro Lys Pro Lys Asp Thr Leu Met Ile
            100                 105                 110

Ser Arg Thr Pro Glu Val Thr Cys Val Val Val Asp Val Ser Gln Asp
        115                 120                 125

Asp Pro Glu Val Gln Phe Thr Trp Tyr Ile Asn Asn Glu Gln Val Arg
    130                 135                 140

Thr Ala Arg Pro Pro Leu Arg Glu Gln Gln Phe Asn Ser Thr Ile Arg
145                 150                 155                 160

Val Val Ser Thr Leu Pro Ile Ala His Gln Asp Trp Leu Arg Gly Lys
                165                 170                 175

Glu Phe Lys Cys Lys Val His Asn Lys Ala Leu Pro Ala Pro Ile Glu
            180                 185                 190

Lys Thr Ile Ser Lys Ala Arg Gly Gln Pro Leu Glu Pro Lys Val Tyr
        195                 200                 205

Thr Met Gly Pro Pro Arg Glu Glu Leu Ser Ser Arg Ser Val Ser Leu
    210                 215                 220

Thr Cys Met Ile Asn Gly Phe Tyr Pro Ser Asp Ile Ser Val Glu Trp

```
                225                 230                 235                 240

Glu Lys Asn Gly Lys Ala Glu Asp Asn Tyr Lys Thr Thr Pro Ala Val
                245                 250                 255

Leu Asp Ser Asp Gly Ser Tyr Phe Leu Tyr Ser Lys Leu Ser Val Pro
                260                 265                 270

Thr Ser Glu Trp Gln Arg Gly Asp Val Phe Thr Cys Ser Val Met His
            275                 280                 285

Glu Ala Leu His Asn His Tyr Thr Gln Lys Ser Ile Ser Arg Ser Pro
        290                 295                 300

Gly Lys
305

<210> SEQ ID NO 44
<211> LENGTH: 13
<212> TYPE: PRT
<213> ORGANISM: Artificial Sequence
<220> FEATURE:
<223> OTHER INFORMATION: CDR-L1 X33
<220> FEATURE:
<221> NAME/KEY: MISC_FEATURE
<222> LOCATION: (10)..(10)
<223> OTHER INFORMATION: Xaa is Asn (N) or Arg (R)

<400> SEQUENCE: 44

Gln Ala Ser Gln Ser Val Tyr Lys Asn Xaa Tyr Leu Ala
1               5                   10

<210> SEQ ID NO 45
<211> LENGTH: 16
<212> TYPE: PRT
<213> ORGANISM: Artificial Sequence
<220> FEATURE:
<223> OTHER INFORMATION: CDR-H2 X56
<220> FEATURE:
<221> NAME/KEY: MISC_FEATURE
<222> LOCATION: (7)..(7)
<223> OTHER INFORMATION: Xaa is Ser (S) or Asn (N)

<400> SEQUENCE: 45

Ala Ile Tyr Ala Ser Gly Xaa Thr Tyr Tyr Ala Ser Trp Ala Lys Gly
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: CDR-H3 X102
<220> FEATURE:
<221> NAME/KEY: MISC_FEATURE
<222> LOCATION: (5)..(5)
<223> OTHER INFORMATION: Xaa is Asn (N) or His (H)

<400> SEQUENCE: 46

Ile His Tyr Gly Xaa Ser Gly Gly Leu
1               5

<210> SEQ ID NO 47
<211> LENGTH: 216
<212> TYPE: PRT
<213> ORGANISM: Oryctolagus cuniculus

<400> SEQUENCE: 47

Ala Ile Val Met Thr Gln Thr Pro Ser Ser Lys Ser Val Ala Val Gly
1               5                   10                  15
```

```
Asp Thr Val Thr Ile Asn Cys Gln Ala Ser Gln Ser Val Tyr Lys Asn
             20                  25                  30

Asn Tyr Leu Ala Trp Phe Gln Gln Lys Pro Gly Gln Pro Pro Lys Gln
         35                  40                  45

Leu Ile Tyr Gly Ala Ser Thr Leu Ala Ser Gly Val Pro Ser Arg Phe
     50                  55                  60

Lys Gly Ser Gly Ser Gly Thr Gln Phe Thr Leu Thr Ile Ser Asp Val
 65                  70                  75                  80

Val Cys Asp Asp Ala Ala Thr Tyr Tyr Cys Ala Gly Tyr Lys Gly Gly
                 85                  90                  95

Arg Asn Asp Gly Phe Ala Phe Gly Gly Gly Thr Glu Val Val Val Lys
            100                 105                 110

Arg Thr Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215

<210> SEQ ID NO 48
<211> LENGTH: 437
<212> TYPE: PRT
<213> ORGANISM: Oryctolagus cuniculus

<400> SEQUENCE: 48

Gln Ser Val Glu Glu Ser Gly Gly Arg Leu Val Thr Pro Gly Thr Pro
 1               5                  10                  15

Leu Thr Leu Thr Cys Thr Val Ser Gly Ile Asp Leu Ser Ser His Asp
             20                  25                  30

Met Tyr Trp Val Arg Gln Ala Pro Gly Lys Gly Leu Glu Tyr Ile Gly
         35                  40                  45

Ala Ile Tyr Ala Ser Gly Ser Thr Tyr Tyr Ala Ser Trp Ala Lys Gly
     50                  55                  60

Arg Phe Thr Ile Ser Lys Thr Ser Thr Thr Val Asp Leu Lys Met Thr
 65                  70                  75                  80

Ser Leu Thr Thr Glu Asp Thr Ala Thr Tyr Phe Cys Ala Arg Ile His
                 85                  90                  95

Tyr Gly Asn Ser Gly Gly Leu Trp Gly Gln Gly Thr Leu Val Thr Val
            100                 105                 110

Ser Ser Gly Gln Pro Lys Ala Pro Ser Val Phe Pro Leu Ala Pro Cys
        115                 120                 125

Cys Gly Asp Thr Pro Ser Ser Thr Val Thr Leu Gly Cys Leu Val Lys
    130                 135                 140

Gly Tyr Leu Pro Glu Pro Val Thr Val Thr Trp Asn Ser Gly Thr Leu
145                 150                 155                 160

Thr Asn Gly Val Arg Thr Phe Pro Ser Val Arg Gln Ser Ser Gly Leu
                165                 170                 175
```

Tyr Ser Leu Ser Ser Val Val Ser Val Thr Ser Ser Gln Pro Val
            180                 185                 190

Thr Cys Asn Val Ala His Pro Ala Thr Asn Thr Lys Val Asp Lys Thr
    195                 200                 205

Val Ala Pro Ser Thr Cys Ser Lys Pro Thr Cys Pro Pro Pro Glu Leu
210                 215                 220

Leu Gly Gly Pro Ser Val Phe Ile Phe Pro Lys Pro Lys Asp Thr
225                 230                 235                 240

Leu Met Ile Ser Arg Thr Pro Glu Val Thr Cys Val Val Asp Val
            245                 250                 255

Ser Gln Asp Asp Pro Glu Val Gln Phe Thr Trp Tyr Ile Asn Asn Glu
            260                 265                 270

Gln Val Arg Thr Ala Arg Pro Pro Leu Arg Glu Gln Gln Phe Asn Ser
            275                 280                 285

Thr Ile Arg Val Val Ser Thr Leu Pro Ile Ala His Gln Asp Trp Leu
            290                 295                 300

Arg Gly Lys Glu Phe Lys Cys Lys Val His Asn Lys Ala Leu Pro Ala
305                 310                 315                 320

Pro Ile Glu Lys Thr Ile Ser Lys Ala Arg Gly Gln Pro Leu Glu Pro
                325                 330                 335

Lys Val Tyr Thr Met Gly Pro Pro Arg Glu Glu Leu Ser Ser Arg Ser
                340                 345                 350

Val Ser Leu Thr Cys Met Ile Asn Gly Phe Tyr Pro Ser Asp Ile Ser
            355                 360                 365

Val Glu Trp Glu Lys Asn Gly Lys Ala Glu Asp Asn Tyr Lys Thr Thr
370                 375                 380

Pro Ala Val Leu Asp Ser Asp Gly Ser Tyr Phe Leu Tyr Ser Lys Leu
385                 390                 395                 400

Ser Val Pro Thr Ser Glu Trp Gln Arg Gly Asp Val Phe Thr Cys Ser
                405                 410                 415

Val Met His Glu Ala Leu His Asn His Tyr Thr Gln Lys Ser Ile Ser
            420                 425                 430

Arg Ser Pro Gly Lys
            435

<210> SEQ ID NO 49
<211> LENGTH: 227
<212> TYPE: PRT
<213> ORGANISM: Artificial Sequence
<220> FEATURE:
<223> OTHER INFORMATION: 6470 rabbit Fab-His heavy chain

<400> SEQUENCE: 49

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser His Asp
            20                  25                  30

Met Tyr Trp Val Arg Gln Ala Pro Gly Lys Gly Leu Glu Tyr Ile Gly
        35                  40                  45

Ala Ile Tyr Ala Ser Gly Ser Thr Tyr Tyr Ala Ser Trp Ala Lys Gly
    50                  55                  60

Arg Phe Thr Ile Ser Lys Thr Ser Thr Val Asp Leu Lys Met Thr
65                  70                  75                  80

Ser Leu Thr Thr Glu Asp Thr Ala Thr Tyr Phe Cys Ala Arg Ile His
                85                  90                  95

-continued

```
Tyr Gly Asn Ser Gly Gly Leu Trp Gly Gln Gly Thr Leu Val Thr Val
            100                 105                 110

Ser Ser Gly Gln Pro Lys Ala Pro Ser Val Phe Pro Leu Ala Pro Cys
        115                 120                 125

Cys Gly Asp Thr Pro Ser Ser Thr Val Thr Leu Gly Cys Leu Val Lys
        130                 135                 140

Gly Tyr Leu Pro Glu Pro Val Thr Val Thr Trp Asn Ser Gly Thr Leu
145                 150                 155                 160

Thr Asn Gly Val Arg Thr Phe Pro Ser Val Arg Gln Ser Ser Gly Leu
                165                 170                 175

Tyr Ser Leu Ser Ser Val Val Ser Val Thr Ser Ser Ser Gln Pro Val
            180                 185                 190

Thr Cys Asn Val Ala His Pro Ala Thr Asn Thr Lys Val Asp Lys Thr
            195                 200                 205

Val Ala Pro Ser Thr Cys Ser Lys Pro His His His His His His
        210                 215                 220

His His His
225
```